(12) United States Patent
Lam et al.

(10) Patent No.: US 9,579,400 B2
(45) Date of Patent: Feb. 28, 2017

(54) NANOCARRIERS FOR DRUG DELIVERY

(75) Inventors: Kit S. Lam, Davis, CA (US); Juntao Luo, Sacramento, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 799 days.

(21) Appl. No.: 13/120,140

(22) PCT Filed: Sep. 22, 2009

(86) PCT No.: PCT/US2009/057852
§ 371 (c)(1),
(2), (4) Date: Aug. 8, 2011

(87) PCT Pub. No.: WO2010/039496
PCT Pub. Date: Apr. 8, 2010

(65) Prior Publication Data
US 2011/0286915 A1    Nov. 24, 2011

Related U.S. Application Data

(60) Provisional application No. 61/099,272, filed on Sep. 23, 2008.

(51) Int. Cl.
| | | |
|---|---|---|
| *A61K 9/14* | (2006.01) | |
| *A61K 31/337* | (2006.01) | |
| *A61K 31/704* | (2006.01) | |
| *A61K 31/7048* | (2006.01) | |
| *A61K 49/00* | (2006.01) | |
| *A61K 9/107* | (2006.01) | |
| *A61K 9/51* | (2006.01) | |
| *A61K 47/48* | (2006.01) | |
| *B82Y 5/00* | (2011.01) | |

(52) U.S. Cl.
CPC ........ *A61K 49/0002* (2013.01); *A61K 9/1075* (2013.01); *A61K 9/5146* (2013.01); *A61K 47/488* (2013.01); *A61K 47/48215* (2013.01); *A61K 49/0032* (2013.01); *A61K 49/0082* (2013.01); *B82Y 5/00* (2013.01)

(58) Field of Classification Search
None
See application file for complete search history.

(56) References Cited

U.S. PATENT DOCUMENTS

| | | |
|---|---|---|
| 6,365,191 B1 | 4/2002 | Burman et al. |
| 2002/0041898 A1 | 4/2002 | Unger et al. |
| 2006/0013885 A1 | 1/2006 | Nah et al. |
| 2006/0127310 A1 | 6/2006 | Russell-Jones et al. |
| 2008/0188399 A1 | 8/2008 | Sinko et al. |
| 2009/0203706 A1 | 8/2009 | Zhao et al. |

FOREIGN PATENT DOCUMENTS

| | | |
|---|---|---|
| WO | WO 99/59550 | 11/1999 |
| WO | 2007/084126 A1 | 7/2007 |

OTHER PUBLICATIONS

Gu et al. (Biomacromolecules, 9, 255-262, 2008, published on the web on Dec. 21, 2007) pH-Triggered Reversible . . . .*
Jeong et al. (Journal of Controlled Release, 101, 49-68, 2005) Hydrotropic polymer micelle . . . .*
Choi et al. (Bioconjugate Chem., 1999, 10, 62-65) Poly(ethylene glycol)-block-poly(L-Lysine) Dendrimer . . . .*
Chapman et al. (J. Am. Chem. Soc. 1994, 116, 11195-11196 ) Hydraamphiphiles: Novel Linear Dendritic B . . . .*
Office Action from Japanese Application No. 2011-528068 dated Dec. 25, 2013 with English translation.
Li, et al., "Antimicrobial Activities of Amine- and Guanidine Functionalized-Cholic Acid Derivatives," *Antimicrobial Agents and Chemotherapy*, vol. 43(6), pp. 1347-1349 (Jun. 1999).
International Search Report and Written Opinion for PCT/US12/70508, 11 pages, mailed on Feb. 27, 2013.
International Search Report dated May 6, 2010, issued in related International Patent Application No. PCT/US2009/057852, filed.
Duncan, "Dawning Era of Polymer Therapeutics," 2003, Nature Rev. Drug. Discov., vol. 2, No. 5, 347-360.
Gref et al., "Biodegradable Long-Circulating Polymeric Nanospheres," 1994, Science American Association for the Advancement of Science, vol. 263, No. 5153, pp. 1600-1603.
Luo et al., "Asymmetric poly(ethylene glycol) star polymers with a cholic acid core and their aggregation properties," 2009, Biomacromolecules, vol. 10, No. 4, pp. 900-906.
Xiao et al., "A self-assembling nanopatricle for paclitaxel delivery in ovarian cancer," 2009, Biomaterials, vol. 30, No. 30, pp. 6006-6016.
Chen et al., "Fluorescence study of inclusion complexes between star-shaped cholic acid derivatives and polycyclic aromatic fluorescent probes and the size effects of host," 2008, Journal of Physical Chemistry, vol. 112, No. 11, pp. 3402-3409.
Vijayalakshmi et al., "A simple construction of a bile acid based dendritic light harvesting system," 2005, Organic Letters, vol. 7, No. 13, pp. 2727-2730.

* cited by examiner

*Primary Examiner* — Tigabu Kassa
(74) *Attorney, Agent, or Firm* — Kilpatrick Townsend & Stockton LLP

(57) ABSTRACT

The present invention provides a nanocarrier having an interior and an exterior, the nanocarrier comprising at least one conjugate, wherein each conjugate includes a polyethylene glycol (PEG) polymer. Each conjugate also includes at least two amphiphilic compounds having both a hydrophilic face and a hydrophobic face. In addition, each conjugate includes an oligomer, wherein at least 2 of the amphiphilic compounds are covalently attached to the oligomer which is covalently attached to the PEG. The nanocarrier is such that each conjugate self-assembles in an aqueous solvent to form the nanocarrier such that a hydrophobic pocket is formed in the interior of the nanocarrier by the orientation of the hydrophobic face of each amphiphilic compound towards each other, and wherein the PEG of each conjugate self-assembles on the exterior of the nanocarrier.

8 Claims, 51 Drawing Sheets

Schematic structure and functionalization of the linear polymers.

Schematic structure and functionalization of the two branches polymers.

Schematic structure and functionalization of the three branches polymers.

Schematic structure and functionalization of the telodendrimers.

Figure 25. The design of the biodegradable nanoparticles containing cleavable linkages between the building blocks.

Branch polymer series 2

The concentrations of the polymers were kept at 20 mg/ml.

Figure 29.
Branch polymer series 3
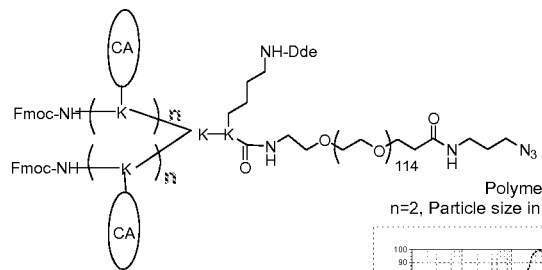
The concentrations of the polymers were kept at 20 mg/ml.
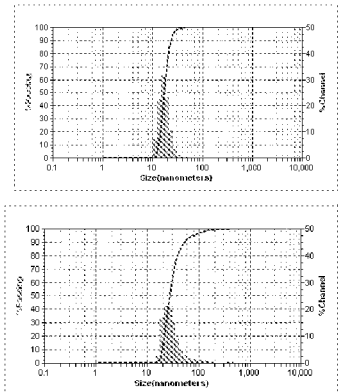
Polymer 28
n=2, Particle size in PBS: 16.98 nm
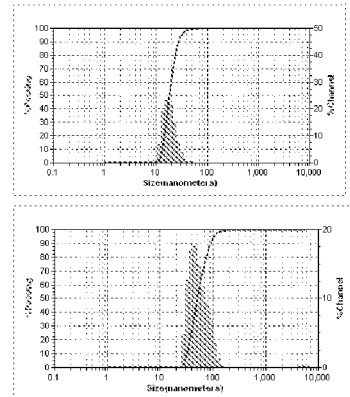
Polymer 29
n=3, Particle size in PBS: 18.19 nm
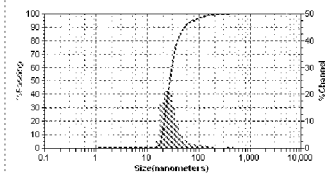
Polymer 30
n=4, Particle size in PBS: 27.55 nm
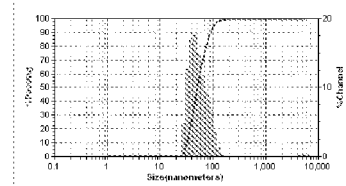
Polymer 31
n=5, Particle size in PBS: 50.20 nm Figure 30.
Branch polymer series 4
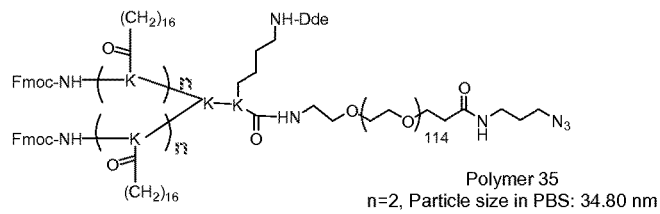
The concentrations of the polymers were kept at 20 mg/ml.
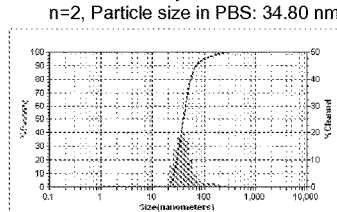
Polymer 35
n=2, Particle size in PBS: 34.80 nm
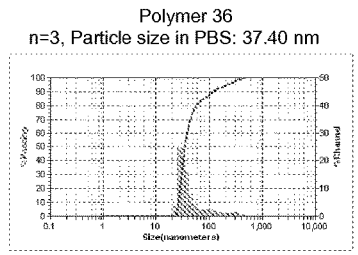
Polymer 36
n=3, Particle size in PBS: 37.40 nm
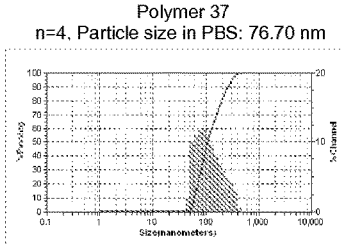
Polymer 37
n=4, Particle size in PBS: 76.70 nm
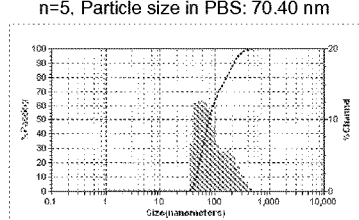
Polymer 38
n=5, Particle size in PBS: 70.40 nm Figure 31.
Before PEG grafting:
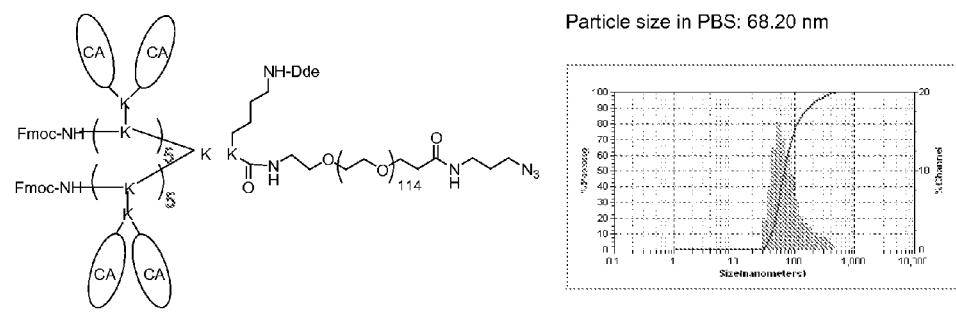
After PEG grafting:
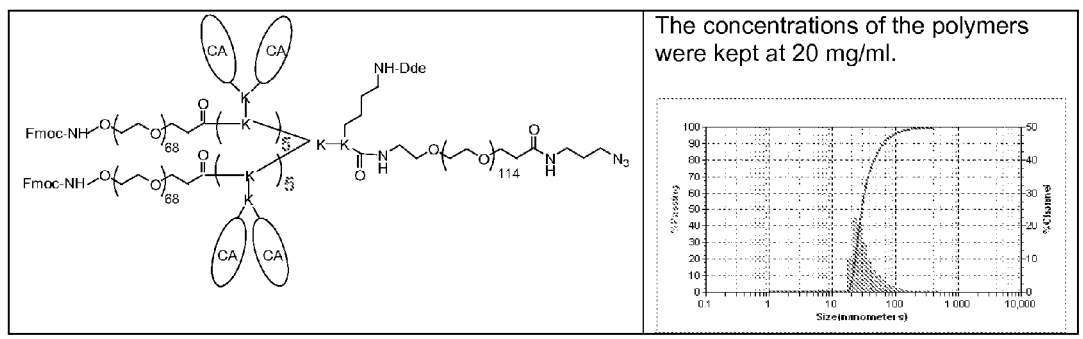

Figure 36.
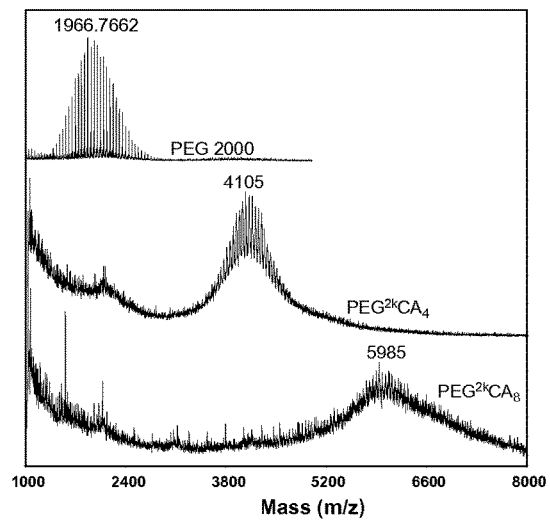
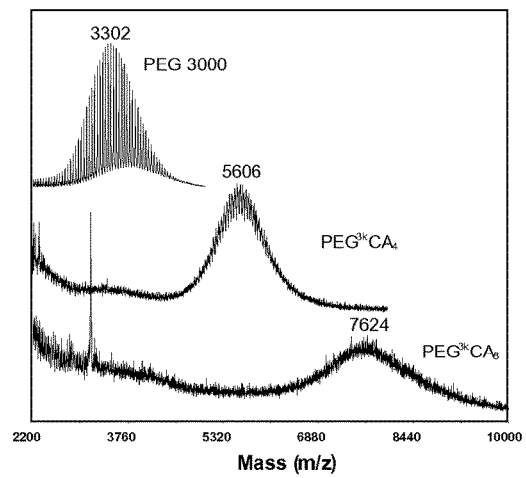
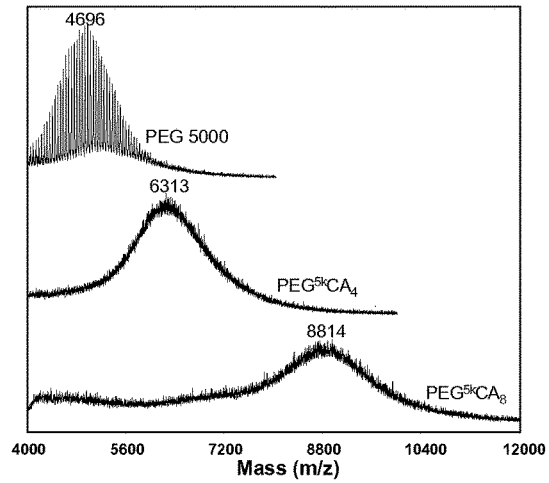

Branched polymers P-1 n=2,3,4,5

P-1 (n=2, 3, 4, 5)

Figure 43.
(A)
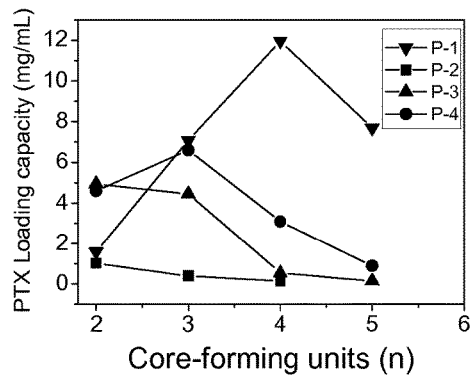
(B)
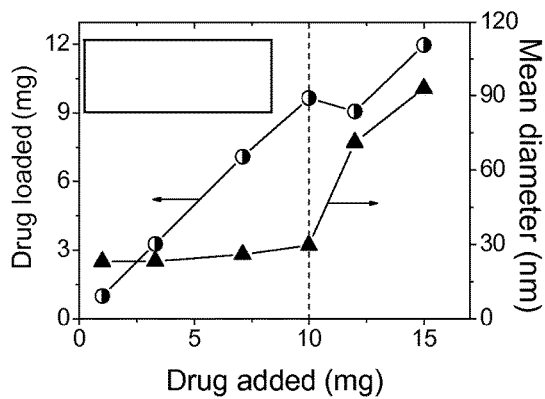
(C)
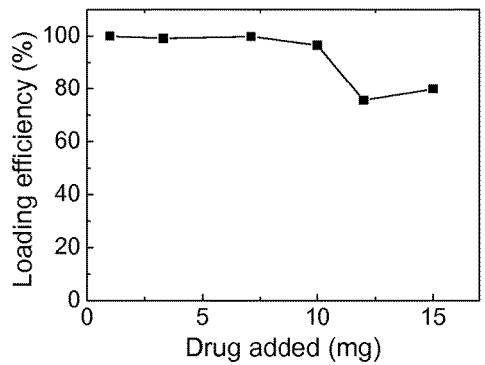

Branch Polymer Series 2

Polymers 25, 26 and 27 with n=2, 3, 4, respectively

Branch Polymer Series 3

Polymers 28, 29, 30 and 31
with n=2,3 ,4 and 5 respectively

Branch Polymer Series 4

Polymers 35, 36, 37 and 38 with n=2,3,4 and 5 respectively

HS-PEG⁵⁰⁰⁰-CA₈ n=2,3,4 and 5

NANOCARRIERS FOR DRUG DELIVERY

CROSS-REFERENCES TO RELATED APPLICATIONS

This application is the U.S. National Stage entry of International Application No. PCT/US2009/057852, filed Sep. 22, 2009, which claims benefit of priority to U.S. Provisional Patent Application No. 61/099,272, filed Sep. 23, 2008, which are incorporated in their entirety herein for all purposes.

STATEMENT AS TO RIGHTS TO INVENTIONS MADE UNDER FEDERALLY SPONSORED RESEARCH AND DEVELOPMENT

This invention was made with Government support under Grant No. R01CA115483, awarded by the National Cancer Institute and the National Institutes of Health. The Government has certain rights in this invention.

BACKGROUND OF THE INVENTION

Paclitaxel (Taxol®) is a standard and effective chemotherapeutic agent for many cancer types, e.g. ovarian cancer, breast cancer, small cell lung cancer, and non-small cell lung cancer. Because paclitaxel is very insoluble in water, formulation of this drug requires Cremophor EL which causes significant side effects such as allergic reactions. Patients receiving Paclitaxel (PTX) require premedication with histamine blockers and steroid.

Abraxane® is a newer formulation of paclitaxel that has less of these side effects and it is among the first nanotherapeutic agents approved by the FDA. It consists of human serum albumin nanoparticles (~130 nm) loaded with paclitaxel. However, because of its relatively large size, it is unlikely that Abraxane can penetrate deep into the tumor mass. In addition, these relatively large nanoparticles have a propensity to be trapped in the liver and the reticuloendothelial system (RES). Doxil® or liposomal doxorubicin, another nanotherapeutic drug, has similar dimensions as Abraxane but is coated by polyethylene glycol (PEG). Compared to the parent doxorubicin free drug, Doxil has less cardiotoxicity. Similar to Abraxane, it is doubtful that Doxil can penetrate deep into the tumor mass.

Although these two nanotherapeutics exhibit better clinical toxicity profile, their anti-tumor effects are only marginally better than the original drug formulation. Amphiphilic block copolymers can form micelles on the nanoscale and have been applied in the development of drug delivery systems. Amphiphilic block copolymers can form hydrotropic micelles in nanoscale (<100 nm) and have been applied in the development of drug delivery systems. However, most of these micelles are non-biodegradable and tend to be trapped in the RES. Furthermore, these micelles often consist of linear hydrophobic polymers that form a loose core under aqueous environment, leading to instability and low drug loading capacity. There is a need to develop smaller (20-80 nm) stealth and biocompatible micelles as effective nanocarriers for anti-cancer drug delivery in vivo.

We have recently developed several novel nanocarriers for PTX or other hydrophobic drugs. These novel nanocarriers, comprising of PEG and oligo-cholic acids, can self-assemble under aqueous conditions to form core-shell (cholane-PEG) structures that can carry PTX in the hydrophobic interior. These amphiphilic drug-loaded nanoparticles are expected to be therapeutic by themselves with improved clinical toxicity profile. More importantly, when decorated with cancer cell surface targeting ligands and/or tumor blood vessel ligands, these nanocarriers will be able to deliver toxic therapeutic agents to the tumor sites. The final size of the nanocarriers (10 to 100 nm) is tunable by using various, or a combination of, different cholane-PEG preparations. The nanocarriers and their components, PEG and cholic acid, are all non-toxic and fully biocompatible.

PEG has been widely used in various biomedical applications because it is inert and biocompatible. There are a number of PEG-modified protein drugs approved by the FDA, e.g., PEGylated asparagines. PEGylation not only improves the pharmacokinetic properties but also lowers the immunogenicity of protein drugs. Small molecule or peptide drugs, when PEGylated, have been shown to increase their circulation time and delay their metabolism. PEG grafted on the surface of nanoparticles lowers the in vivo extravasation of these particles into normal tissues and reticuloendothelial system (RES). In in vivo imaging studies, PEG modification has been shown to reduce aggregation and toxicities of inorganic nanoparticles, such as quantum dots and magnetic nanoparticles. Bile acids are natural surfactants biosynthesized in the liver of mammals as emulsifiers in the digestion of fats. Cholic acid, a primary component of bile acid, possesses facial amphiphilic structure: a rigid steroid scaffold with four hydrophilic groups on one surface and hydrophobic methyl groups on the other surface of the scaffold. Cholic acid salt form cigar shape micelles in water, and its synthetic oligomers in water forms unimolecular micelle with a hydrophobic pocket, which can thermodynamically seclude hydrophobic molecules. However, the application of the oligo-cholic acid in drug delivery is limited by its poor solubility and low drug loading capacity. We have previously prepared a star-shaped cholic acid-PEG compound with four PEG chains grafted on a single cholic acid core. This compound can form spherical micelles in aqueous solution, and it can be used as a carrier in drug delivery. However, the critical micellation concentration (cmc) of this compound is relative high due to the dominant hydrophilic PEG component compared to the single cholane unit, and the resulting micelles prepared under aqueous condition is relatively big (>200 nm in diameter).

Surprisingly, the present invention meets this, and other needs, by providing a much smaller and more stable nanocarrier with core-shell structure prepared from cholanes on PEG.

BRIEF SUMMARY OF THE INVENTION

In one embodiment, the present invention provides a nanocarrier having an interior and an exterior, the nanocarrier comprising at least one conjugate, wherein each conjugate includes a polyethylene glycol (PEG) polymer. Each conjugate also includes at least two amphiphilic compounds having both a hydrophilic face and a hydrophobic face. In addition, each conjugate includes an oligomer, wherein at least 2 of the amphiphilic compounds are covalently attached to the oligomer which is covalently attached to the PEG. The nanocarrier is such that each conjugate self-assembles in an aqueous solvent to form the nanocarrier such that a hydrophobic pocket is formed in the interior of the nanocarrier by the orientation of the hydrophobic face of each amphiphilic compound towards each other, and wherein the PEG of each conjugate self-assembles on the exterior of the nanocarrier.

In a second embodiment, the present invention provides a method of treating a disease by administering to a subject in need of such treatment, a therapeutically effective amount of a nanocarrier of the present invention.

In a third embodiment, the present invention provides a method of imaging, comprising administering to a subject to be imaged, an effective amount of a nanocarrier of the present invention, wherein the nanocarrier further comprises an imaging agent.

BRIEF DESCRIPTION OF THE DRAWINGS

FIG. 29 shows the particle size for nanocarriers of the branched series 3 architecture versus the number of cholic acid groups.

FIG. 30 shows the particle size for nanocarriers of the branched series 4 architecture versus the number of heptadecanoic acid groups.

FIG. 31 shows the size of the nanocarrier before and after PEG grafting.

FIG. 36 shows the MALDI-TOF MS analysis of the telodendrimers and the starting material, linear PEG, demonstrating the well-defined structure of the telodendrimers in view of the close molecular weight of dendritic tetramer of CA (1961 Dalton) and octamer of CA (4031 Dalton), respectively.

FIG. 38A shows in vivo NIRF imaging of the intraperitoneal SKOV-3 tumor bearing mice at different time points after i.p. injection of DiD-PTX-NPs. FIG. 38B shows localization of DiD-PTX-NPs on tumors. The mice were sacrificed at 72 h post injection, and the abdominal cavity was exposed to scan with Kodak imaging station.

FIG. 40A shows bioluminescence emitted by luciferase-expressing SKOV3-luc cancer cells at different time points after treatment. Peritoneal SKOV3-luc tumors bearing mice received total five intraperitoneal injection of Taxol®, Abraxane® and PTX-PEG$^{5000}$-CA$_8$ NPs on day 0, 4, 8, 12 and 16. Control groups received PBS only. Signal from the entire abdominal region of each mouse were quantified, and background was subtracted by measuring same sized ROIs in areas without light emission. FIG. 40B shows survival of mice in different treatment groups. Open circle represents censored data point secondary to a death during anesthesia (i.e., not tumor-related).

FIG. 43 shows the paclitaxel loading capacity of micelles as the number of core-forming units increases in branched polymer series 1 (P-1), branched polymer series 2 (P-2), branched polymer series 3 (P-3) and branched polymer series 4 (P-4) (43A); amount of paclitaxel loaded in polymer 23 and the corresponding mean diameter of polymer 23 loaded with paclitaxel, as the concentration of drug increases (43B); and loading efficiency of polymer 23 micelle as the drug concentration increases in solution (43C). The volume of the final micelle solution was kept at 1 mL and the final concentration of the polymers was 20 mg/mL for all the drug loading tests.

FIG. 47A shows in vivo NIR optical images of SKOV-3 tumor bearing mouse obtained with Kodak imaging system at different time points after i.v. injection of micelles 24 loaded with both PTX and DiD (hydrophobic dye). FIG. 47B shows ex vivo NIR image of dissected organs and tumor was obtained at 24 h after injection. Quantitative fluorescence intensities of tumor and organs from ex vivo images.

DETAILED DESCRIPTION OF THE INVENTION

I. General

Figure 1:
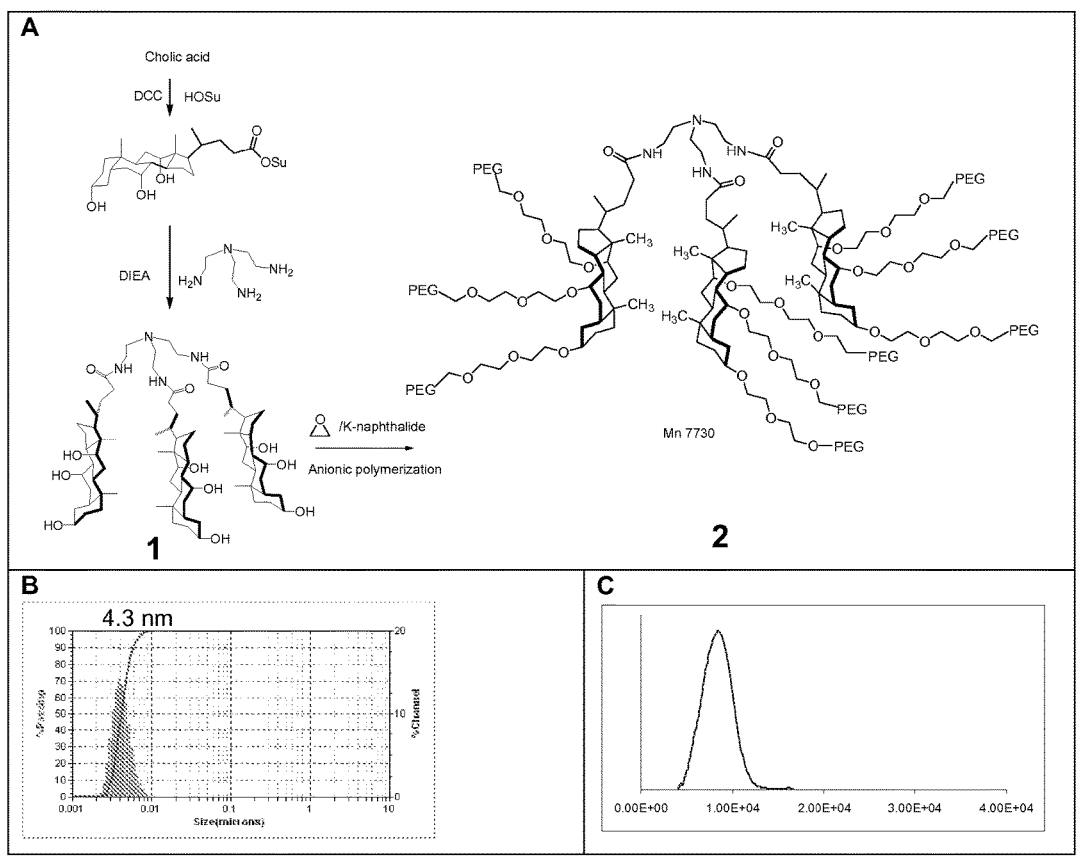
FIG. 1 shows (A) Synthetic scheme of $CA_3$ (compound 1) and $CA_3$-$PEG_9$ (polymer 2), (B) Particle size analysis shows that the mean diameter of the nanoparticle formed from polymer 2 in water was 4.3 nm, and (C) GPC curve of molecular weight analysis of polymer 2.

The present invention provides nanocarriers that have a hydrophobic interior and a hydrophilic exterior permitting the nanocarriers to deliver drugs having low water solubility. The nanocarriers are formed by the aggregation of conjugates into micelles. The conjugates of the present invention can adopt a variety of architectures, including linear, branched and telodendrimer. The hydrophobic core of the nanocarriers can be provided by cholic acid, which has a hydrophobic face and a hydrophilic face. Typically, several cholic acid groups are used to sequester the drug in the nanocarrier. The hydrophilicity of the nanocarriers is provided by a polyethyleneglycol polymer chain that encapsulates the nanocarrier and forms a micelle through the aggregation of the conjugates. The cholic acid and the PEG are connected by an oligomer that can contain a variety of acid repeats units. Typically, the oligomer comprises a diamino carboxylic acid, lysine. The nanocarriers of the present invention can also be functionalized with an optical probe, a radionuclide, and a metal chelate, as well as the hydrophobic drug.

II. Definitions

As used herein, the term "amphiphilic compound" refers to a compound having both hydrophobic portions and hydrophilic portions. For example, the amphiphilic compounds of the present invention can have one hydrophilic face of the compound and one hydrophobic face of the compound. Amphiphilic compounds useful in the present invention include, but are not limited to, cholic acid, and cholic acid analogs such as allocholic acid, pythocholic acid, avicholic acid, deoxycholic acid, chenodeoxycholic acid, etc. (see Current Science 2004, 87(12), 1666, incorporated in its entirety herein).

As used herein, the term "monomer unit" refers to a diamino carboxylic acid, a dihydroxy carboxylic acid and a hydroxylamino carboxylic acid. Examples of diamino carboxylic acid groups of the present invention include, but are not limited to, 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl)butyric acid and 5-amino-2-(3-aminopropyl)pentanoic acid. Examples of dihydroxy carboxylic acid groups of the present invention include, but are not limited to, glyceric acid, 2,4-dihydroxybutyric acid, glyceric acid, 2,4-dihydroxybutyric acid, 2,2-Bis(hydroxymethyl)propionic acid and 2,2-Bis(hydroxymethyl)butyric acid. Examples of hydroxylamino carboxylic acids include, but are not limited to, serine and homoserine. One of skill in the art will appreciate that other monomer units are useful in the present invention.

As used herein, the term "spacer monomer unit" refers to a chemical group that connects the monomer units to one another. Examples of the spacer monomer unit include, but are not limited to, ethylene glycol oligomers having 1-3 oxy-ethylene groups. One of skill in the art will appreciate that other spacer monomer units are useful in the present invention.

As used herein, the term "hydrophobic drug" refers to any drug that repels water. Drugs useful in the present invention include, but are not limited to, paclitaxel, doxorubicin, etoposide, irinotecan, SN-38, cyclosporin A, podophyllotoxin, Carmustine, Amphotericin, Ixabepilone, Patupilone (epothelone class), rapamycin and platinum drugs. The hydrophobic drug of the present invention also includes prodrug forms of the drugs listed above. One of skill in the art will appreciate that other drugs are useful in the present invention.

As used herein, the term "binding ligand" refers to a chemical or biological agent that is capable of binding to a target macromolecule, such as, cell-surface receptors of normal cells, cancer cells and endothelial cells, as well as acellular components in the extracellular matrix and the bony matrix, and surface receptors of infectious agents (virus, fungus, bacteria and parasite, among others). Binding ligands useful in the present invention include, but are not limited to, LLP2A (binding to the α4β1 integrin ligand), LXY1 and LXY3 (binding to the α3β1 integrin ligand), RGD peptide (binding to the α5β1 and αvβ3 integrin ligands), and biphosphonates (bone seeking molecule). One of skill in the art will appreciate that other binding ligands are useful in the present invention.

As used herein, the term "imaging agent" refers to chemicals that allow body organs, tissue or systems to be imaged. Exemplary imaging agents include paramagnetic agents, optical probes, and radionuclides.

As used herein, the term "paramagnetic agent" refers to imaging agents that are magnetic under an externally applied field. Examples of paramagnetic agents include, but are not limited to, iron particles including nanoparticles.

As used herein, the term "optical probe" refers to a fluorescent compound that can be detected by excitation at one wavelength of radiation and detection at a second, different, wavelength of radiation. Optical probes useful in the present invention include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots.

As used herein, the term "radionuclide" refers to chemical elements that undergo radioactive decay. Radionuclides useful in the present invention include, but are not limited to, $^{3}$H, $^{11}$C, $^{13}$N, $^{18}$F, $^{19}$F, $^{60}$Co, $^{64}$Cu, $^{67}$Cu, $^{68}$Ga, $^{82}$Rb, $^{90}$Sr, $^{90}$Y, $^{99}$Tc, $^{99m}$Tc, $^{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am.

As used herein, the term "metal chelate" refers to a compound or agent that chelates a metal ion. For example, metal chelates useful in the present invention include, but are not limited to, 1,4,8,11-tetraazacyclododecane-1,4,8,11-tetraacetic acid (TETA), 4,11-bis(carboxymethyl)-1,4,8,11-tetraazabicyclo[6.6.2]hexadecane (CB-TE2A), diethylenetriaminepentaacetice acid (DTPA) and 1,4,7,10-tetraazacyclodecanetetraacetic acid (DOTA).

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, "administering" refers to oral administration, administration as a suppository, topical contact, parenteral, intravenous, intraperitoneal, intramuscular, intralesional, intranasal or subcutaneous administration, intrathecal administration, intra-lymphatic, inhalation of microdroplets, or the implantation of a slow-release device e.g., a mini-osmotic pump, to the subject.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Reming-*

*ton: The Science and Practice of Pharmacy,* 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "secluded/sequestered" refers to the hydrophobic drug being on the hydrophobic interior of the nanocarrier and not exposed to a hydrophilic environment outside of the nanocarrier.

III. Nanocarriers

The present invention provides nanocarriers that form micelles where each individual nanocarrier is a micelle having a hydrophobic interior and a hydrophilic exterior. The hydrophobic region of the nanocarrier is capable of sequestering hydrophobic drugs. The nanocarriers are formed by the aggregation of conjugates having hydrophobic regions formed from amphiphilic compounds and hydrophilic regions, such as polyethylene glycol (PEG) polymers. The PEG is of sufficient size to encapsulate the hydrophobic region of the conjugate so that the conjugate can be dissolved in water and self-assemble to form the nanocarrier micelle, facilitating the administration to a subject of a hydrophobic drug or an imaging agent.

In some embodiments, the present invention provides nanocarriers capable of sequestering a hydrophobic drug. The nanocarrier of the present invention has an interior and an exterior, the nanocarrier comprising at least one conjugate, wherein each conjugate includes a polyethylene glycol (PEG) polymer. Each conjugate also includes at least two amphiphilic compounds having both a hydrophilic face and a hydrophobic face. In addition, each conjugate includes an oligomer, wherein at least 2 of the amphiphilic compounds are covalently attached to the oligomer which is covalently attached to the PEG. The nanocarrier is such that each conjugate self-assembles in an aqueous solvent to form the nanocarrier such that a hydrophobic pocket is formed in the interior of the nanocarrier by the orientation of the hydrophobic face of each amphiphilic compound towards each other, and wherein the PEG of each conjugate self-assembles on the exterior of the nanocarrier.

Polyethylene glycol (PEG) polymers of any size and architecture are useful in the nanocarriers of the present invention. In some embodiments, the PEG is from 1-100 kDa. In other embodiments, the PEG is from 1-10 kDa. In some other embodiments, the PEG is about 3 kDa. In still other embodiments, additional PEG polymers are linked to the amphiphilic compounds. For example, when the amphiphilic compound is cholic acid, up to 3 PEG polymers are linked to each cholic acid. The PEG polymers linked to the amphiphilic compounds are from 200-10,000 Da in size. In yet other embodiments, the PEG polymers linked to the amphiphilic compounds are from 1-5 kDa in size. One of skill in the art will appreciate that other PEG polymers and other hydrophilic polymers are useful in the present invention.

The conjugates of the present invention also include at least two amphiphilic compounds that are the same or different. Amphiphilic compounds useful in the conjugates of the present invention are those having both a hydrophilic face and a hydrophobic face. In addition, each amphiphilic compound is linked to a monomer unit, which is itself linked another monomer unit and/or to the PEG polymer. In some embodiments, the amphiphilic compounds can each independently be cholic acid, allocholic acid, pythocholic acid, avicholic acid, deoxycholic acid, or chenodeoxycholic acid. One of skill in the art will appreciate that other amphiphilic compounds are useful in the present invention.

The conjugates of the present invention also include a plurality of monomer units. In some embodiments, the plurality of monomer units are linked together to form an oligomer. The oligomer is covalently attached to the PEG and to the amphiphilic compounds. The oligomer can adopt any of several architectures, such as a linear architecture, a branched architecture or a telodendritic architecture.

In some embodiments, the nanocarrier includes a hydrophobic drug or an imaging agent, such that the hydrophobic drug or imaging agent is sequestered in the hydrophobic pocket of the nanocarrier. The hydrophobic drug can be any drug that repels water, as discussed within. The hydrophobic drug and the imaging agent can be sequestered in the hydrophobic pocket of the nanocarrier, or covalently attached to the conjugate. Imaging agents include paramagnetic agents, optical probes and radionuclides. Paramagnetic agents include iron particles, such as iron nanoparticles that are sequestered in the hydrophobic pocket of the nanocarrier.

In some other embodiments, the monomer units useful in the conjugates of the present invention can be a diamino carboxylic acid, a dihydroxy carboxylic acid, or a hydroxylamino carboxylic acid. In still other embodiments, the diamino carboxylic acid is an amino acid. Examples of diamino carboxylic acid groups of the present invention include, but are not limited to, 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl)butyric acid and 5-amino-2-(3-aminopropyl) pentanoic acid. Examples of dihydroxy carboxylic acid groups of the present invention include, but are not limited to, glyceric acid, 2,4-dihydroxybutyric acid, 2,2-Bis(hydroxymethyl)propionic acid, 2,2-Bis(hydroxymethyl)butyric acid, serine and threonine. Examples of hydroxylamino carboxylic acids include, but are not limited to, serine and homoserine.

In another embodiment, more than one type of monomer unit is used in the conjugates of the present invention to afford an acid copolymer. For example, the acid copolymer can have diamino carboxylic acid alternating with hydroxylamino carboxylic acid or with dihydroxy carboxylic acid.

In other embodiments, at least one of the monomer units is optionally linked to an optical probe, a radionuclide, a metal chelate or a drug. The drug can be a variety of hydrophilic or hydrophobic drugs, and is not limited to the hydrophobic drugs that are sequestered in the interior of the nanocarriers of the present invention.

Drugs that can be sequestered in the nanocarriers or linked to the conjugates of the present invention include, but are not limited to, cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present invention include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine.

Other drugs useful in the present invention also include radionuclides, such as $^{67}Cu$, $^{90}Y$, $^{123}I$, $^{125}I$, $^{177}Lu$, $^{188}Re$, $^{186}Re$ and $^{211}At$. In some embodiments, a radionuclide can act therapeutically as a drug and as an imaging agent.

Hydrophobic drugs useful in the nanocarrier of the present invention includes any drug having low water solubility. In some embodiments, the hydrophobic drug is paclitaxel, doxorubicin, etoposide, irinotecan, SN-38, camptothecin, cyclosporin A, podophyllotoxin, Carmustine, Amphotericin, Ixabepilone, Patupilone (epothelone class), rapamycin and platinum drugs. In some other embodiments, the drug can be paclitaxel, SN38, camptothecin, etoposide or doxorubicin. Prodrug forms are also useful in the present invention.

In some embodiments, the conjugate has formula I:

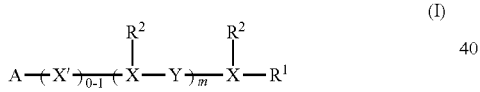
(I)

wherein A is the polyethyleneglycol (PEG) polymer of 1-100 kDa, wherein A is optionally linked to a binding ligand L. Each X is a monomer unit. X' is a monomer unit optionally linked to an optical probe, a radionuclide, a metal chelate or a drug. Each Y is a spacer monomer unit. Each $R^1$ is H, an optical probe, a radionuclide, a metal chelate, the hydrophobic drug or a polyethyleneglycol (PEG) polymer of 1-100 kDa optionally linked to an optical probe, a radionuclide, a metal chelate or a drug. Each $R^2$ is independently cholic acid or a monomer unit substituted with two cholic acid groups, wherein each cholic acid group is optionally substituted with 1-3 polyethyleneglycol (PEG) polymers each independently 200-10,000 Da in size. Subscript m is 2-20.

In other embodiments, the conjugate has formula Ia:

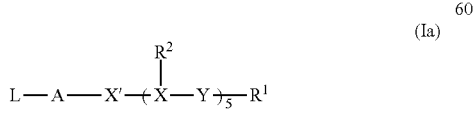
(Ia)

wherein A is a PEG polymer of 3 kDa. The monomer unit of X' is lysine. Each X is lysine. Each Y is

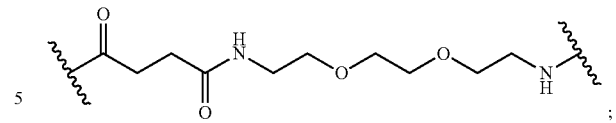

And each $R^2$ is lysine linked to two cholic acid groups.

In some other embodiments, the conjugate has formula II:

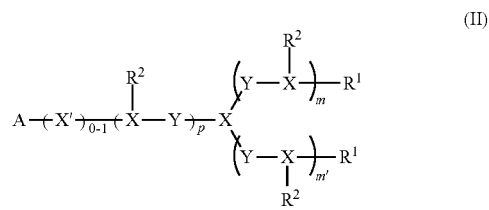
(II)

wherein A is the polyethyleneglycol (PEG) polymer of 1-100 kDa, wherein A is optionally linked to a binding ligand L. Each X is a monomer unit. X' is a monomer unit optionally linked to an optical probe, a radionuclide, a metal chelate or a drug. Each Y is a spacer monomer unit. Each $R^1$ is independently H, an optical probe, a radionuclide, a metal chelate, a drug or a polyethyleneglycol (PEG) polymer of 1-100 kDa optionally linked to an optical probe, a radionuclide, a metal chelate or the hydrophobic drug. Each $R^2$ is independently cholic acid or a monomer unit substituted with two cholic acid groups, wherein each cholic acid group is optionally substituted with 1-3 polyethyleneglycol (PEG) polymers each independently 200-10,000 Da in size. Each of subscript m and m' are independently 2-20. Subscript p is 0-10.

In still other embodiments, the conjugate has formula IIa:

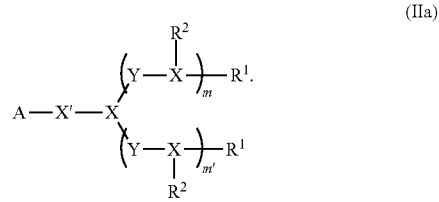
(IIa)

In yet other embodiments, each $R^2$ is cholic acid. In still yet other embodiments, each $R^2$ is a monomer unit each linked to two cholic acid groups.

In another embodiment, the conjugate has formula IIb:

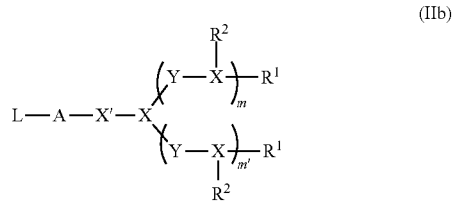
(IIb)

wherein A is a PEG polymer of 3 kDa. The monomer unit of X' is lysine. Each X is lysine. Each Y is

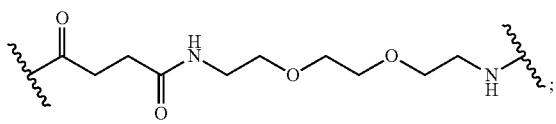

Each $R^2$ is a cholic acid. And subscripts m and m' are each 4.

In some embodiments, the conjugate has formula IIc:

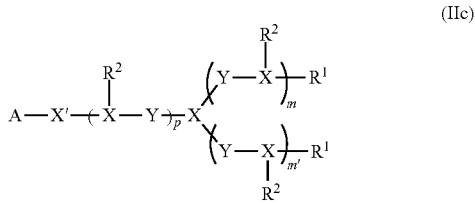

(IIc)

wherein subscript p is 1-10.

In other embodiments, the conjugate has formula III:

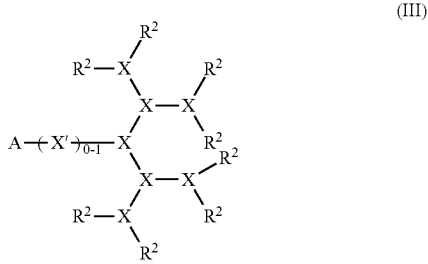

(III)

wherein A is the polyethyleneglycol (PEG) polymer of 1-100 kDa, wherein A is optionally linked to a binding ligand L. Each X is a monomer unit. X' is the monomer unit optionally linked to an optical probe, a radionuclide, a metal chelate or a drug. And each $R^2$ is cholic acid, wherein each cholic acid group is optionally substituted with 1-3 polyethyleneglycol (PEG) polymers each independently 200-10,000 Da in size.

In some other embodiments, the conjugate has formula IIIa:

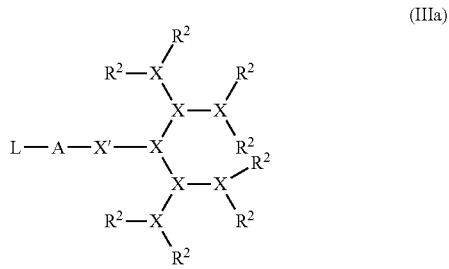

(IIIa)

wherein A is a PEG polymer of 5000 Da. The monomer unit of X' is lysine. Each X is lysine. And each $R^2$ is a cholic acid.

The conjugates of the present invention can be prepared by a variety of methods known to one of skill in the art.

IV. Method of Treating

The nanocarriers of the present invention can be used to treat any disease requiring the administration of a drug, such as by sequestering a hydrophobic drug in the interior of the nanocarrier, or by covalent attachment of a drug to a conjugate of the nanocarrier. The nanocarriers can also be used for imaging, by sequestering an imaging agent in the interior of the nanocarrier, or by attaching the imaging agent to a conjugate of the nanocarrier.

In some embodiments, the present invention provides a method of treating a disease, including administering to a subject in need of such treatment, a therapeutically effective amount of a nanocarrier of the present invention, wherein the nanocarrier includes a drug. The drug can be a covalently attached to a conjugate of the nanocarrier, or the drug can be a hydrophobic drug sequestered in the interior of the nanocarrier. In other embodiments, the nanocarrier also includes an imaging agent. The imaging agent can be a covalently attached to a conjugate of the nanocarrier, or the imaging agent can be sequestered in the interior of the nanocarrier. In some other embodiments, both a hydrophobic drug and an imaging agent are sequestered in the interior of the nanocarrier. In still other embodiments, both a drug and an imaging agent are covalently linked to a conjugate or conjugates of the nanocarrier. In yet other embodiments, the nanocarrier can also include a radionuclide.

The nanocarriers of the present invention can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers).

Other diseases that can be treated by the nanocarriers of the present invention include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome).

In addition, the nanocarriers of the present invention are useful for the treatment of infection by pathogens such as viruses, bacteria, fungi, and parasites. Other diseases can be treated using the nanocarriers of the present invention.

A. Formulations

The nanocarriers of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003, supra). Effective formulations include oral and nasal formulations, formulations for parenteral administration, and compositions formulated for with extended release.

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Pharmaceutical preparations useful in the present invention also include extended-release formulations. In some embodiments, extended-release formulations useful in the present invention are described in U.S. Pat. No. 6,699,508, which can be prepared according to U.S. Pat. No. 7,125,567, both patents incorporated herein by reference.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

In practicing the methods of the present invention, the pharmaceutical compositions can be used alone, or in combination with other therapeutic or diagnostic agents.

B. Administration

The nanocarriers of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

V. Method of Imaging

In some embodiments, the present invention provides a method of imaging, including administering to a subject to be imaged, an effective amount of a nanocarrier of the present invention, wherein the nanocarrier includes an imaging agent.

In other embodiments, the method of treating and the method of imaging are accomplished simultaneously using a nanocarrier having both a drug and an imaging agent.

VI. Examples

In the following discussion, the following nomenclature $PEG^{0000}\text{-}CA_n\text{-}PEG_{3n}$ is used to denote the chemical structure of the nanocarriers. The superscript numbers of the first PEG represent the size of the linear PEG used; CA represents cholic acid and "n" represent the number of cholic acid (CA) present in each unit of the nanocarrier; and the second PEG refers to PEG attached to the cholic acid (CA).

Example 1

Preparation of $CA_3\text{-}PEG_9$ (2)

Trimer of cholic acid ($CA_3$ or compound 1) was first prepared according to FIG. 1 using cholic acid NHS active ester and triaminoethyl amine as the starting materials. Small molecule trimer 1 was shown to have limited solubility in water. After filtration of the undissolved particles, it was observed to form unimolecular micelle structure with the size around 1 nm. After PEGylation via anionic polymerization of ethylene oxide, the molecular weight of $CA_3\text{-}PEG_9$ (polymer 2) increased to 7.7 KDa with a polydispersity index (PDI) of 1.04, indicating a very narrow distribution of molecular weight. The size of nanoparticles (nanocarrier 2) formed by polymer 2 in water was determined to be 4.3 nm in diameter with monodispersity.

Example 2

Preparation of Telodendrimer $PEG\text{-}CA_4$ (4)

Figure 2:
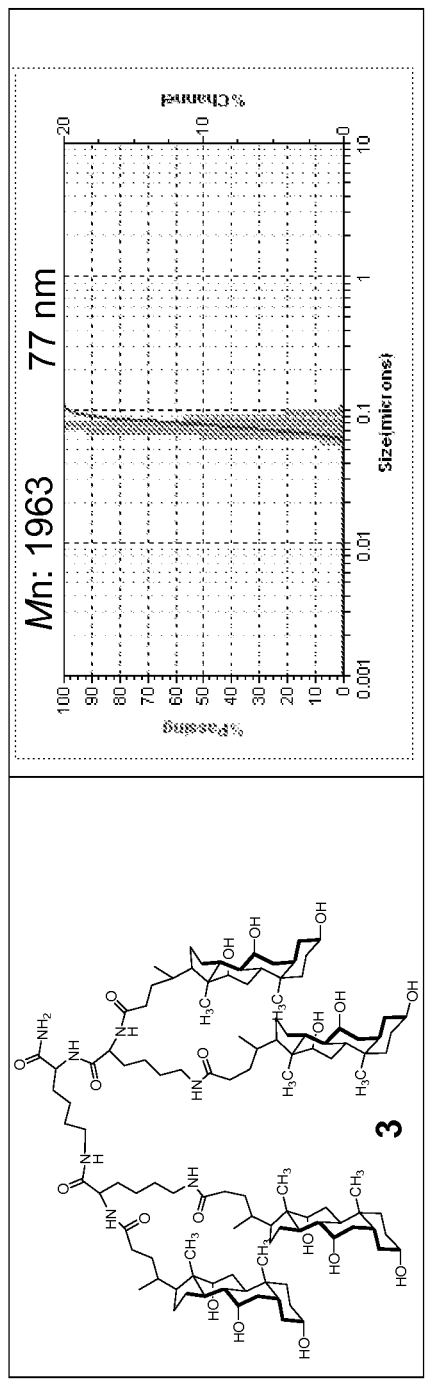
FIG. 2 shows the chemical structure and particle size of $CA_4$.

Solid Phase Synthesis of $CA_4$:

Tetramer of cholic acid (polymer 3) was synthesized on Rink resin via solid phase synthesis using lysine to make branches. The coupling reactions were performed according to the standard Fmoc peptide synthesis method, and the tetramer products were cleaved from resin by TFA in the presence of water and triisopropylsilane as scavengers. $CA_4$ has limited solubility in water, however, it was observed to self assemble into micelles at 77 nm in diameter (FIG. 2).

Figure 3:
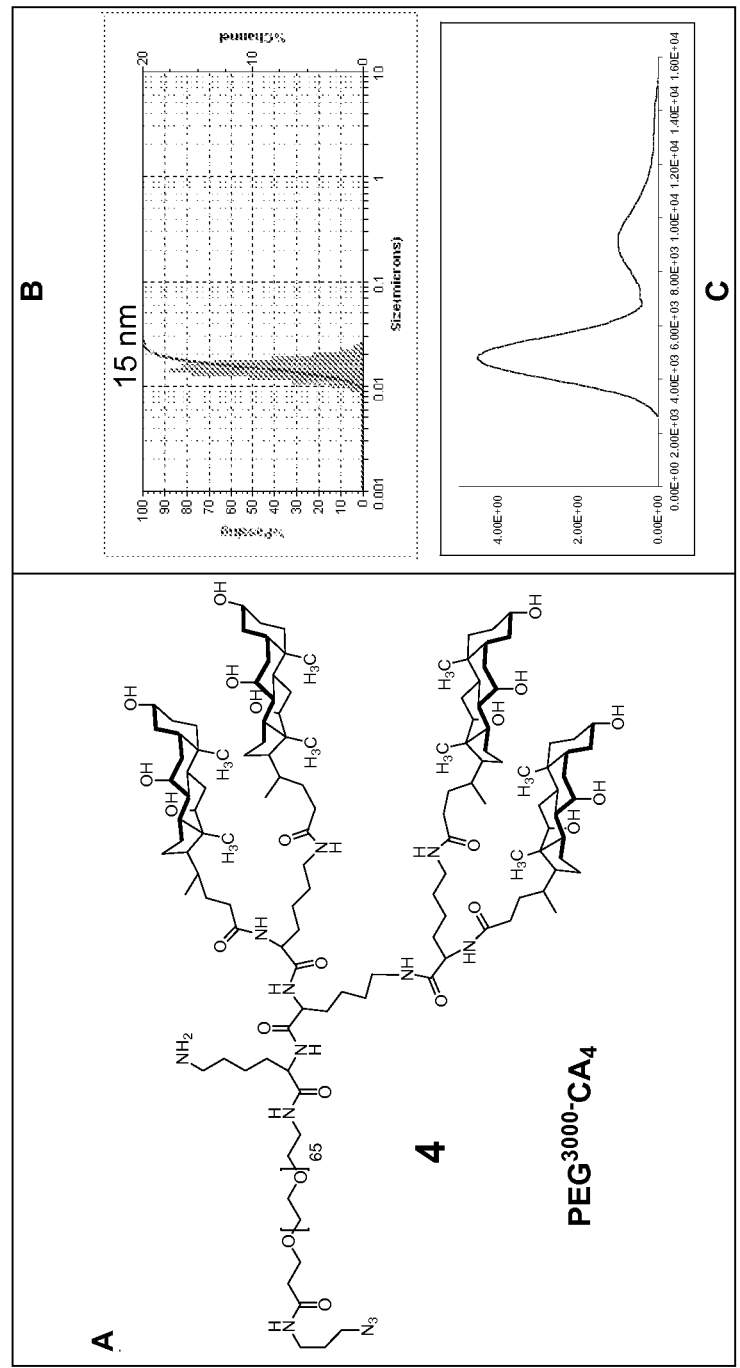
FIG. 3 shows (A) chemical structure, (B) particle size, and (C) molecular weight of $PEG^{3000}$-$CA_4$.
Figure 4:
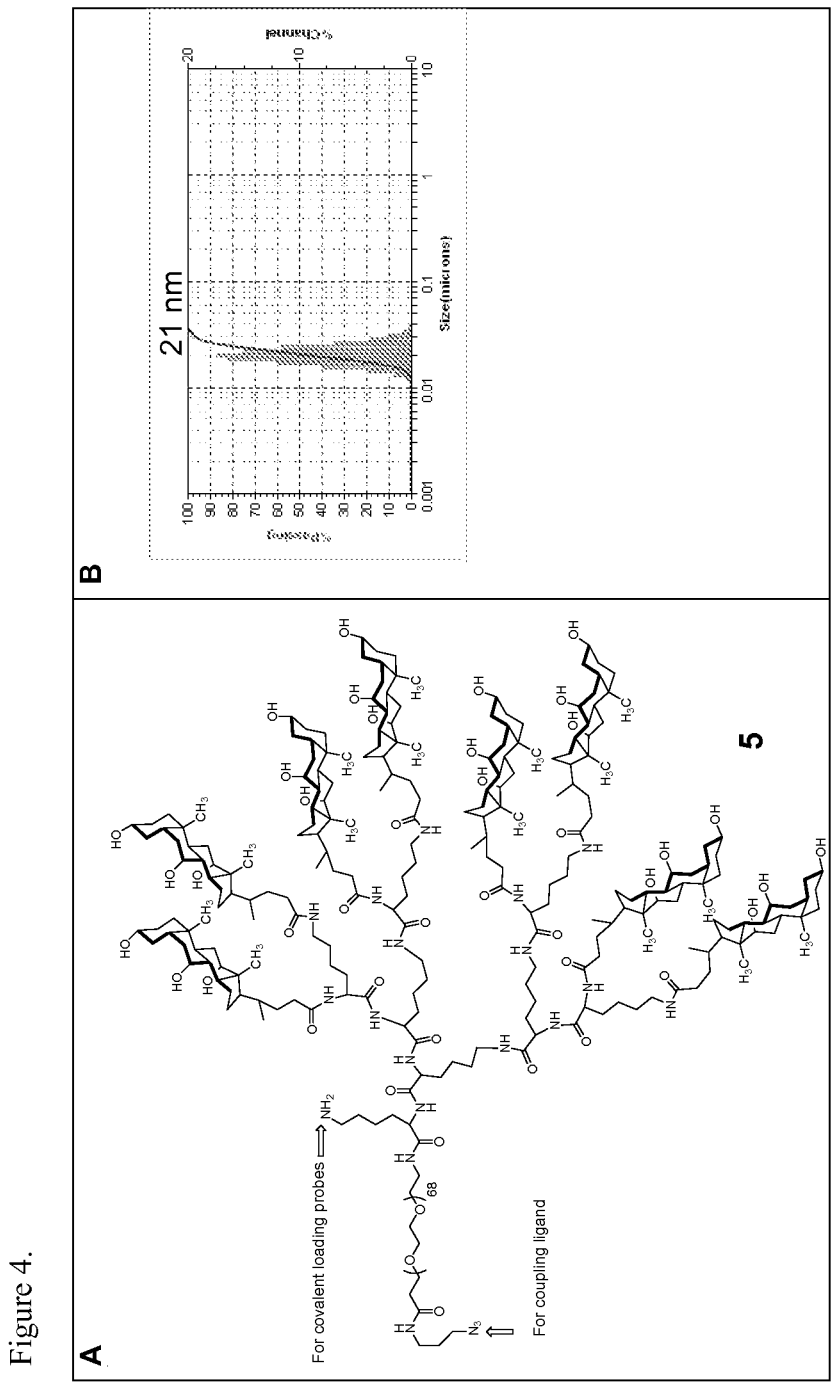
FIG. 4 shows (A) chemical structure and (B) particle size of $PEG^{3000}$-$CA_8$.
Figure 5:
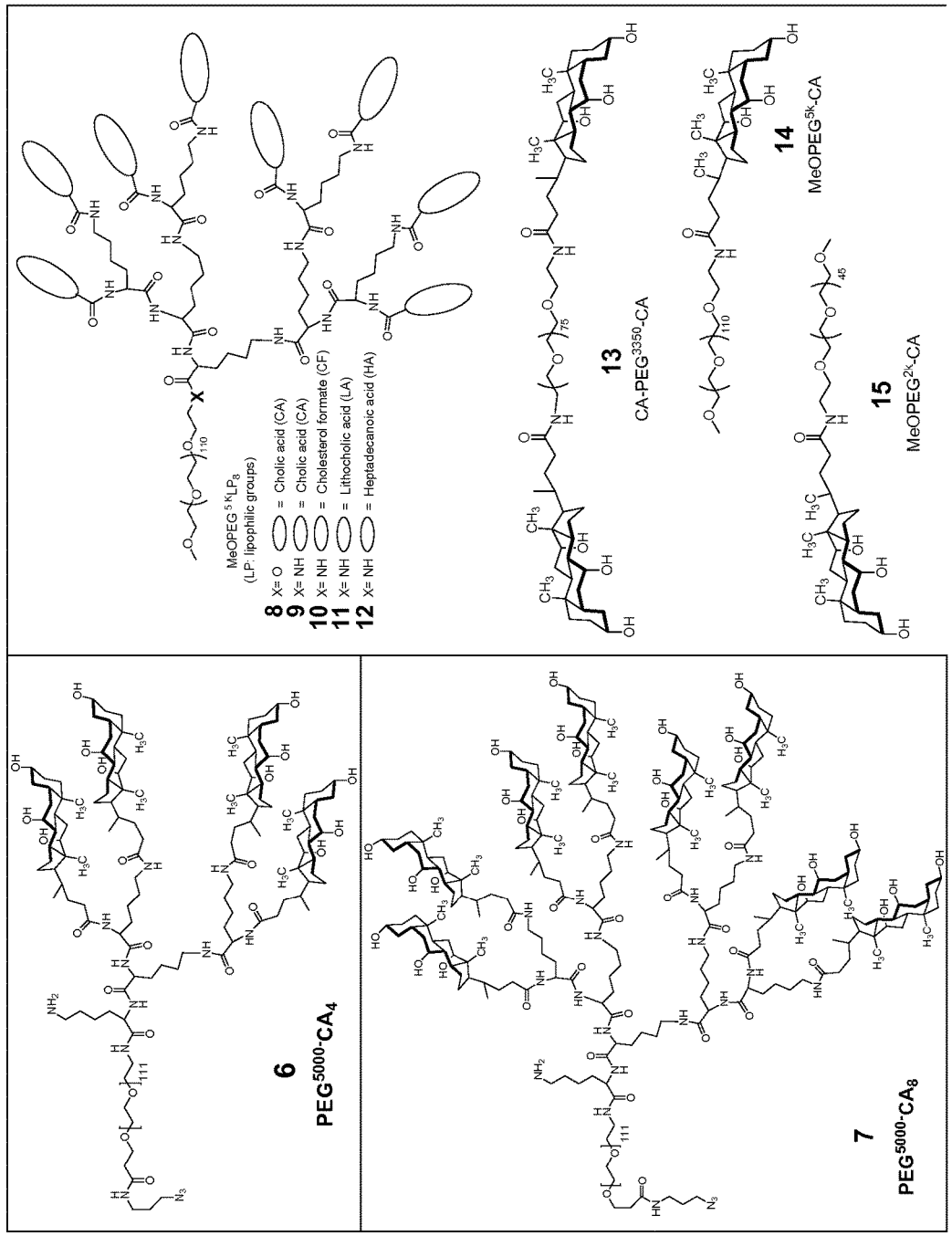
FIG. 5 shows the chemical structure of polymers 6-15 with PEG molecular weight of 5, 3.35 and 2 KDa.

Solution Phase Synthesis of Telodendritic Polymers:

Star shaped cholic acid tetrameric $PEG^{3000}\text{-}CA_4$ (polymer 4) was synthesized on a linear polyethylene glycol via solution phase condensation reactions (FIG. 3). The isolation of soluble PEGylated products was achieved by precipitation in cold ether. An azido group was coupled onto a carboxylic group of the Fmoc protected amino-PEG-COOH with a molecular weight of 3000 Da. After remove of the Fmoc with the treatment of 20% piperidine solution in DMF, (Fmoc)Lys(Boc)-OH was coupled onto the N terminal of PEG using DIC and HOBt as coupling reagents. Branched structure was achieved by the repeated coupling of (Fmoc)lys(Fmoc)-OH via Fmoc peptide synthesis. Cholic acid were introduced onto the amino groups of the branched lysine via cholic acid NHS ester to generate $PEG^{3000}\text{-}CA_4$, which were observed to self-assemble into nanoparticles with a narrow size distribution in 15 nm in diameter. The GPC study of $PEG^{3000}\text{-}CA_4$ also showed a narrow disperse in molecular weight with a mean molecular weight of 4.8 KDa plus a smaller peak at 9.2 KDa, which may be due to the aggregates of the amphiphilic polymer 4 (FIG. 3C). Star shaped cholic acid octamer (polymer 5) was synthesized on a linear polyethylene glycol via a third generation of dendritic oligolysine. It was observed to self-assemble into a bigger nanoparticle of 21 nm in diameter. This $PEG^{3000}\text{-}CA_8$ nanocarrier has shown promising loading capacity towards hydrophobic antitumor drugs, such as PTX, and will be discussed in detail below.

Example 3

Preparation of Telodendrimer $PEG^{3000}\text{-}CA_4\text{-}PEG_8$ (16)

Figure 6:
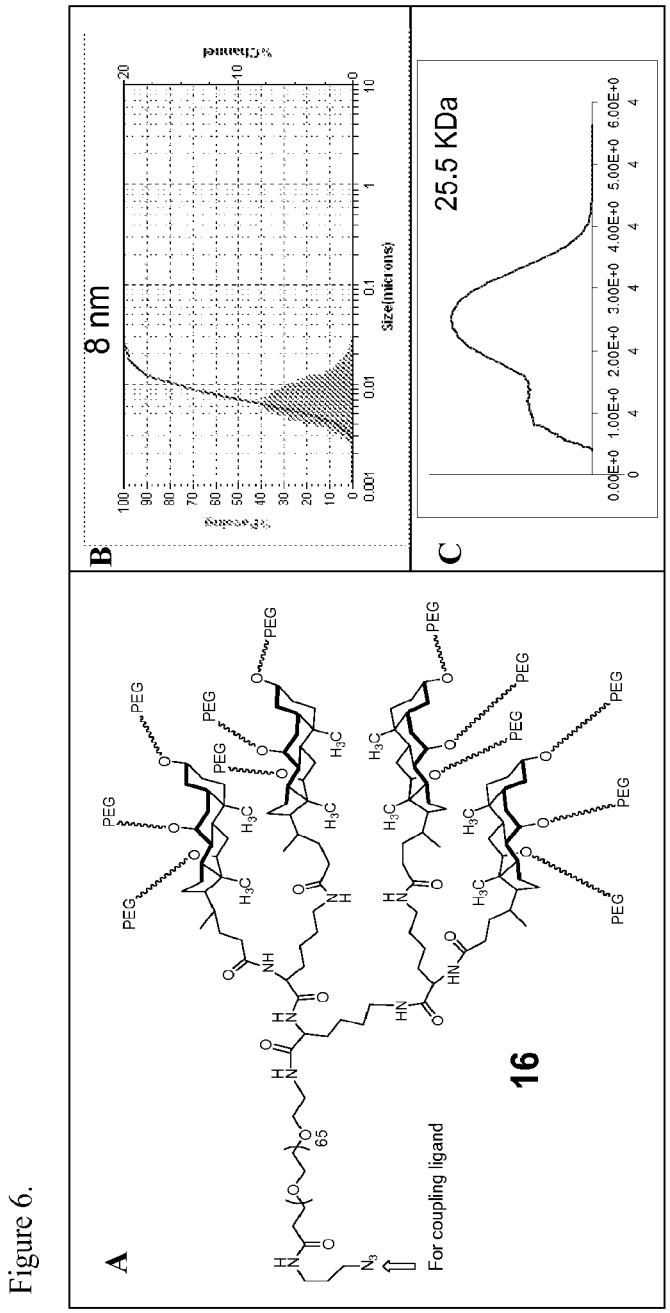
FIG. 6 shows (A) chemical structure, (B) particle size, and (C) molecular weight of $PEG^{3000}$-$CA_4$-$PEG_8$.
Figure 7:
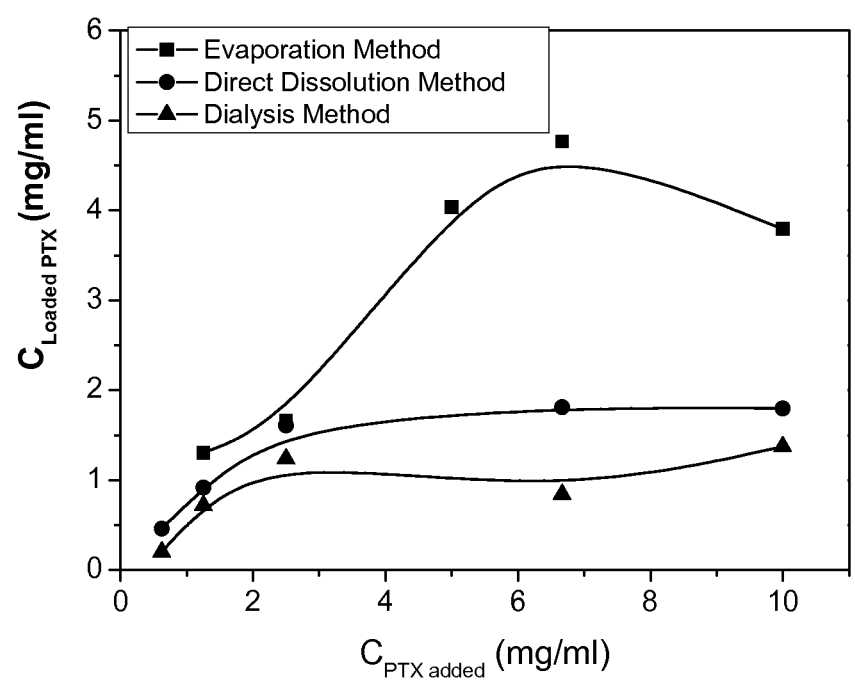
FIG. 7 shows the amount of PTX loaded in $PEG^{3000}$-$CA_8$ at different PTX concentrations using several methods. The concentration of polymer ($PEG^{3000}$-$CA_8$) was kept at 20 mg/mL for evaporation method and 10 mg/mL for dialysis method and dissolution method, respectively.
Figure 8:
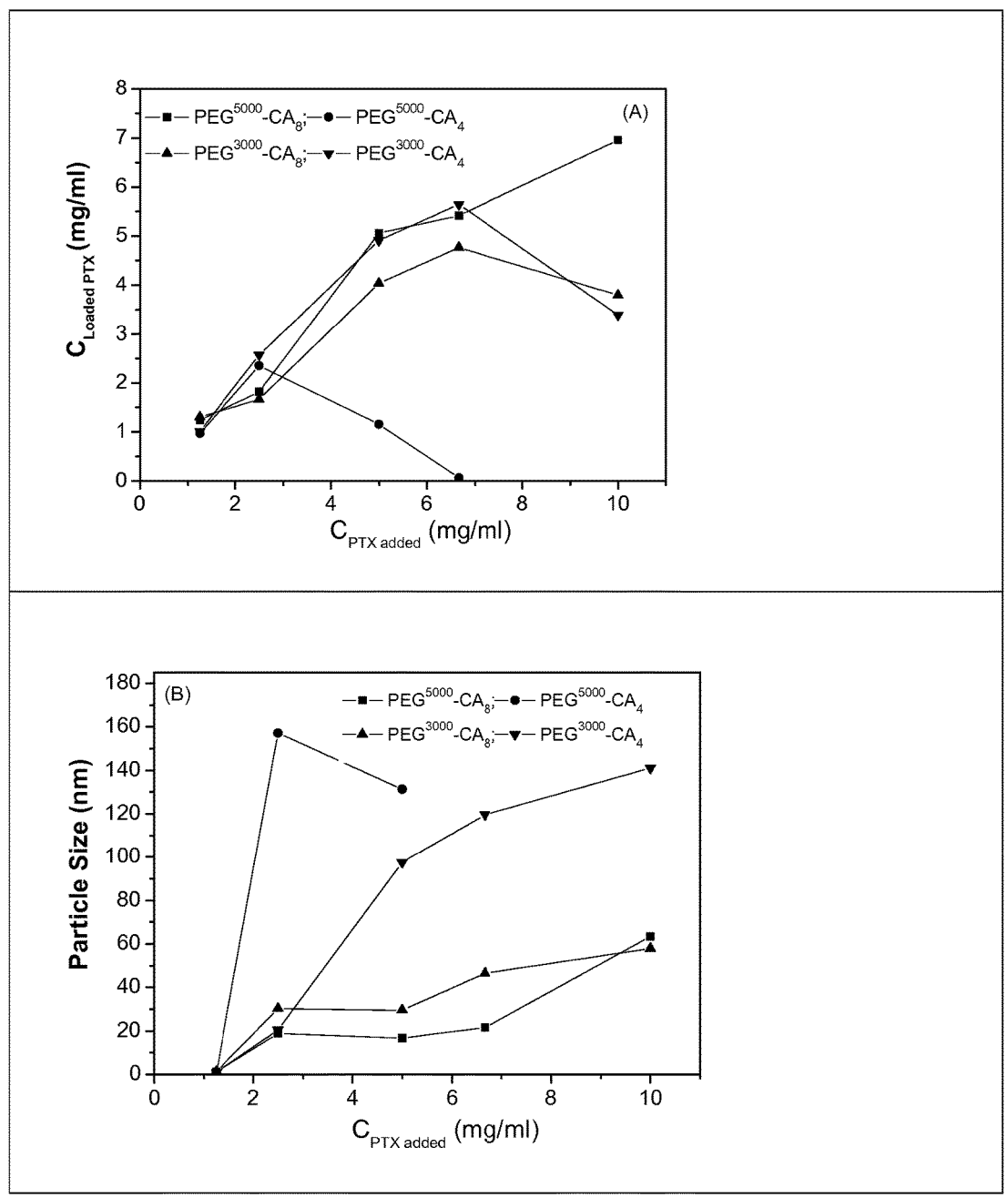
FIG. 8 shows the amount of PTX loaded in different polymers at different PTX concentrations (A) and the particle sizes of the drug loaded nanoparticles at the different concentrations of PTX added. The concentration of polymers was kept constant at 20 mg/mL.
Figure 9:
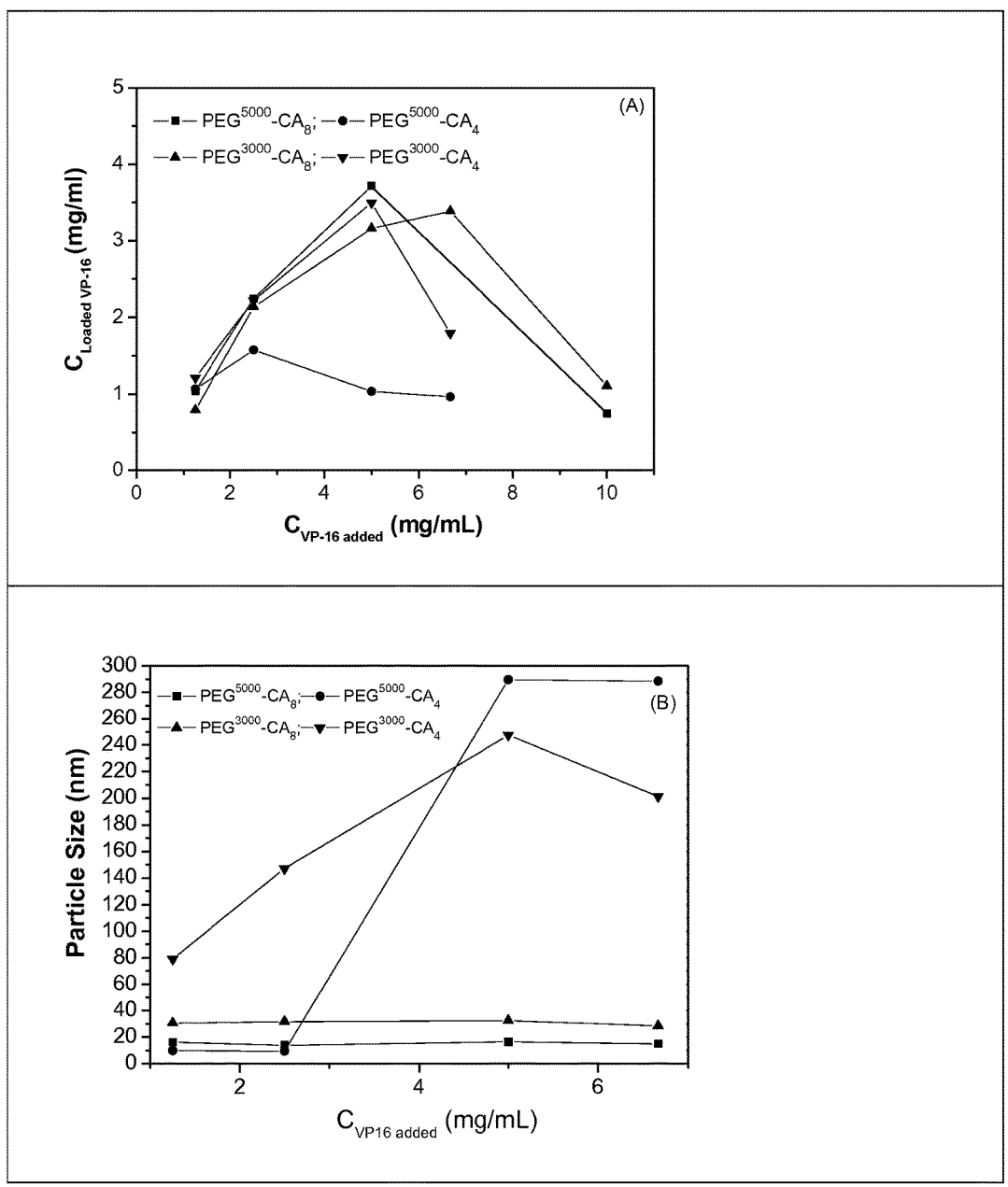
FIG. 9 shows the amount of etoposide (VP-16) loaded in different polymers at different etoposide concentrations (A) and the particle sizes of the drug loaded nanoparticles at the different concentrations of etoposide added. The concentration of polymers was kept constant at 20 mg/mL.

Synthesis of $PEG^{3000}\text{-}CA_4\text{-}PEG_8$ via anionic polymerization: Polymer 4 was synthesized on a linear polyethylene glycol as above. The molecule was further grafted with PEG chains via anionic polymerization of ethylene oxide starting from the twelve hydroxyl groups on the cholane units to make polymer 16 (FIG. 6). It is interesting that the micelles derived from the larger polymer 16 were smaller than those formed by the smaller polymer 4 (8 nm vs 15 nm, respectively). Presumably, the additional PEGs on each cholane unit limit the association of large number of polymer units into a large stable micelle. Not unexpectedly, drug loading studies showed that PTX loading capacity was relatively low (0.64 mg/mL), indicating that the hydrophobic pocket in this nanocarrier is rather small.

Example 4

Preparation of Linear Polymer Series (Polymers 17-20)

Figure 26:
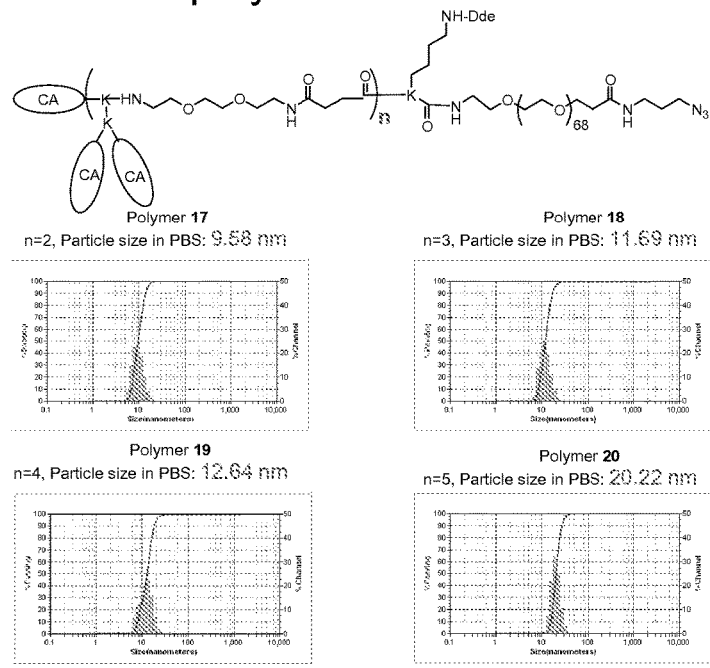
FIG. 26 shows the particle size for nanocarriers of the linear architecture versus the number of cholic acid groups.

The linear shaped cholic acid-PEG polymers linear series 1 were prepared via the same solution phase condensation reactions as in the preparation of telodendrimers. The isolation of soluble PEGylated products was achieved by precipitation in cold ether. Taking polymer 17 as an example for the synthetic procedure: An azido group was coupled onto a carboxylic group of the Fmoc protected amino-PEG-COOH with a molecular weight of 3000 Dalton using DIC/HOBt as coupling reagents. After the precipitation of azido PEG by cold ether, Fmoc groups were removed via the treatment with 20% piperidine solution in DMF, two steps coupling of (Fmoc)Lys(Boc)-OH were performed sequentially onto the N terminal of PEG via a Fmoc peptide chemistry using DIC and HOBt as coupling reagents. Boc protecting groups were removed by the treatment with 50% of TFA in DCM for 30 min and polymer was pricipated again with cold ether. In order to eliminate the stereo hindrance, a flexible spacer molecules (Fmoc-Ebes) was coupled onto the side chain of the lysine. After removal of the Fmoc group by the treatment of 20% piperidine in DMF, (Fmoc)Lys(Fmoc)-OH was coupled onto the side chain lysine using DIC/HOBt as coupling reagents. After remove of Fmoc protecting groups, cholic acid NHS active esters were coupled onto the side chain of lysines to introduce the pendant hydrophobic cholane blocks. The Fmoc protected N terminal is ready to couple fluorescence dye (such as Cy5.5) or radionuclides. A series of linear polymer with two cholic acids on each lysine unit have been prepared (FIG. 26) and the size of the micelles measured by DLS particle sizer increasing from 9.5 nm to 12.6 and to 20 nm with narrow polydispersities when the repeat units of lysine$(CA)_2$ increased from 2 to 3, 4 and 5.

Example 5

Preparation of Branched Polymer Series 1-4

Branched Polymer Series 1 and 4.

Figure 27:
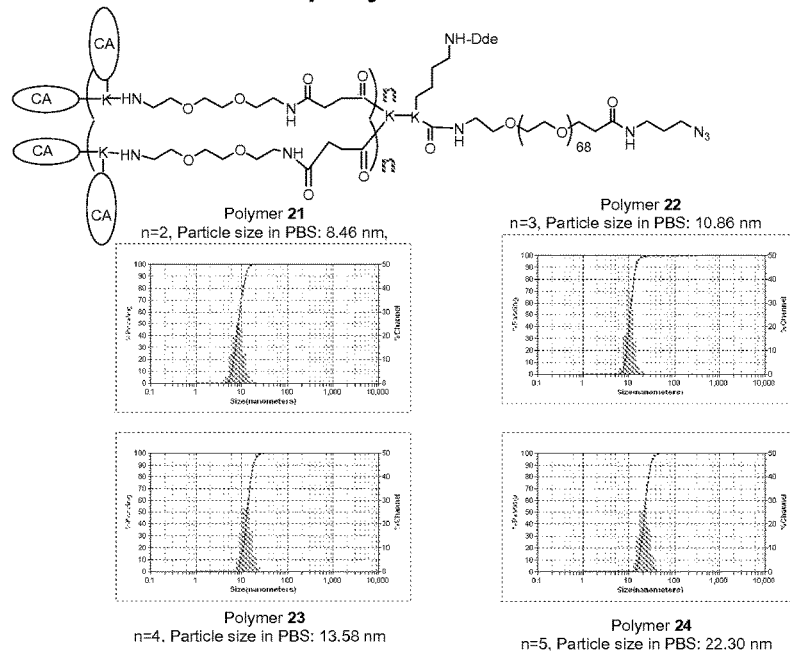
FIG. 27 shows the particle size for nanocarriers of the branched series 1 architecture versus the number of cholic acid groups.
Figure 41A:
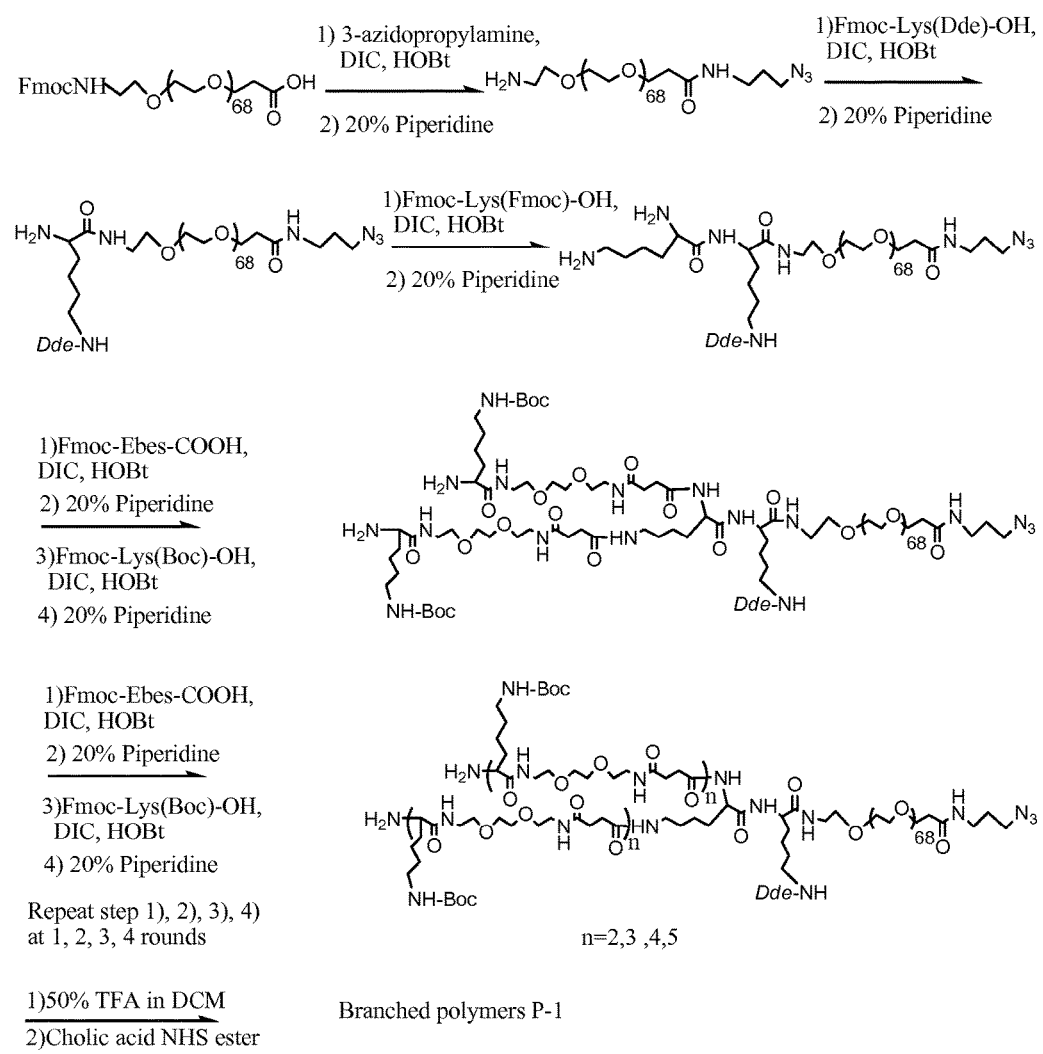
FIGS. 41A and 41B show the synthesis (41A) of members of branched polymer series 1 (P-1) and products (41B) of the synthesis.
Figure 41B:
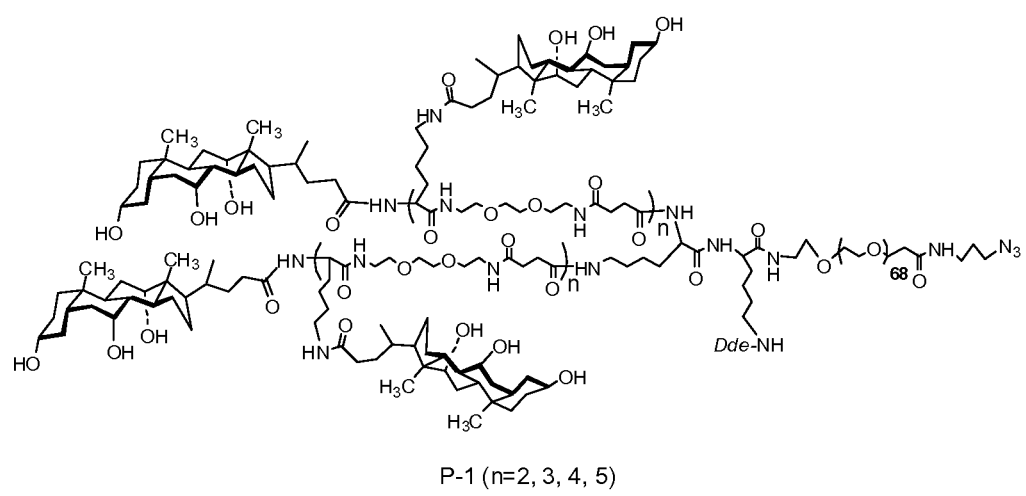

The branched cholic acid-PEG polymers branch series 1 and 4 were prepared via the same solution phase condensation reactions as in the preparation of telodendrimers. The isolation of soluble PEGylated products was achieved by precipitation in cold ether. Taking polymer 21 as an example for the synthetic procedure of branched polymer series 1 (FIG. 27) and synthetic scheme is shown in FIG. 41: 3-azidopropylamine (3 eq.) was coupled onto the carboxylic group of the FmocNH-PEG-COOH (3000 Da) using N-Hydroxybenzotriazole (HOBt 3 eq.)/diisopropyl carbodimide (DIC 3 eq.) as coupling agents in DMF overnight. The polymer was subsequently precipitated and washed with cold ether. After removal of the Fmoc via a 20% piperidine solution in DMF, (Fmoc)Lys(Dde)-OH (3 eq.) was coupled onto the N terminus of PEG using DIC and HOBt as coupling reagents until a negative Kais test result was obtained, thereby indicating completion of the coupling reaction. The PEGylated compounds were then precipitated and washed with cold ether. The branched structure was achieved by a coupling of (Fmoc)lys(Fmoc)-OH via Fmoc peptide synthesis after remove of the Fmoc on the N terminal of PEG with the treatment of 20% piperidine solution in DMF. Two flexible spacer molecule (Fmoc-Ebes) were coupled onto the amino groups of lysine. Then (Fmoc)Lys(Boc)-OH were coupled onto the spacer molecules after removal of Fmoc groups using 20% piperidine solution in DMF. After the repeated coupling of (Fmoc)Ebes-OH linker and (6 eq.) and (Fmoc)Lys(Boc)-OH (6 eq.) using Fmoc peptide synthesis procedure, The scaffolds of polymers 21, 22, 23 and 24 were synthesized with 2, 3, 4 and 5 repeating unites of [Ebes-lys(Boc)], respectively. After removal of Fmoc using 20% piperidine solution in DMF and the removal of Boc group using 50% TFA/DCM, cholic acid NHS ester reacted with the free amino groups of the scaffolds to generate the polymers 21-24 in P-1 series. The polymers were precipitated and washed by cold ether and dissolved in water. The polymer solution was filtered and then dialyzed against 4 L water in a dialysis tube with MWCO of 3.5 KDa; reservoir water was refreshed completely four times in 24 h. Finally, the polymers were lyophilized.

Branched Polymer Series 2.

Figure 28:
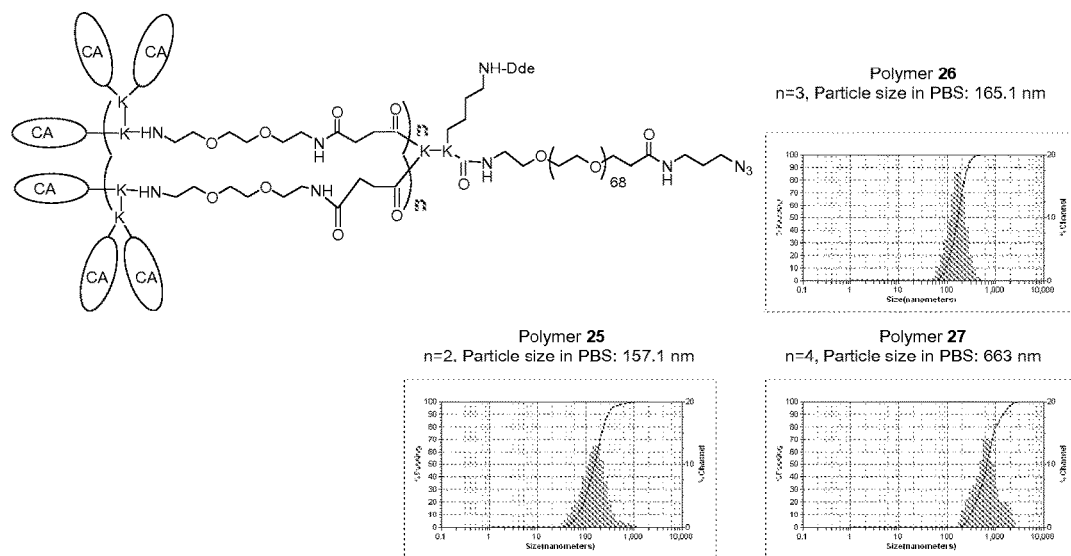
FIG. 28 shows the particle size for nanocarriers of the branched series 2 architecture versus the number of cholic acid groups.
Figure 32:
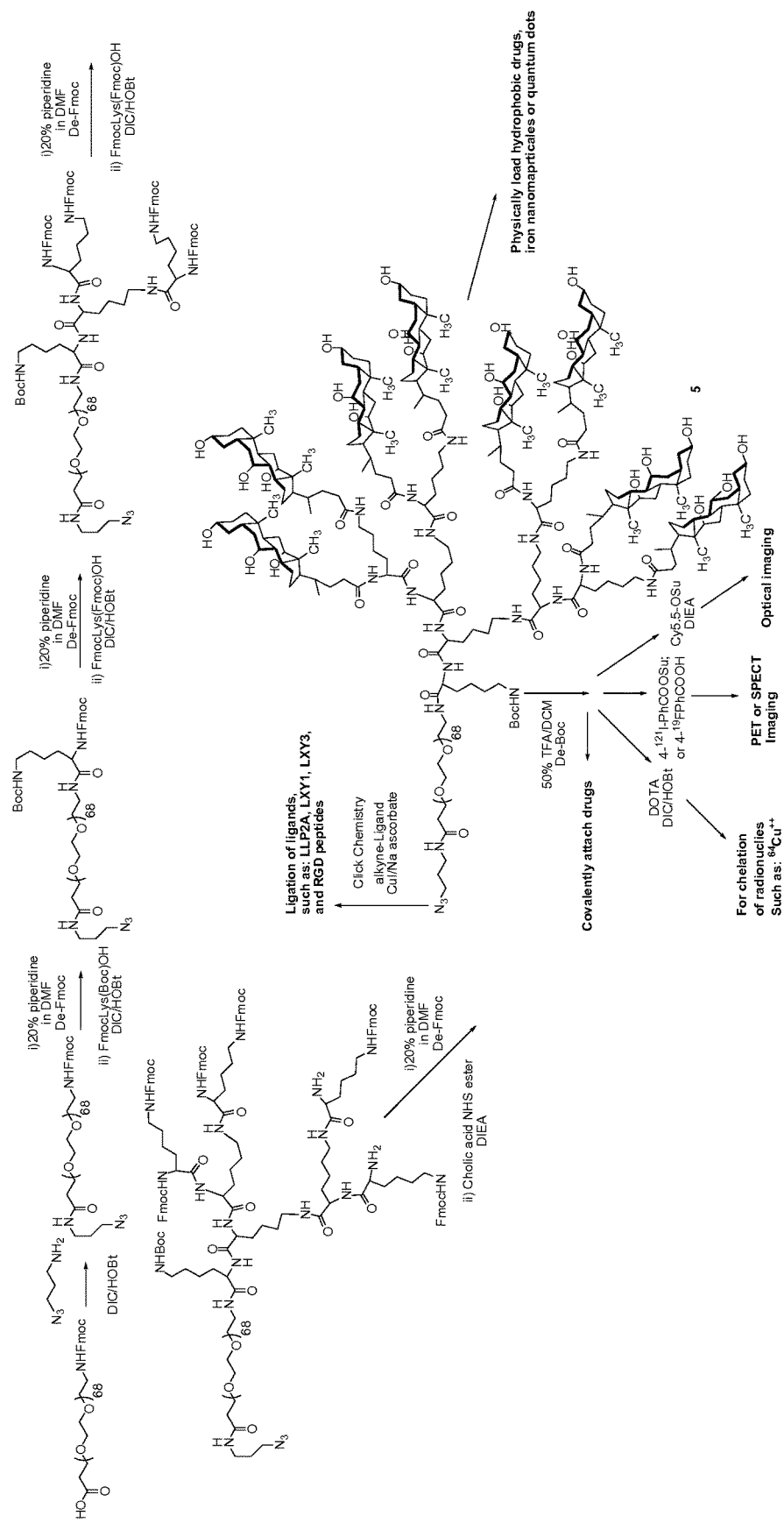
FIG. 32 shows a synthetic scheme for the preparation of telodendrimers of the present invention.
Figure 48A:
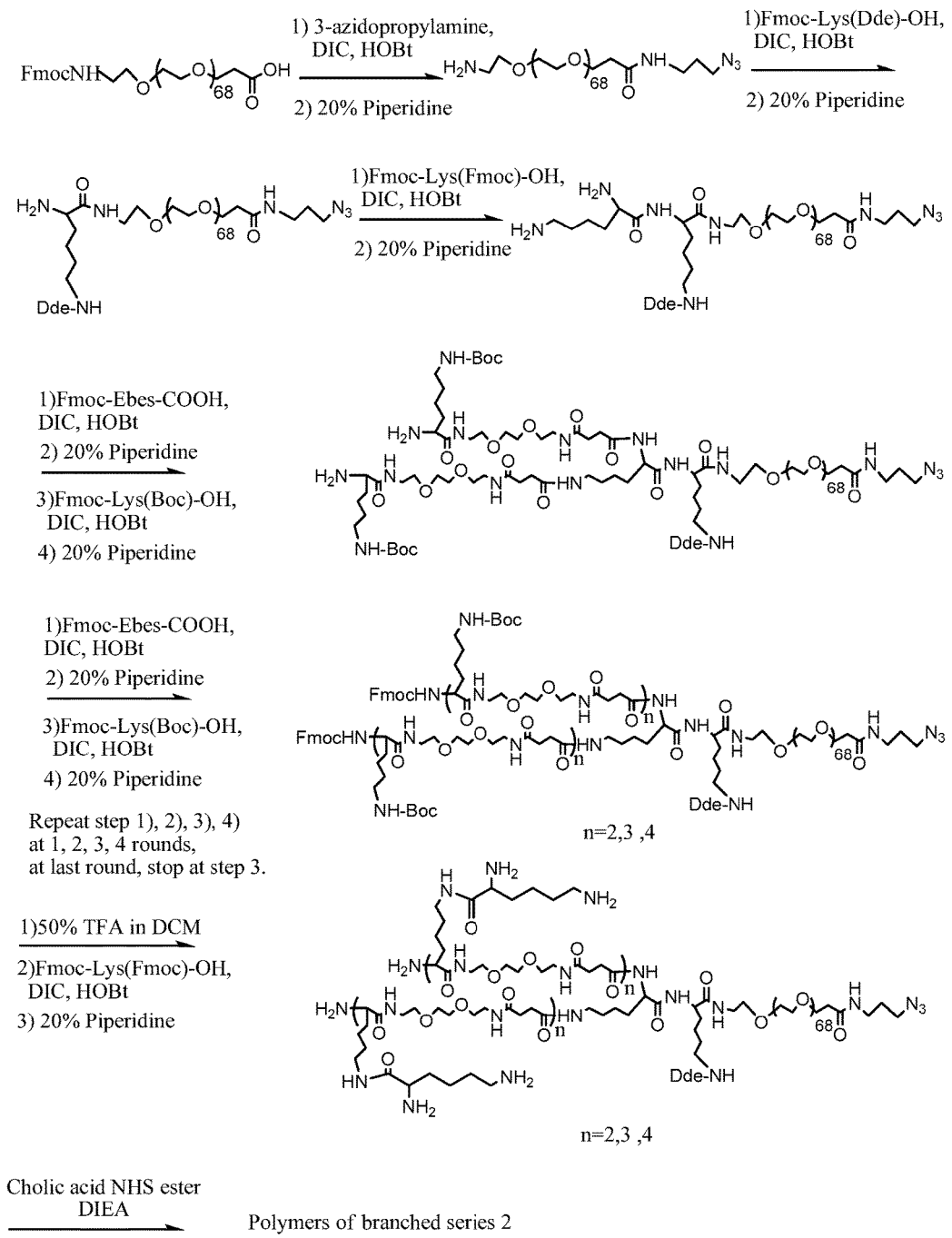
FIGS. 48A and 48B show the synthesis (48A) of members of branched polymer series 2 (P-2) and products (48B) of the synthesis.
Figure 48B:
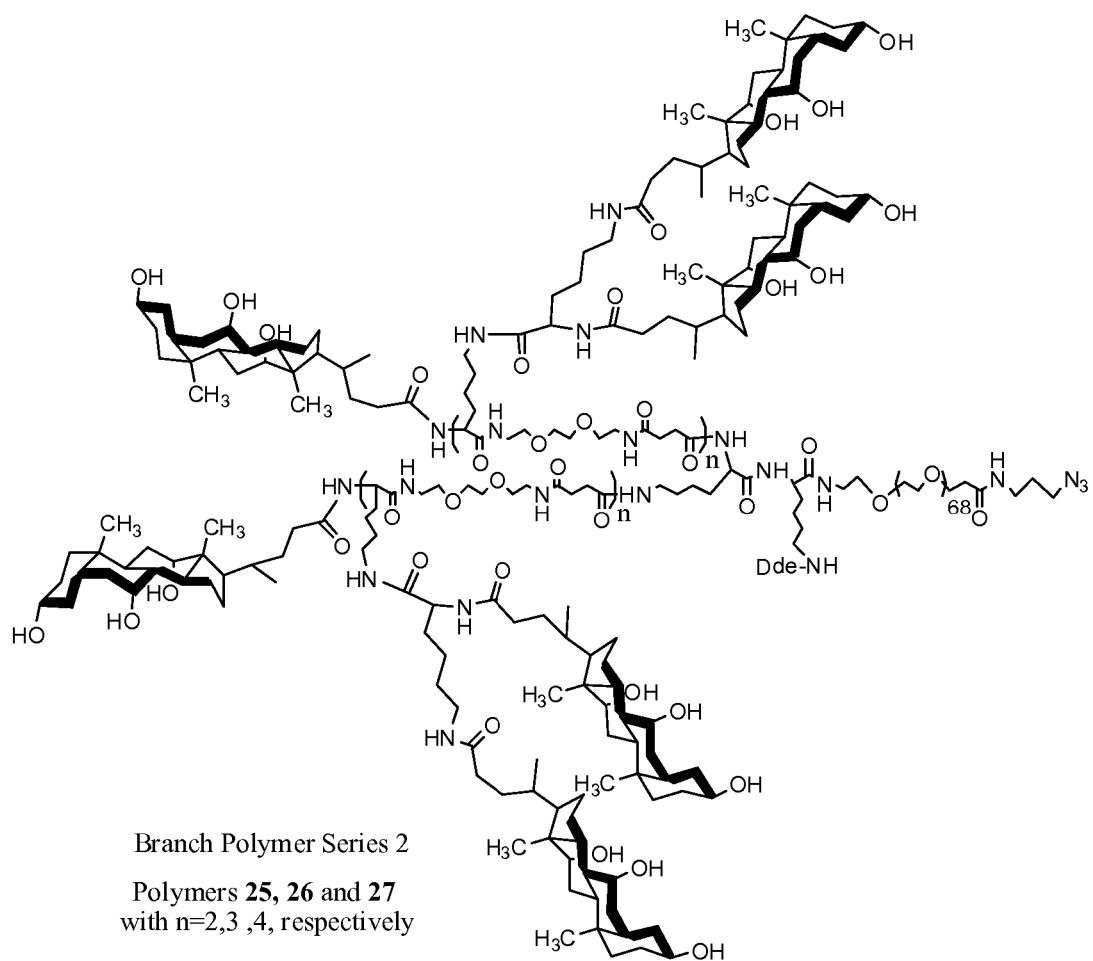

Synthesis of branched polymer series 2 (FIG. 28) as shown in FIG. 48: Series 2 polymers were synthesized with the similar strategy with branched polymer series 1 via Fmoc peptide chemistry. 3-azidopropylamine (3 eq.) was coupled onto the carboxylic group of the FmocNH-PEG-COOH (3000 Da) using N-Hydroxybenzotriazole (HOBt 3 eq.)/diisopropyl carbodimide (DIC 3 eq.) as coupling agents in DMF overnight. The polymer was subsequently precipitated and washed with cold ether. After removal of the Fmoc via a 20% piperidine solution in DMF, (Fmoc)Lys(Dde)-OH (3 eq.) was coupled onto the N terminus of PEG using DIC and HOBt as coupling reagents until a negative Kais test result was obtained, thereby indicating completion of the coupling reaction. The PEGylated compounds were then precipitated and washed with cold ether. The branched structure was achieved by a coupling of (Fmoc)lys(Fmoc)-OH via Fmoc peptide synthesis after remove of the Fmoc on the N terminal of PEG with the treatment of 20% piperidine solution in DMF. Two flexible spacer molecule (Fmoc-Ebes) were coupled onto the amino groups of lysine. Then (Fmoc)Lys(Boc)-OH were coupled onto the spacer molecules after removal of Fmoc groups using 20% piperidine solution in DMF. After the repeated coupling of (Fmoc)Ebes-OH linker and (6 eq.) and (Fmoc)Lys(Boc)-OH (6 eq.) using Fmoc peptide synthesis procedure, The scaffolds of polymers 25, 26 and 27 were synthesized with 2, 3 and 4 repeating unites of [Ebes-lys(Boc)], respectively. After removal of Boc group using 50% TFA/DCM, (Fmoc)lys(Fmoc)-OH is coupled onto the amino groups on the lysine side chains to double the amino groups in each repeat unites. After remove of Fmoc protecting groups using 20% piperidine solution in DMF, cholic acid NHS ester reacted with the free amino groups of the scaffolds to generate the polymers 25-27 in the branched polymers series 2. The polymers were precipitated and washed by cold ether and dissolved in water. The polymer solution was filtered and then dialyzed against 4 L water in a dialysis tube with MWCO of 3.5 KDa; reservoir water was refreshed completely four times in 24 h. Finally, the polymers were lyophilized.

Branched Polymer Series 3.

Figure 49A:
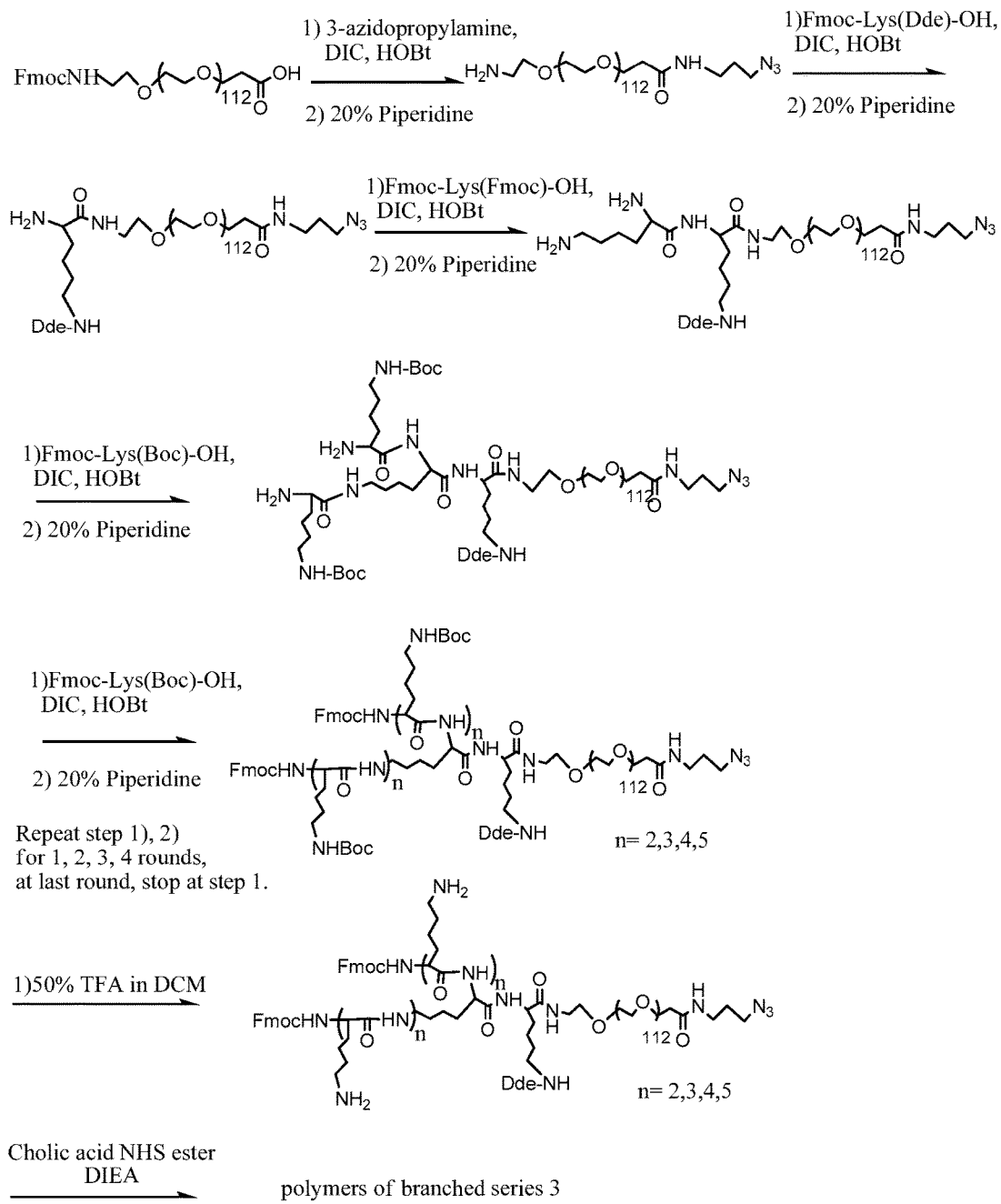
FIGS. 49A and 49B show the synthesis (49A) of members of branched polymer series 3 (P-3) and products (49B) of the synthesis.
Figure 49B:
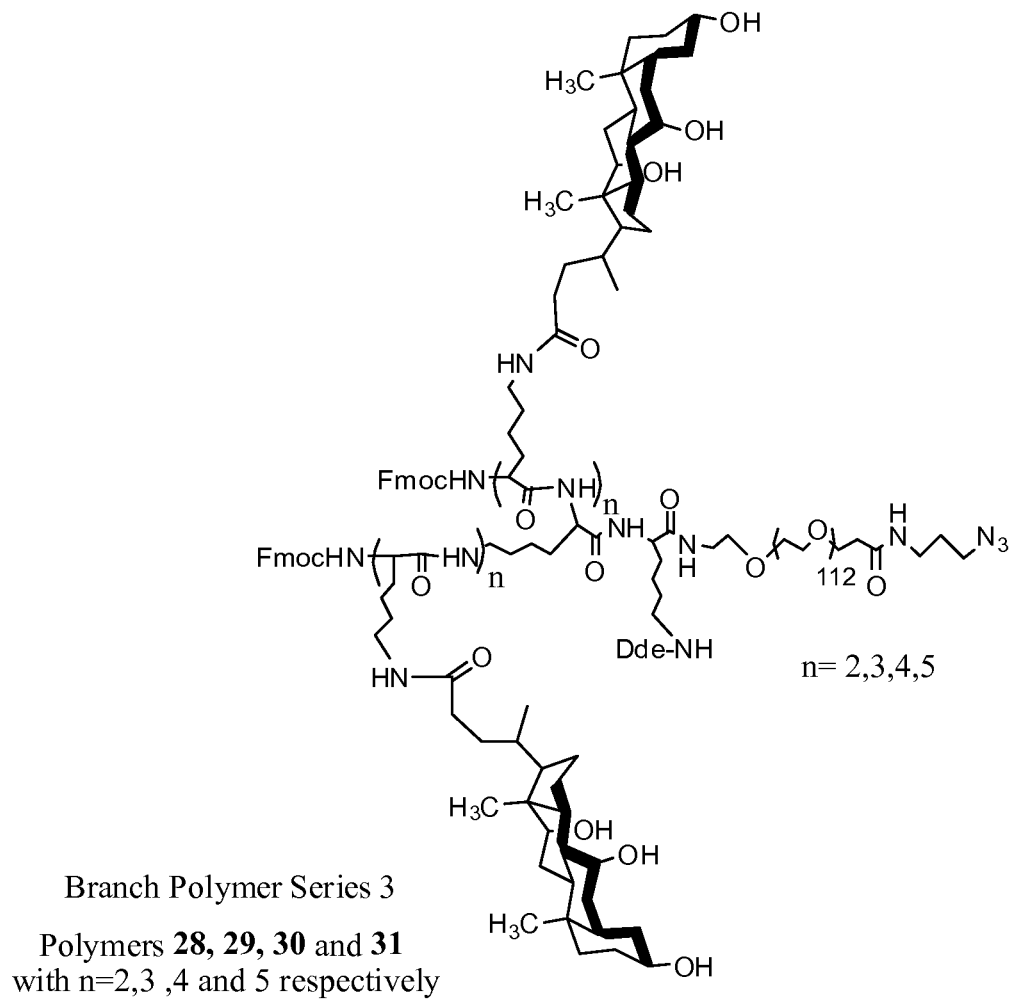

Synthesis of branched polymer series 3 (FIG. 29) as shown in FIG. 49: Series 3 polymers were synthesized in the similar strategy with branched polymer series 1 via Fmoc peptide chemistry without using Ebes linker molecules in the repeat unites. 3-azidopropylamine (3 eq.) was coupled onto the carboxylic group of the FmocNH-PEG-COOH (5000 Da) using N-Hydroxybenzotriazole (HOBt 3 eq.)/diisopropyl carbodimide (DIC 3 eq.) as coupling agents in DMF overnight. The polymer was subsequently precipitated and washed with cold ether. After removal of the Fmoc via a 20% piperidine solution in DMF, (Fmoc)Lys(Dde)-OH (3 eq.) was coupled onto the N terminus of PEG using DIC and HOBt as coupling reagents until a negative Kais test result was obtained, thereby indicating completion of the coupling reaction. The PEGylated compounds were then precipitated and washed with cold ether. The branched structure was achieved by a coupling of (Fmoc)lys(Fmoc)-OH via Fmoc peptide synthesis after remove of the Fmoc on the N terminal of PEG with the treatment of 20% piperidine solution in DMF. Two (Fmoc)Lys(Boc)-OH were coupled onto the amino groups of lysine. After the repeated coupling of (Fmoc)Lys(Boc)-OH (6 eq.) using Fmoc peptide synthesis procedure, The scaffolds of polymers 28, 29, 30 and 31 were synthesized with 2, 3, 4 and 5 repeating unites of [lys(Boc)], respectively. After removal of Boc group using 50% TFA/DCM, cholic acid NHS ester reacted with the free amino groups of the scaffolds to generate the polymers 28-31 in the branched polymers series 3. The polymers were precipitated and washed by cold ether and dissolved in water. The polymer solution was filtered and then dialyzed against 4 L water in a dialysis tube with MWCO of 3.5 KDa; reservoir water was refreshed completely four times in 24 h. Finally, the polymers were lyophilized.

Branched Polymer Series 4.

Figure 50A:
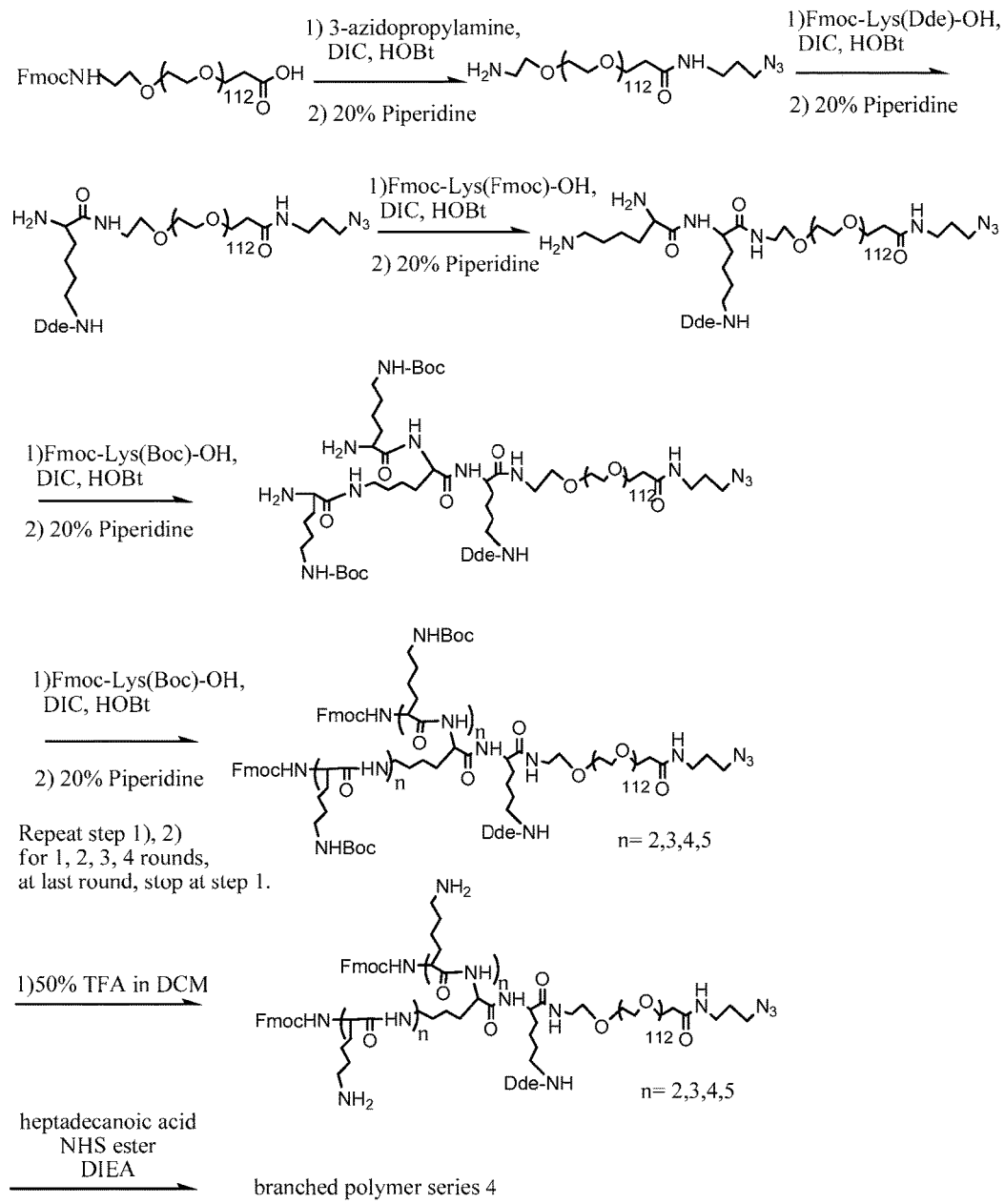
FIGS. 50A and 50B show the synthesis (50A) of members of branched polymer series 4 (P-4) and products (50B) of the synthesis.
Figure 50B:
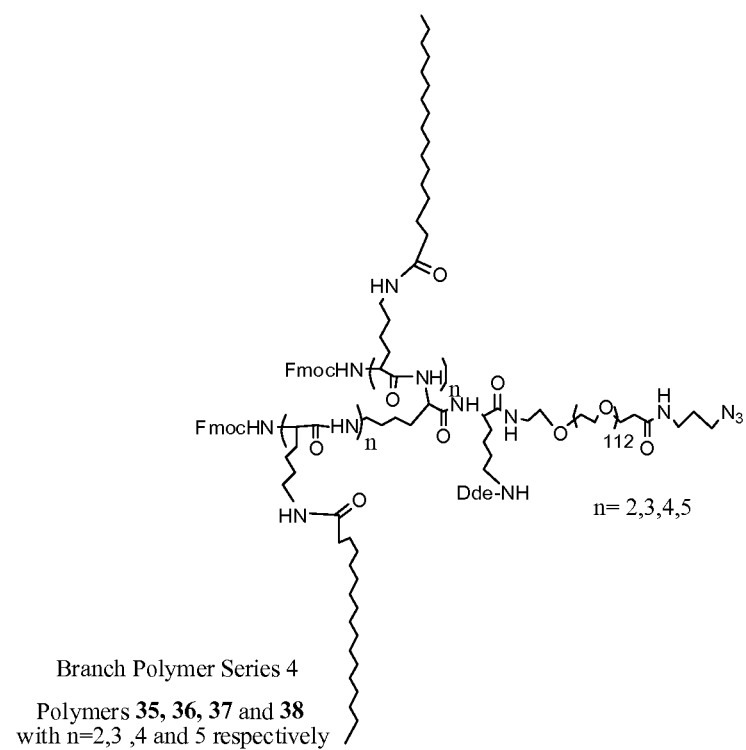

As in branch polymer series 4 (FIG. 30), the scaffolds of the polymers are identical with polymers in series 3, and heptadecanoic acid was used instead of cholic acid as hydrophobic segments (FIG. 50). 3-azidopropylamine (3 eq.) was coupled onto the carboxylic group of the FmocNH-PEG-COOH (5000 Da) using N-Hydroxybenzotriazole (HOBt 3 eq.)/diisopropyl carbodimide (DIC 3 eq.) as coupling agents in DMF overnight. The polymer was subsequently precipitated and washed with cold ether. After removal of the Fmoc via a 20% piperidine solution in DMF, (Fmoc)Lys(Dde)-OH (3 eq.) was coupled onto the N terminus of PEG using DIC and HOBt as coupling reagents until a negative Kais test result was obtained, thereby indicating completion of the coupling reaction. The PEGylated compounds were then precipitated and washed with cold ether. The branched structure was achieved by a coupling of (Fmoc)lys(Fmoc)-OH via Fmoc peptide synthesis after remove of the Fmoc on the N terminal of PEG with the treatment of 20% piperidine solution in DMF. Two (Fmoc)Lys(Boc)-OH were coupled onto the amino groups of lysine. After the repeated coupling of (Fmoc)Lys(Boc)-OH (6 eq.) using Fmoc peptide synthesis procedure, The scaffolds of polymers 35, 36, 37 and 38 were synthesized with 2, 3, 4 and 5 repeating unites of [lys(Boc)], respectively. After removal of Boc group using 50% TFA/DCM, heptadecanoic acid NHS ester reacted with the free amino groups of the scaffolds to generate the polymers 35-38 in the branched polymers series 3. The polymers were precipitated and washed by cold ether and dissolved in water. The polymer solution was filtered and then dialyzed against 4 L water in a dialysis tube with MWCO of 3.5 KDa; reservoir water was refreshed completely four times in 24 h. Finally, the polymers were lyophilized.

Example 6

Drug Loading

Drug Loading Methods:

The loading of PTX as a hydrophobic drug into the polymeric nanoparticles in aqueous solution has been optimized. We have evaluated three different methods:

Direct Dissolution Method 1 mg of PTX powder was added into 0.1 mL polymeric aqueous solution (10 mg/mL). The mixture was sonicated for 2 h at room temperature, followed by the centrifugation at 1000 rpm to remove the undissolved drug. The supernatant was filtrated through a filter with 0.2 μm pore size. The loading of the PTX was determined by HPLC: an aliquot of drug-micelle solution was withdraw and diluted 10 times with DMSO before injected into HPLC. The concentration of PTX was calculated based on the area under the PTX peak. We were able to show that the PEG-CA polymer solution could increase the solubility of PTX in aqueous solution around 10 times higher than when linear PEG was used. This method avoids the use of organic solvent. Using this method, we have observed that the drug loading capacity of polymer 4 was higher than that of polymer 2 and 6, and it can reach a drug loading capacity of 1.1 mg/mL.

Dialysis Method 0.1 mL of concentrated PTX solution in DMSO was added dropwise into a polymeric solution in PBS (10 mg/mL) while agitated on vortexer. The mixture was sonicated for 2 h at room temperature to facilitate the drug loading into the micelle. The DMSO and the free drug were removed by dialysis against PBS using a membrane with a MWCO of 3000 or by centrifugal filtration.

Evaporation Method

PTX and polymer were first dissolved in an organic solvent, such as chloroform, acetone, ethanol, etc. The organic solvent was rotavaporated in a round bottom flask under vacuum to form a thin film, which was further dried under high vacuum for 30 min to remove organic solvent. PBS buffer solution was added into the flask, followed by the sonication for 2 hours to disperse the polymer-drug conjugates into water. Finally, the micelle solution was filtered through a 0.2 μm filter.

Co-Loading of DiD and PTX into Micelles

To monitor the real-time biodistribution of $PEG^{5k}$-$CA_8$ nanoparticles with optical imaging systems, DiD (hydrophobic NIRF dye) and PTX were co-loaded into the nanocarrier using the same evaporation method described as above. The concentration of PTX loaded in $PEG^{5k}$-$CA_8$ nanoparticles was measured by HPLC. The mean diameter and zeta potential of the nanoparticles after PTX and DiD loading were evaluated by dynamic light scanning (DLS).

Table 1 summarizes the physico-chemical properties of the various novel nanocarriers discussed above. Overall, Polymers 7-9 with 5 KDa PEG chain seem to be able to generate nanoparticles with optimal therapeutic sizes (20-60 nm) and drug loading properties. We shall conjugate our ovarian cancer targeting ligands to the azido group of the PEG linker of polymer 7 for ovarian cancer therapeutic targeting studies.

TABLE 1

Physico-chemical properties of the various novel nanocarriers

| Polymer No. | Polymer Structure | Mw (theo.) | Mw $(MS)^a$ | Mw $(NMR)^b$ | CMC $(\mu M)^c$ | Particle Size without PTX $(nm)^d$ | Particle Size with PTX $(nm)^d$ | PTX Loading Capacity $(mg/mL)^e$ |
|---|---|---|---|---|---|---|---|---|
| 1 | $CA_3$ | 1320 | 1320 | N/D | N/D | 1 | N/D | N/D |
| 2 | $CA_3$-$PEG_9$ | 7700 | N/D | N/D | N/D | 4 | N/D | $0.58^f$ |
| 3 | $CA_4$ | 1962 | 1961 | N/D | N/D | 77 | N/D | N/D |
| 4 | $PEG^{3000}$-$CA_4$ | 5250 | 5606 | 5251 | 12.5 | 15 | 141 | $5.6^e$ |
| 5 | $PEG^{3000}$-$CA_8$ | 7322 | 7624 | 8025 | 5.9 | 21 | 58 | 4.7 |
| 6 | $PEG^{5000}$-$CA_4$ | 6644 | 6313 | 6082 | 67 | 10 | 131 | 2.3 |
| 7 | $PEG^{5000}$-$CA_8$ | 8716 | 8814 | 8805 | 5.3 | 21 | 61 | 7.3 |
| 8 | $MeOPEG^{5000}$-O-$CA_8$ | 8716 | N/D | N/D | 5.9 | 20 | 33 | $6.49^e$ |
| 9 | $MeOPEG^{5000}$-NH-$CA_8$ | 8716 | N/D | N/D | 5.3 | 15 | 22 | $5.8^e$ |
| 10 | $MeOPEG^{5000}$-NH-$CF_8^h$ | 8909 | N/D | N/D | 0.4 | 122/280/827 | 134/388/905 | $0.01^g$ |
| 11 | $MeOPEG^{5000}$-NH-$LA_8^h$ | 8460 | N/D | N/D | 1.8 | 73/6000 | 67/450/872 | $0.82^g$ |
| 12 | $MeOPEG^{5000}$-NH-$HA_8^h$ | 7620 | N/D | N/D | 1.5 | 55/322 | 97/5990 | N/D |
| 13 | CA-$PEG^{3350}$-CA | 4100 | N/D | N/D | 1.5 | 6 | 6/20/226 | $0.54^e$ |
| 14 | $MeOPEG^{5000}$-CA | 5500 | N/D | N/D | 1073 | 4 | 4/165 | N/D |
| 15 | $MeOPEG^{2000}$-CA | 2500 | N/D | N/D | 765 | 250 | 117/4560 | N/D |
| 16 | $PEG^{3000}$-$CA_4$-$PEG_{12}$ | 25500 | N/D | N/D | N/D | 8 | N/D | 0.64 |
| 32 | $PEG^{2000}$-$CA_4$ | 3914 | 4105 | 4511 | 7.9 | 11.5 | 15 | 5.2 |

TABLE 1-continued

Physico-chemical properties of the various novel nanocarriers

| Polymer No. | Polymer Structure | Mw (theo.) | Mw (MS)[a] | Mw (NMR)[b] | CMC (μM)[c] | Particle Size without PTX (nm)[d] | Particle Size with PTX (nm)[d] | PTX Loading Capacity (mg/mL)[e] |
|---|---|---|---|---|---|---|---|---|
| 33 | PEG$^{2000}$-CA$_8$ | 5986 | 5985 | 6127 | 1.3 | 302/6000 | 96/348/1863 | N/D |
| 34 | PEG$^{10000}$-CA$_{16}$ | 17204 | N/D | N/D | 0.97 | 42.7/2163 | 102/602/2435 | 0.6 |

[a]Obtained via MALDI-TOF MS analysis, α-cyano-hydroxyl-cinnamic acid as a matrix compound.

[b]Obtained via $^1$H NMR method. Given the molecular weights of the starting PEGs by MALDI-TOF MS, the molecular weight was calculated based on the ratio of proton signals of the methyl groups on cholic acid to the proton signals of the PEG in the $^1$H NMR spectra.

[c]CMC was measured by fluorescence spectrometry using pyrene (2 × 10$^{-6}$M) as a probe.

[d]Measured by dynamic light scattering particle sizer (Nanotrac ®).

[e]PTX loading, in the presence of 20 mg/mL of telodendrimers, were measured by HPLC after passing through an 0.45 μm filter.

N/D means not detectable

[f]PTX was loaded into nanocarriers by evaporation method with 10 mg/mL of polymer.

[g]The loading of PTX was analyzed after pass through 0.45 μm filter.

[h]CF = cholesterol formate; LA = lithocholic acid; HA = heptadecanoic acid.

TABLE 2

Physico-chemical properties of the Linear and Branched polymers using cholic acid as building block

| Type of polymer | Polymer | Number of Lysine (m) | Number of Linker (n) | Number of CA (o) | [a]Particle size in PBS (nm) | [b]Particle size after PTX Loading (nm) |
|---|---|---|---|---|---|---|
| Linear polymer series 1 (PEG 3000) | 17 | 2 | 2 | 5 | 9.58 | |
| | 18 | 3 | 3 | 7 | 11.69 | 17.67 (at 1.94 mg/ml) |
| | 19 | 4 | 4 | 9 | 12.64 | 149.00 (at 5.13 mg/ml) |
| | 20 | 5 | 5 | 11 | 20.22 | 19.66 (at 3.41 mg/ml) |
| Branch polymer series 1 (PEG 3000) | 21 | 4 | 4 | 6 | 8.46 | 17.00 (at 1.60 mg/ml) |
| | 22 | 6 | 6 | 8 | 10.86 | 23.08 (at 7.09 mg/ml) |
| | 23 | 8 | 8 | 10 | 13.58 | 29.62 (at 9.65 mg/ml) |
| | 24 | 10 | 10 | 12 | 22.30 | 32.40 (at 4.70 mg/ml) |
| Branch polymer series 2 (PEG 3000) | 25 | 4 | 4 | 10 | 157.10 | |
| | 26 | 6 | 6 | 14 | 165.10 | |
| | 27 | 8 | 8 | 18 | 663.00 | |
| Branch polymer series 3 (PEG 5000) | 28 | 4 | 0 | 4 | 16.98 | 26.81 (at 4.91 mg/ml) |
| | 29 | 6 | 0 | 6 | 18.19 | 30.80 (at 4.45 mg/ml) |
| | 30 | 8 | 0 | 8 | 27.55 | 47.20 (at 0.56 mg/ml) |
| | 31 | 10 | 0 | 10 | 50.20 | 104.60 (at 0.11 mg/ml) |
| Branch polymer series 4 (PEG 5000) | 35 | 4 | 0 | 4[d] | 34.8 | |
| | 36 | 6 | 0 | 6[d] | 37.4 | |
| | 37 | 8 | 0 | 8[d] | 76.7 | |
| | 38 | 10 | 0 | 10[d] | 70.4 | |

[a]Measured by Dynamic light scattering (Nanotrac ®), The concentration of polymer was kept at 20 mg/mL in PBS;

[b]Measured by Dynamic light scattering (Nanotrac ®), PTX was loaded into nanocarriers by evaporation method with 20 mg/mL of polymer, PTX loading was indicated in the bracket thereafter;

[c]PTX loading capacity of the nanocarriers prepared from the corresponding polymer, PTX was loaded into nanocarriers by evaporation method with 20 mg/mL of polymer.

[d]Cholic acid groups are replaced with heptadecanoic acid groups.

Example 7

Drug Release

Figure 10:
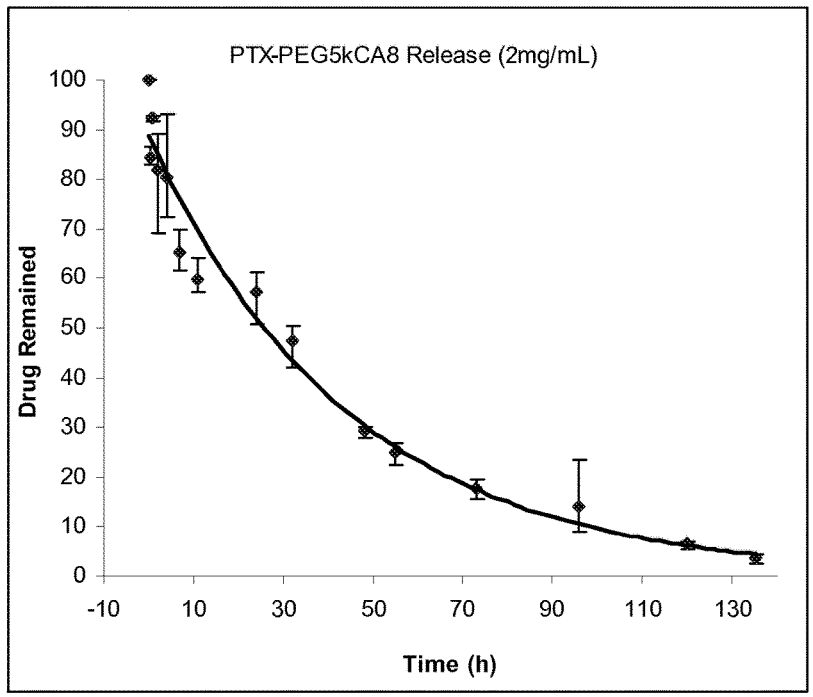
FIG. 10 shows the release of PTX from micelles formed by $PEG^{5000}$-$CA_8$ in PBS over time, as a percentage of the amount of drug remaining in the micelle. The percentage of PTX released was calculated according to the concentrations of PTX left in the dialysis cartridge.

The in vitro release of PTX from nanocarrier was studied using dialysis method against PBS solution. In this experiment, 4.6 mL of polymer 5 ($PEG^{3000}$-$CA_8$) at 10 mg/mL was loaded with PTX (3.2 mg/mL) in PBS, injected into a 3-12 mL dialysis cartridge with MWCO 3,500 (Pierce Chemical Inc.), and dialyzed against 4 L of PBS. The concentration of PTX remained in the dialysis cartridge at various time points was measured by HPLC. The accumulated drug release curve is shown in FIG. 10. After 24 h, about 50% of PTX was released from the micelle.

Example 8

Stability of Nanocarriers

Figure 11:
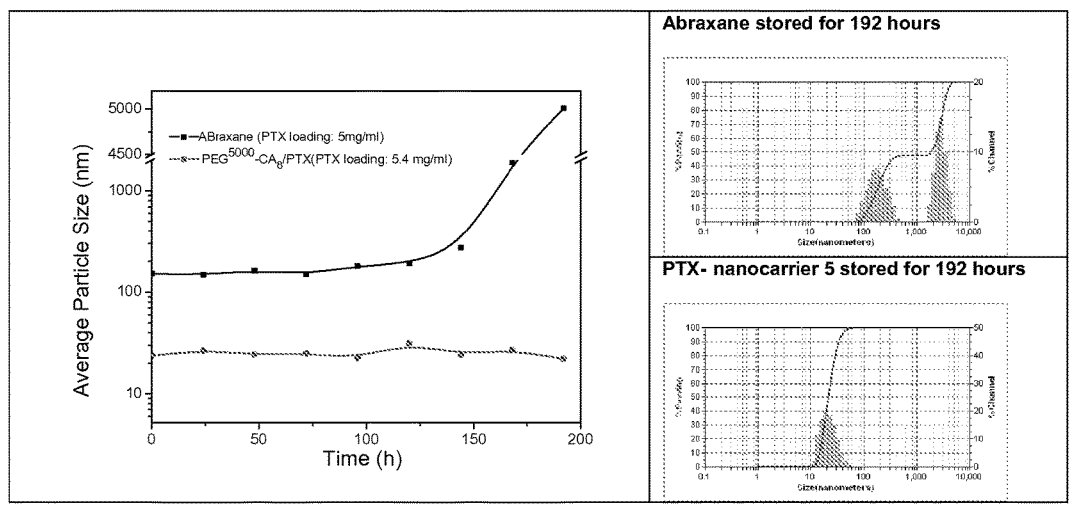
FIG. 11 shows the stability of PTX-loaded nanoparticles over time: PTX-micelle 7 ($PEG^{5000}$-$CA_8$) vs. Abraxane.

The particle size of Abraxane and the PTX loaded nanocarriers derived from $PEG^{5000}$-$CA_8$ (polymer 7) was monitored using the Nanotrac DLS particle sizer at different time point during storage at 4° C. Abraxane was found to have a bigger size (130 nm) and formed bigger aggregates (~3 μm) with visible white precipitates after 5 days storage (FIG. 11). In contrast, the particle size of PTX-nanocarrier 7 remained unchanged and there was no visible precipitate over the same period of time.

Example 9

Size of PTX Loaded Nanocarriers

Figure 12:
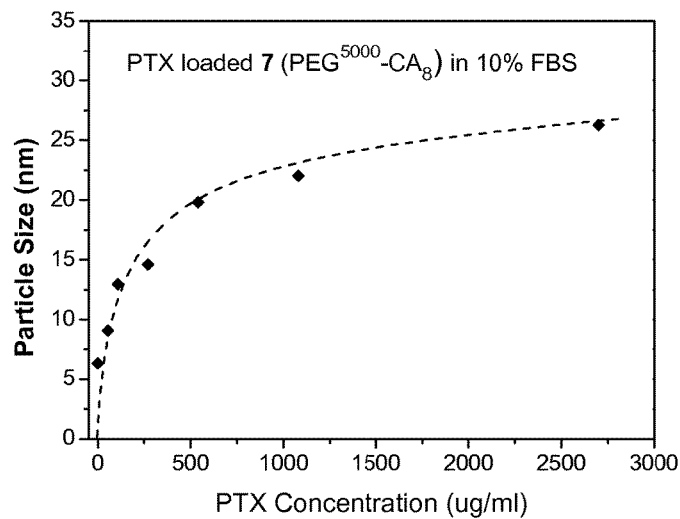
FIG. 12 shows the particle size of micelle 7 ($PEG^{5000}$-$CA_8$) loaded with PTX, as the PTX concentration in the micelle increases. The micelle is in 10% (v/v) Fetal Bovine Serum (FBS).
Figure 13:
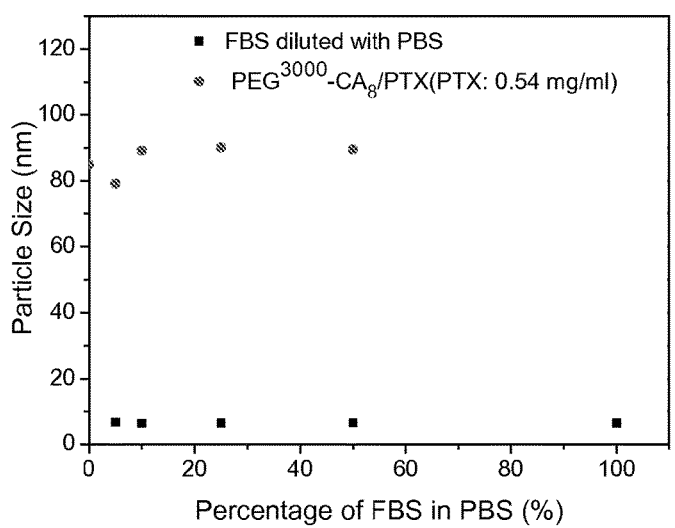
FIG. 13 shows the particle size of PTX-micelle 5 ($PEG^{3000}$-$CA_8$) (PTX loading: 0.54 mg/ml) in different concentrations of Fetal Bovine Serum (FBS).

The size of the PTX loaded micelles were studied in the presence of fetal bovine serum (FBS). FIG. 12 shows that with increasing concentration of PTX loaded into nanocarrier 7 in 10% FBS, the particle size of the nanocarrier was found to plateau at about 20 nm. FIG. 13 shows that the PTX loaded nanocarriers of polymer 5 remained stable at 90 nm in various concentrations of FBS, coexisting with the 6.5 nm particles present inside the FBS. The above studies indicate that the drug loaded micelles are stable in serum, which is critical for clinical applications.

Example 10

Cytotoxicity of Nanocarriers

Figure 14:
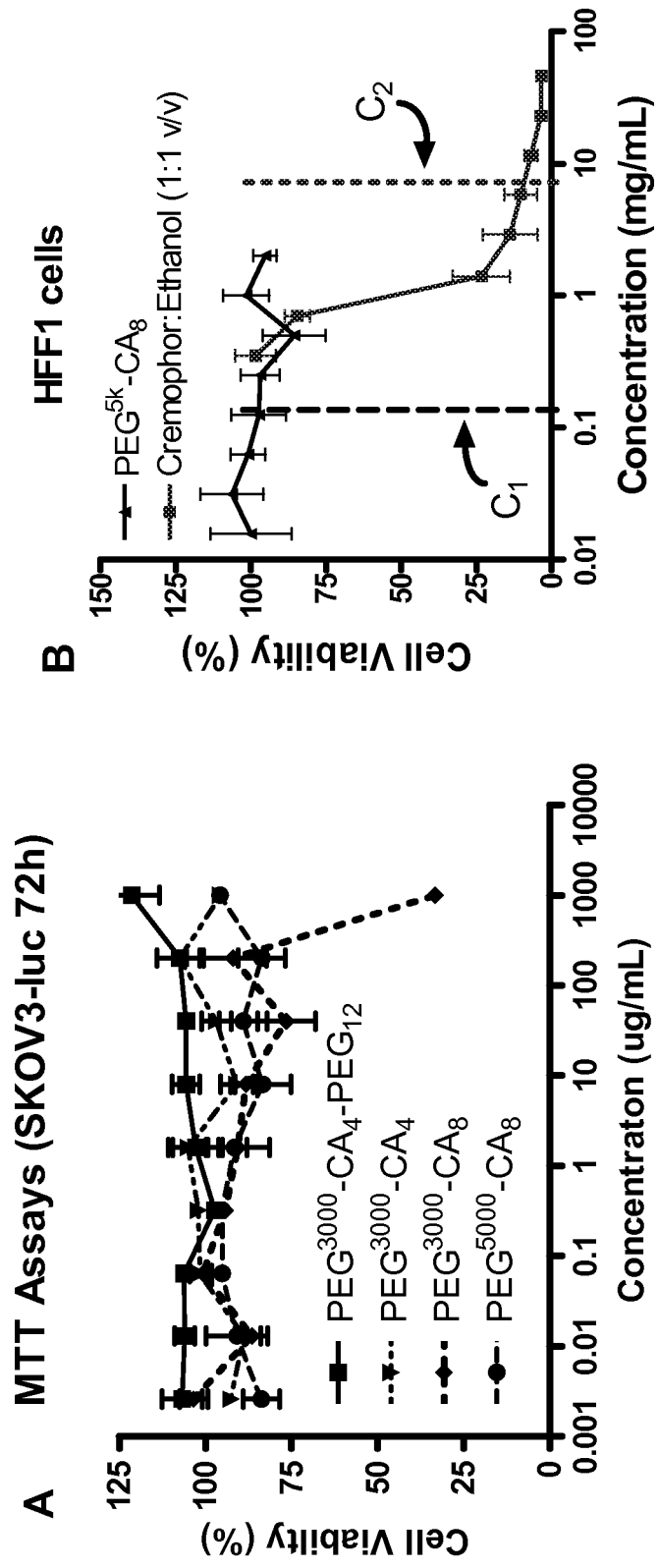
FIG. 14A shows the cytotoxicity of various polymers on SKOV-3 transfected with luciferase cells.
FIG. 14B shows cytotoxicity of unloaded $PEG^{5000}$-$CA_8$ NPs (polymer 7) and cremophor:ethanol vehicle on HFF1 human fibroblast cells. $C_1$ and $C_2$ are the estimated blood concentration of $PEG^{5000}$-$CA_8$ (polymer 7) and cremophor:ethanol after in vivo administration, respectively, assuming the blood volume of an average person is 6 L. The anticancer effects of PTX-loaded $PEG^{5000}$-$CA_8$ NPs were performed on ES-2 cells.

The cytotoxicity of PEG-CA polymer alone was evaluated with SKOV-3 (ovarian cancer cell line) in 96-well plates using MTT assay (FIG. 14). Polymers 4, 7 and 16 were found to have no observable cytotoxicity up to a polymer concentration of 1 mg/mL. Polymer 5 showed mild cytotoxic only at 1 mg/mL concentration, and was found non-toxic below 100 μg/mL. (B) Cytotoxicity of unloaded $PEG^{5000}$-$CA_8$ NPs and cremophor:ethanol vehicle on HFF1 human fibroblast cells. C1 and C2 are the estimated blood concentration of $PEG^{5000}$-$CA_8$ and cremophor:ethanol after in vivo administration, respectively, assuming the blood volume of an average person is 6 L.

Figure 15:
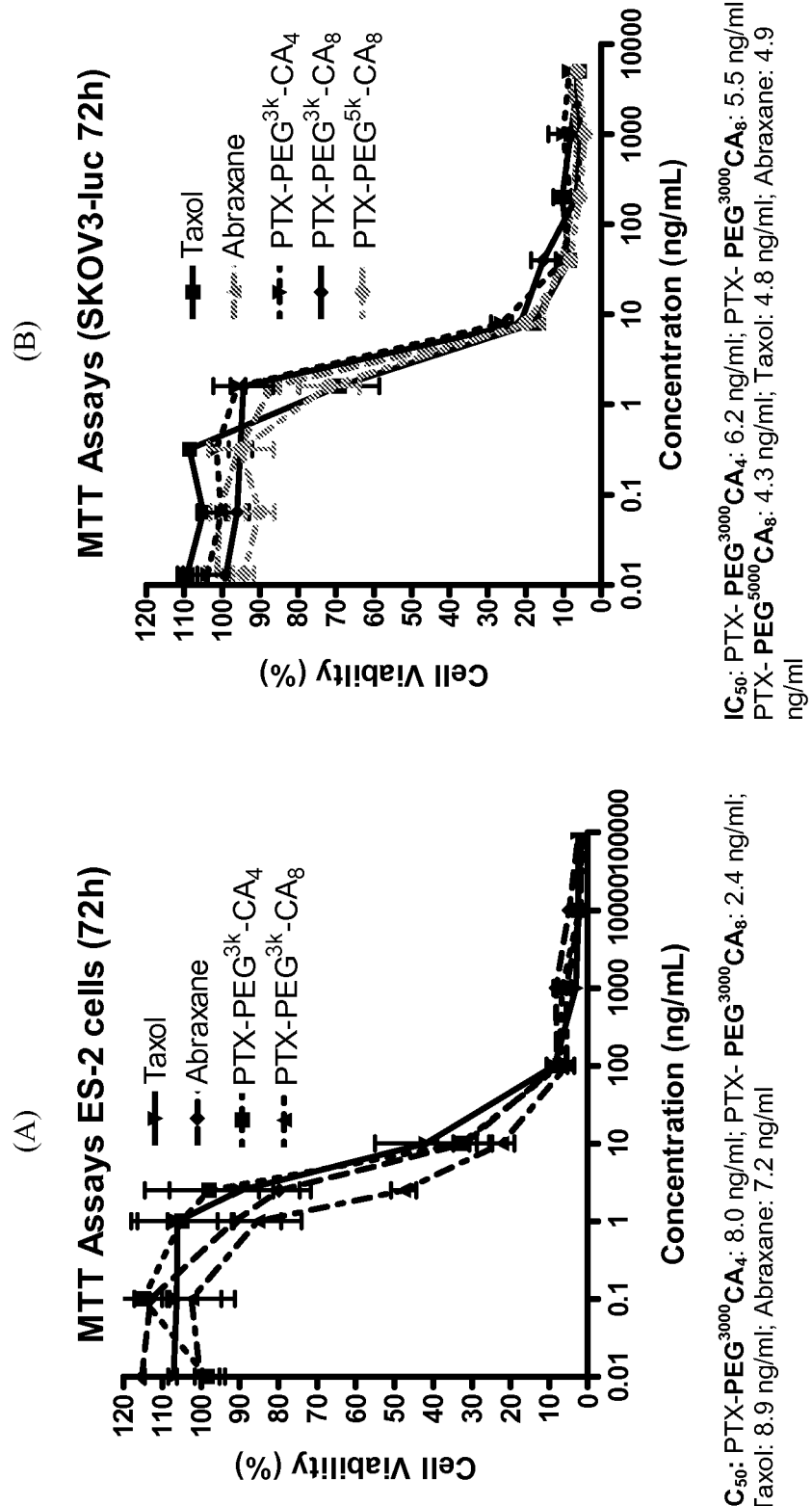
FIGS. 15A and 15B show the cytotoxicity of PTX loaded polymers on ES-2 (15A) and SKOV-3 cells (15B).

The cytotoxicity of the PTX loaded nanocarriers and two clinical formulations of paclitaxel (Taxol® and Abraxane®) on two different ovarian cancer cell lines were determined. After 72 hours of incubation with the drugs, the cells were washed and MTT assay performed. The $IC_{50}$ of the five paclitaxel formulations were found to be comparable. In ES-2 cell lines, PTX-$PEG^{3000}$-$CA_8$ appeared to be more potent than the other formulations (FIG. 15).

Example 11

In Vivo Efficacy Stud of $PEG^{5000}$-$CA_8$-PTX in Xenograft Mice Model I

Figure 16:
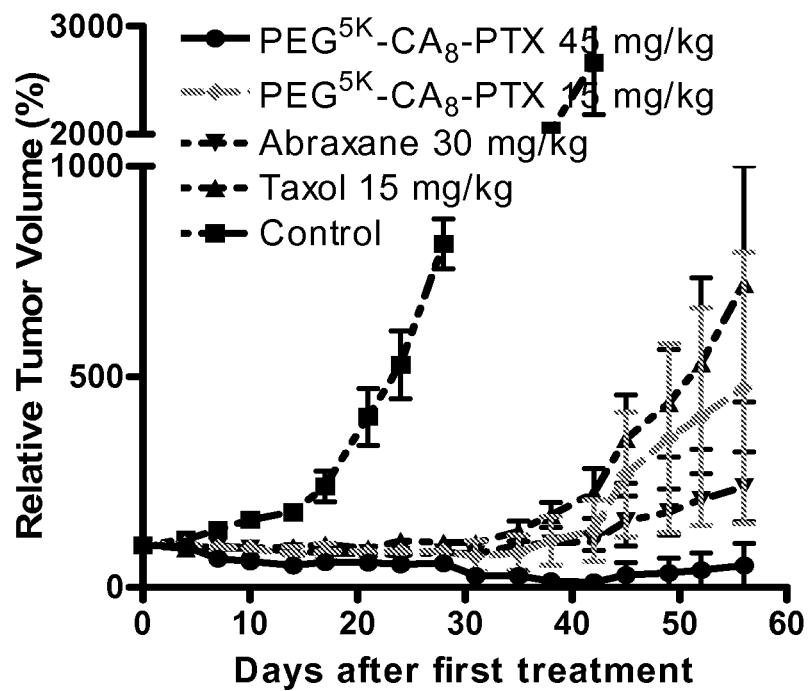
FIG. 16 shows the antitumor efficacy of different paclitaxel formulations in nude mice bearing human SKOV3-luc ovarian cancer xenograft. PBS (control), Taxol, Abraxane or the PEG5000-CA8-PTX preparations were administered i.v. on days 0, 4, 8, 12, 16 when tumor volume reached about 50 $mm^3$.

Nude mice bearing human SKOV-3 ovarian cancer cell transfected with lucerase gene was treated with various formulations of paclitaxel every 4 days for 5 doses. The result of tumor responses is shown in FIG. 16. The various paclitaxel preparations were administered when the xenograft was relatively small (50 $mm^3$); no tumor growth was detected in each of these five regimens for up to day 28 after the first treatment dose. In contrast, control mice treated with PBS alone showed rapid tumor growth about 16 days after the first treatment dose.

Figure 17:
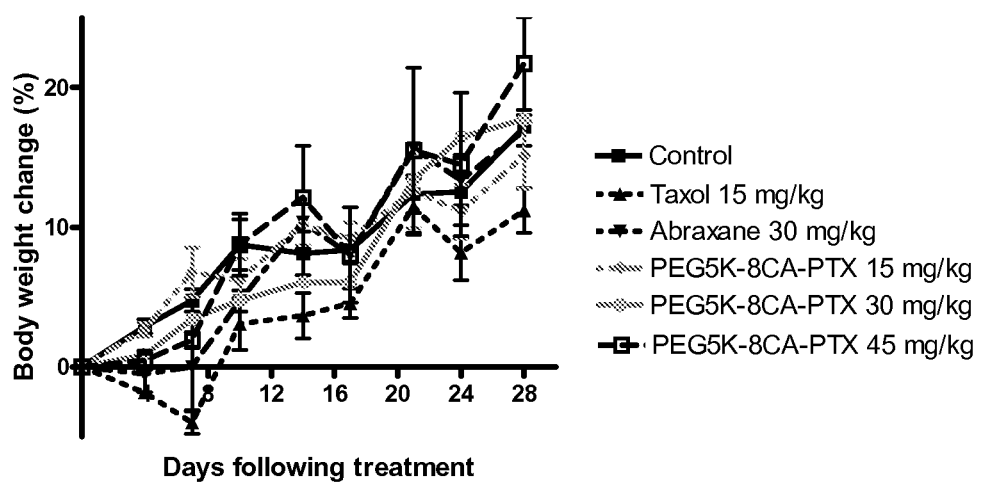
FIG. 17 shows the change in body weight of mice after treatment with various paclitaxel regimens or with saline (control).

No acute toxicity was observed in these five treatment groups and one saline control group. These mice were weighted over the course of the study. The result is shown in FIG. 17. For the group treated with taxol, there was significant weigh loss in the mice during the first week of treatment, and the weight continued to be the lowest, compared to the five treatment groups throughout the experiment. In contrast, the weight of the mice was similar for the saline control group, the Abraxane group, and the three $PEG^{5000}$-$CA_8$-PTX groups, indicating that the three novel paclitaxel nanotherapeutic preparations are at least as effective and tolerable as Abraxane.

Figure 18:
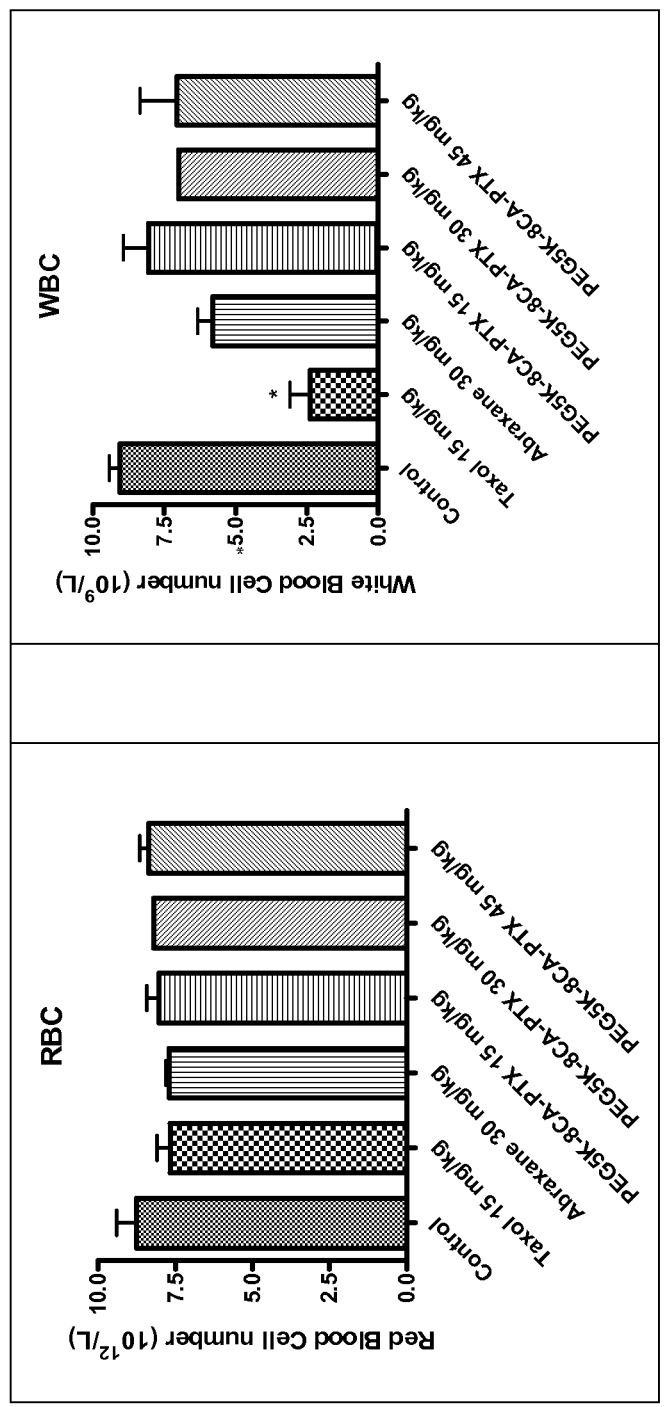
FIG. 18 shows red blood cell count (left) and white blood cell count (right) of nude mice bearing SKOV3-luc ovarian cancer xenograft after treatment with the various paclitaxel regimens or with saline (control).

The effects of the five regimens on RBC and WBC counts on day 28 after the first dose of paclitaxol regimen were also studied. The result is shown in FIG. 18. No significant difference in change of RBC count was seen in the five treatment and one control groups. In contrast, significant myelosuppression was observed in the Taxol group (70% drop in WBC counts). There was a 30% drop in WBC counts in the Abraxane group. In contrast, there was only a 10-20% drop in WBC counts in the three $PEG^{5K}$-$CA_8$-PTX groups. This data indicates that the three novel paclitaxel nanotherapeutic preparations are less myelosuppressive than Taxol and Abraxane.

Example 12

Biodistribution of Nanocarriers in Xenograft Mice Model I

Figure 19:
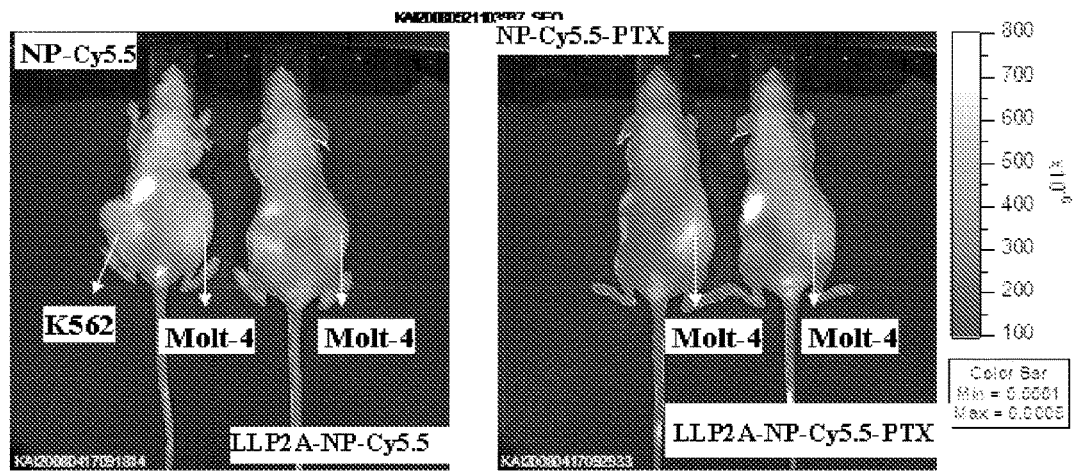
FIG. 19 shows the in vivo NIR fluorescence imaging of subcutaneous Molt-4 tumor bearing mice at 48 h after dye injection. The NP ($PEG^{3000}$-$CA_8$)-Cy5.5 and LLP2A-NP-Cy5.5 with and without loading PTX were given at a dose of 4 nmol per mouse via tail vein.
Figure 20:
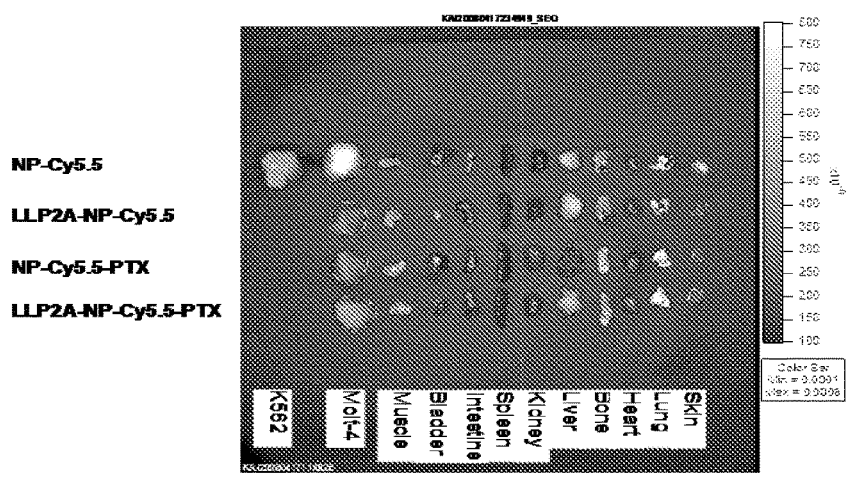
FIG. 20 shows the ex vivo image of tumors and organs at 48 h at 4 nM injection of NP ($PEG^{3000}$-$CA_8$, polymer 5)-Cy5.5.
Figure 21:
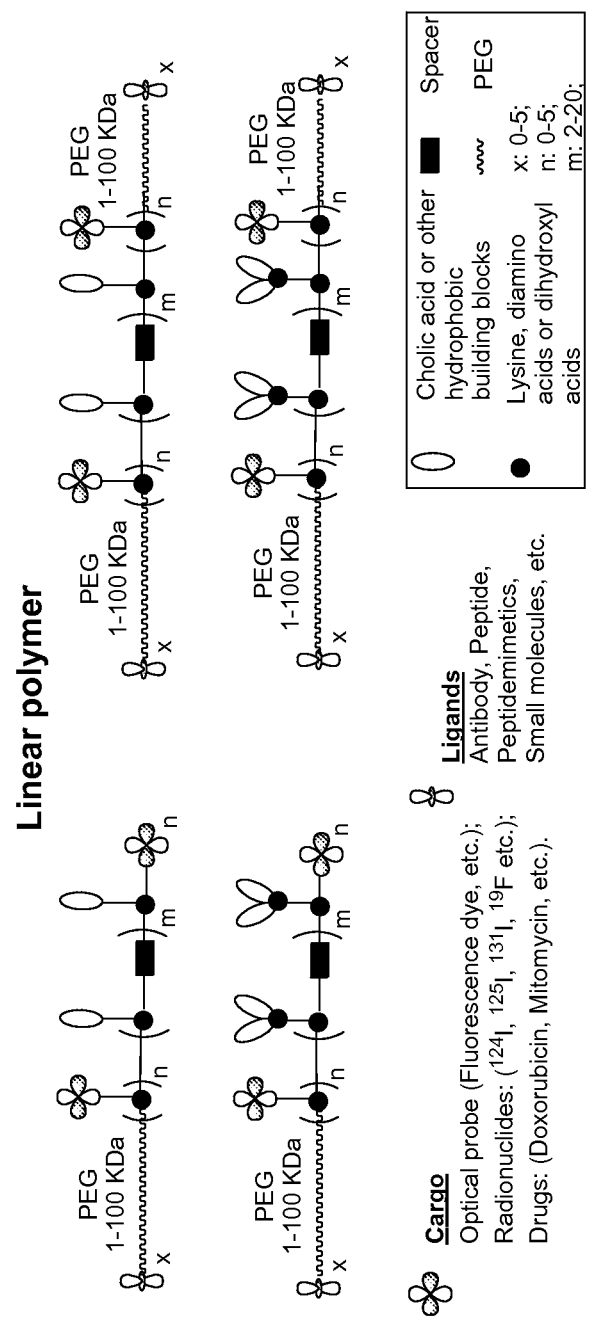
FIG. 21 shows the structure and functionalization of the linear polymers.
Figure 22:
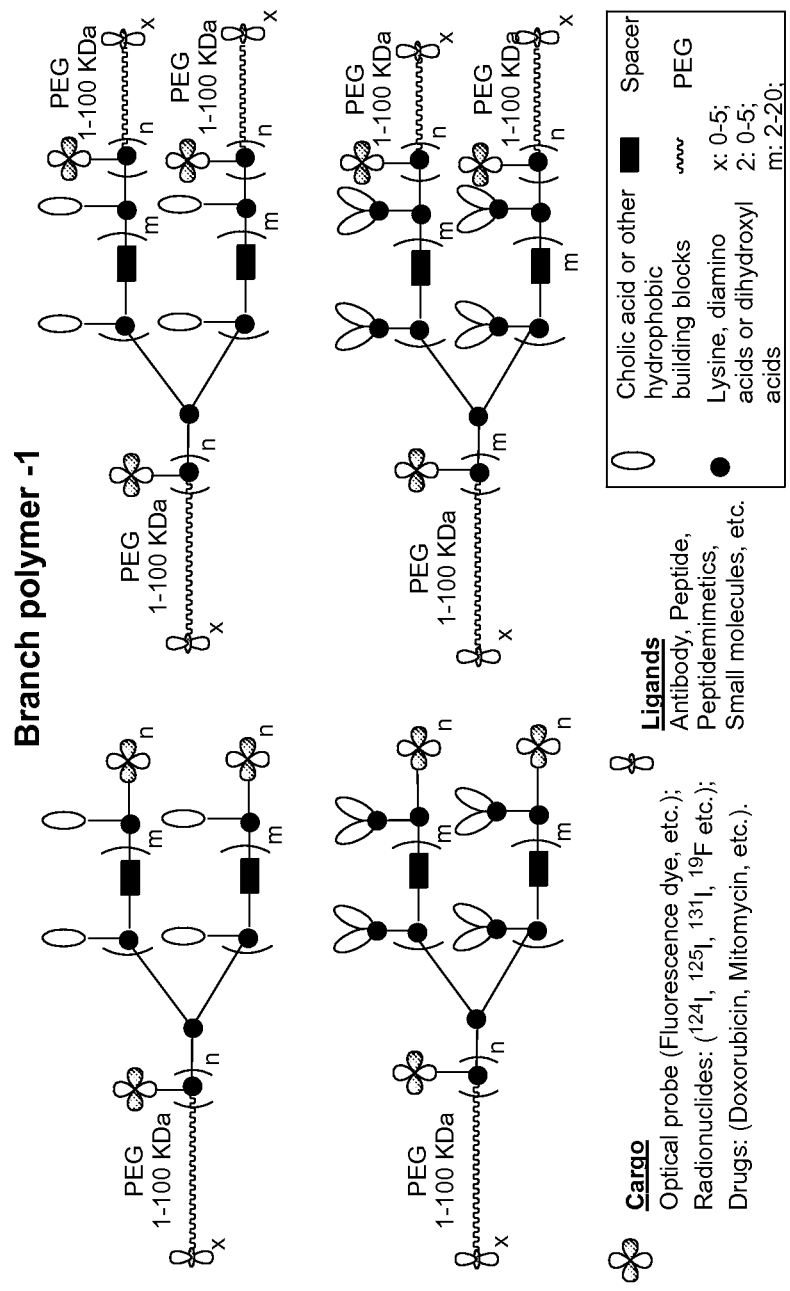
FIG. 22 shows the structure and functionalization of the two branches polymers.
Figure 23:
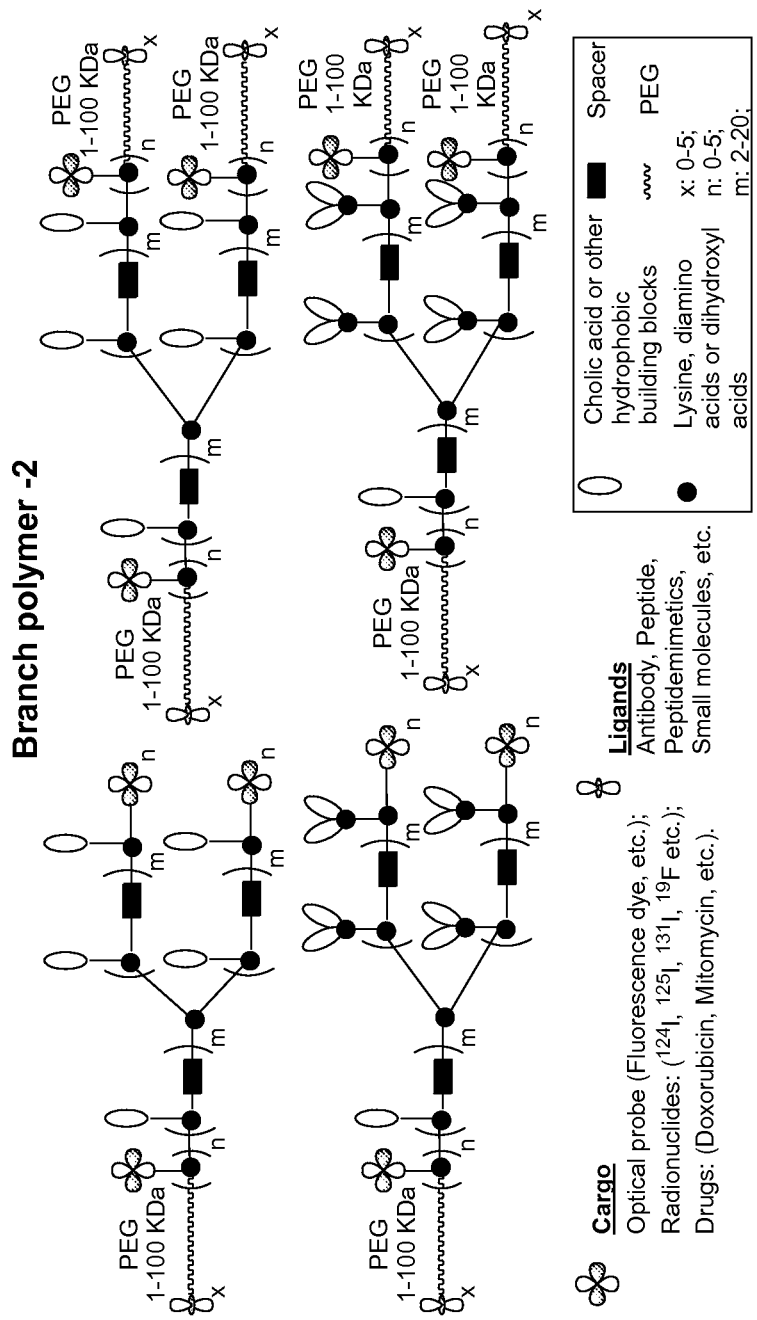
FIG. 23 shows the structure and functionalization of the three branches polymers.
Figure 24:
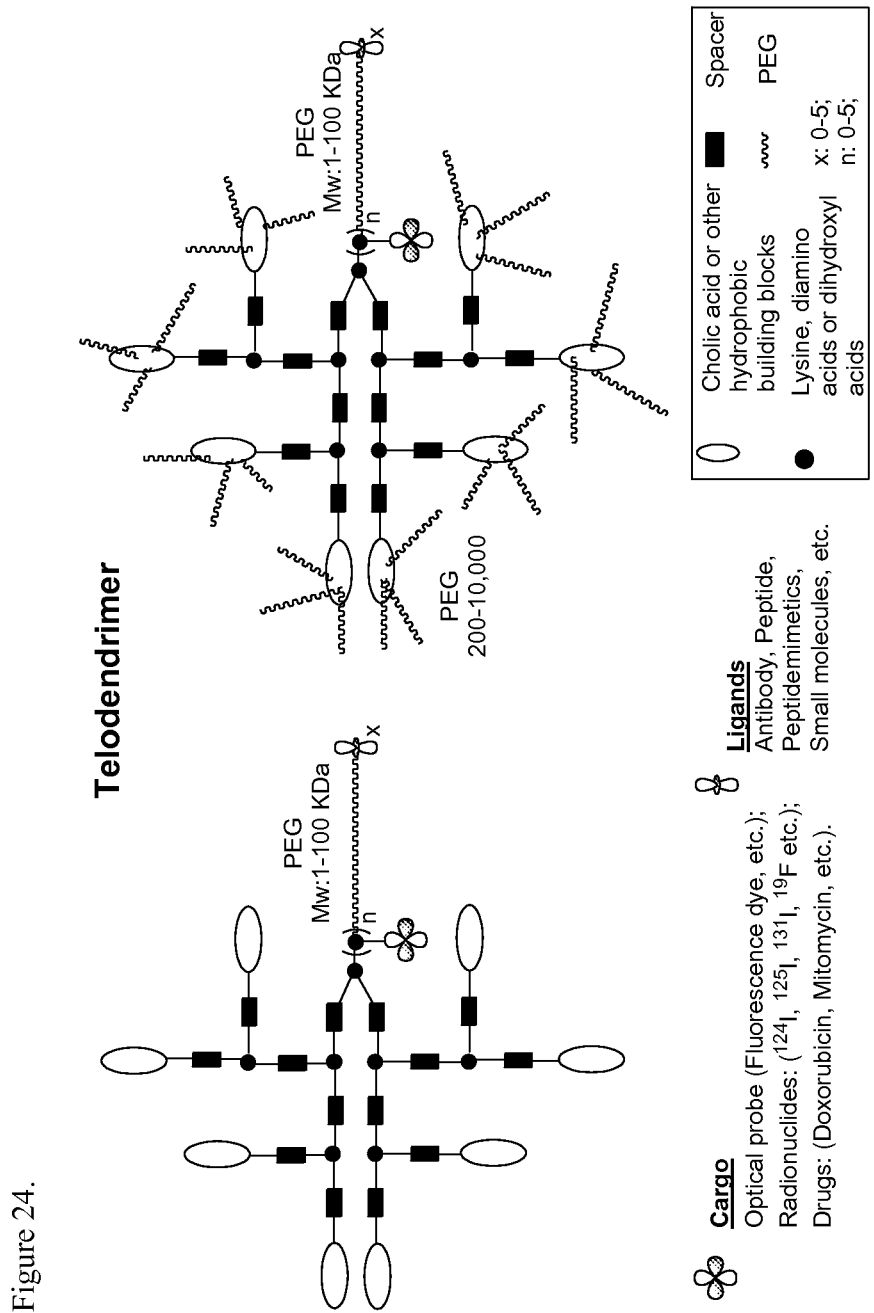
FIG. 24 shows the structure and functionalization of the telodendrimers.
Figure 25:
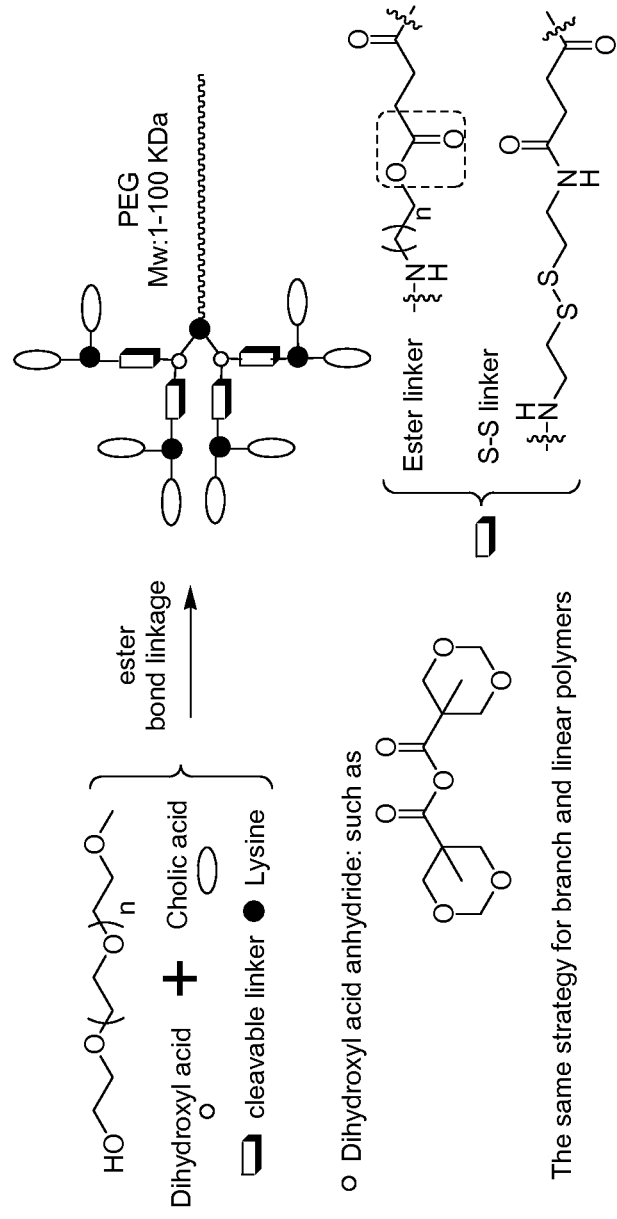
FIG. 25 shows the design of the biodegradable nanoparticles containing cleavable linkages between the building blocks.

In FIG. 19, the in vivo near infra-red (NIR) fluorescence imaging of subcutaneous Molt-4 tumor bearing mice at 48 h were recorded after the injections of four different nanoparticle-dye conjugates (NP($PEG^{3000}$-$CA_8$)-Cy5.5 and LLP2A-NP-Cy5.5 with and without PTX loading) at a dose of 4 nmol per mouse via tail vein. Fluorescence uptake into the tumors was observed in all four mice. Ex vivo imaging of the organs and the excised tumors were also performed (FIG. 20). The NP-dye conjugates were found to have high uptake in both Molt-4 and K562 tumors. Liver uptake was significant. However, uptake by other organs, including kidneys, was very low. In the mice administrated with NP-Cy5.5 and NP-Cy5.5-PTX, the Molt-4 tumor had significant higher uptake than the liver. However, the presence or absence of LLP2A ligand does not seem to affect uptake of the nanoparticles by the tumors or liver.

Example 13

Figure 35:
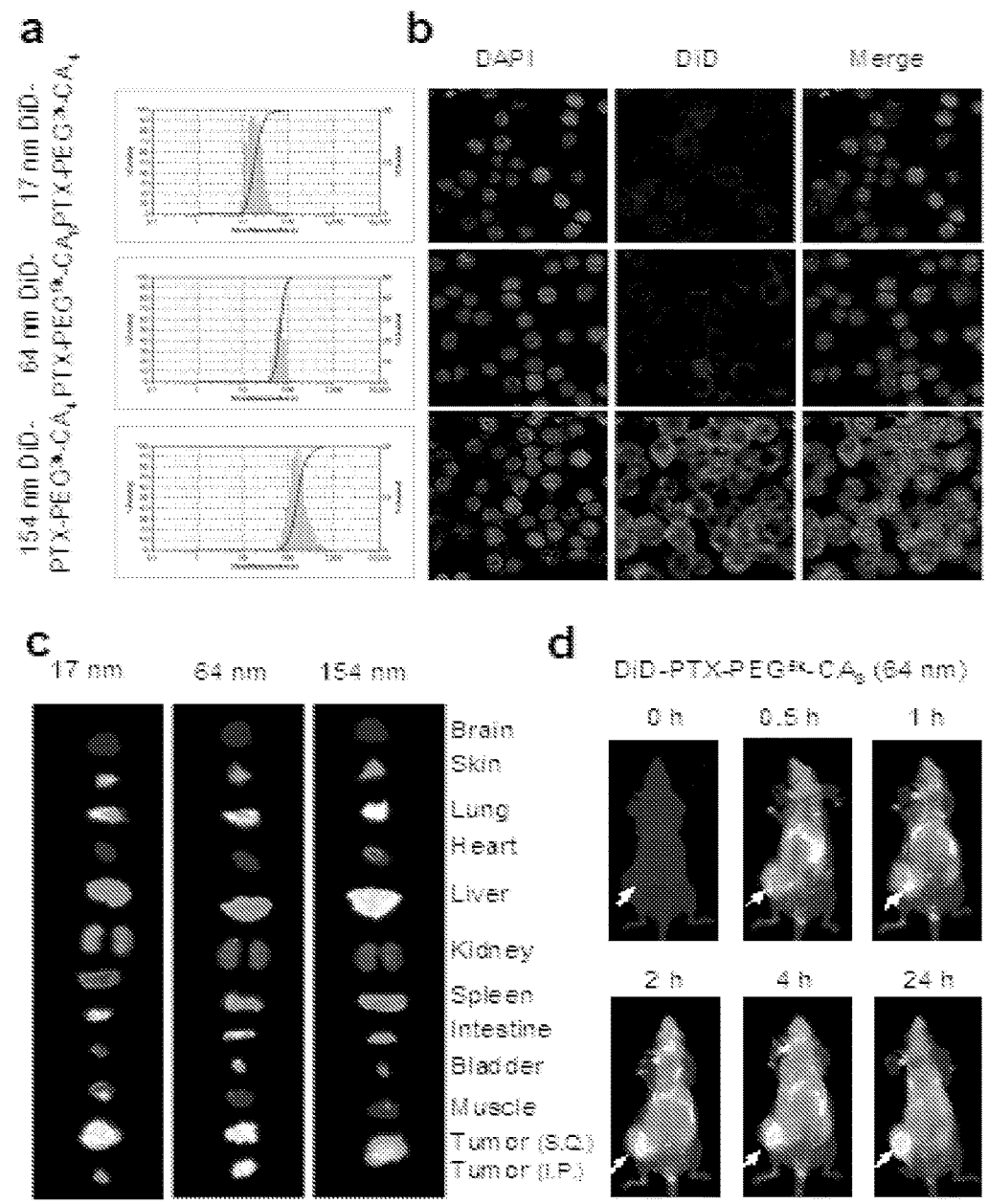
FIG. 35A shows three micelles, 154 nm DiD-PTX-$PEG^{3000}$-$CA_4$, 64 nm DiD-PTX-$PEG^{5000}$-$CA_8$, and 17 nm DiD-PTX-$PEG^{2000}$-$CA_4$, as measured with DLS particle sizer.
FIG. 35B shows 264.7 macrophage cells incubated with each of the three micelle preparations, and imaged under a confocal fluorescence microscope. The nuclei of the cells were stained with DAPI, the red DiD signals indicated that the 154 nm micelles, compared to the smaller micelles (17 nm and 64 nm) were preferentially taken up by the macrophages.
FIG. 35C shows ex vivo biodistribution of the micelles (three different sizes) in the SKOV-3 ovarian cancer xenograft bearing mice at 24 h after tail vein injection.
FIG. 35D shows in vivo NIR fluorescence imaging of the tumor bearing mice after i.v. injection with the DiD-PTX-PEG$^{5000}$-CA$_8$ over time; passive accumulation of the micelles in the S.Q. implanted xenograft (arrow) was observed from 2 h to 24 h after injection.

Size Effect on the Biodistribution of Nanocarriers in Xenograft Mice Model II To study the effects of particle size on the in vivo biodistribution of nanoparticles, the same concentration of DiD (a hydrophobic near infra-red (NIR) cyanine dye, 1 mg/mL) was co-loaded with PTX (4 mg/mL, 4 mg/mL and 3 mg/mL, respectively) into 20 mg/mL micelle solutions of PEG$^{2000}$-CA$_4$, PEG$^{5000}$-CA$_8$ and PEG$^{3000}$-CA$_4$, to form three fluorescence labeled micelle preparations with distinct sizes of 17 nm, 64 nm and 154 nm, respectively (FIG. 35a). Each of these three sizes of DiD-loaded micelles was incubated with Raw 264.7 macrophage cells for 2 h. The cells were then washed three times with PBS, fixed with 70% ethanol and observed under confocal fluorescence microscope. As shown in FIG. 35b, the larger micelles (154 nm), compared to the two smaller ones, were preferentially taken up the macrophages, which is consistent with the flow cytometry analysis data (data were not shown). NIR fluorescent imaging was used to evaluate the in vivo biodistribution of the three micelles with different sizes in nude mice bearing the SKOV-3 ovarian cancer xenografts (subcutaneous and intraperitoneal implants). The mice were injected via the tail vein with the same volume of the above three PTX-DiD loaded micelle preparations in PBS. Ex vivo imaging of the excised organs and tumors were performed at 24 h after injection. FIG. 35c shows that the larger nanoparticles (154 nm) exhibited highest fluorescence intensity in the liver and the lungs, likely due to nonspecific uptake by macrophages in those organs; but fluorescent uptake by the tumor was low. In contrast, tumor uptake of the smaller micelles (17 and 64 nm) was much higher than that of the normal organs. The in vivo NIR images of a tumor bearing mouse treated with the DiD-PTX-PEG$^{5000}$CA$_8$ was recorded over time (FIG. 35d). The accumulation of the DiD loaded micelles at the tumor site via the EPR effect began at 2 h after injection and continued to increase over the 24 h period. In contrast, no tumor targeting was found in the tumor-bearing mice treated with the free dye (images were not shown).

Example 14

NMR and CryoTEM Studies

NMR Studies.

Figure 33:
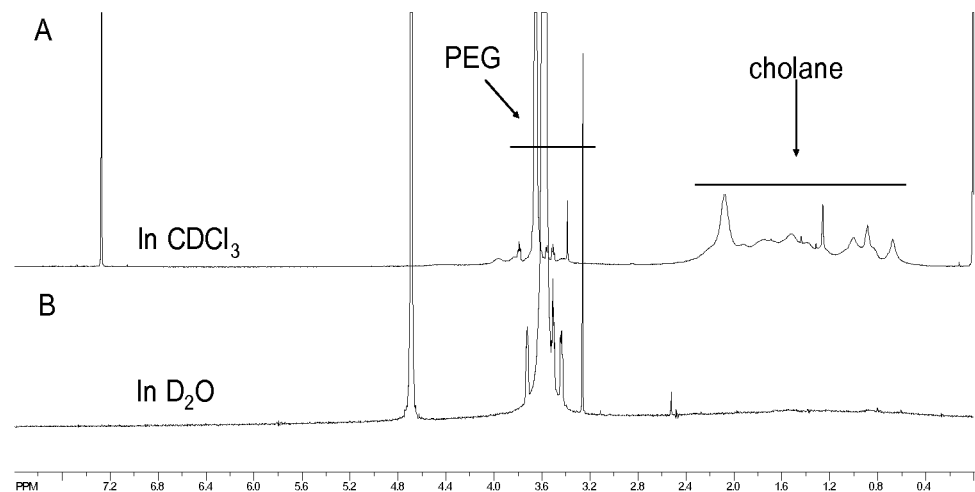
FIG. 33 shows the $^1H$ NMR spectra of $PEG^{5000}$-$CA_8$ (polymer 7) performed in $CDCl_3$ (A) and D2O (B)

As shown in FIG. 33A, the Proton NMR spectrum of the telodendrimer PEG$^{5000}$-CA$_8$ was collected in deuterated chloroform which is a good solvent for both PEG and cholic acid. The signals on hydrophilic PEG chains (3.3-3.6 ppm) and amphipilihc cholic acid (0.6-2.2 ppm) can be detected, and the ratio of the PEG chain and number of cholic acid were calculated based on the ratio of the integrated peaks PEG at 3.65 ppm and the intensity of one of methyl group (0.67 ppm) on cholic acid. Based on the NMR study, the formula is calculated to be PEG$^{5000}$-CA$_{7.3}$, which is very close to the theoretical formula PEG$^{5000}$-CA$_8$. However, when the NMR study was conducted in water, the signals (0.6-2.2 ppm) of dendritic cholic acid were not detected (FIG. 33B); only the protons of PEG (3.2-3.8 ppm) were detected. This demonstrates that the hydrophobic segments of cholic acid aggregated together in water, restricting the movement of the cholic acid moieties and significantly increasing the relaxation time (D$_2$) leading to weak signal in the NMR spectrum. This NMR data supports the model of micelles of telodendrimers in water.

CryoTEM Studies

Figure 34:
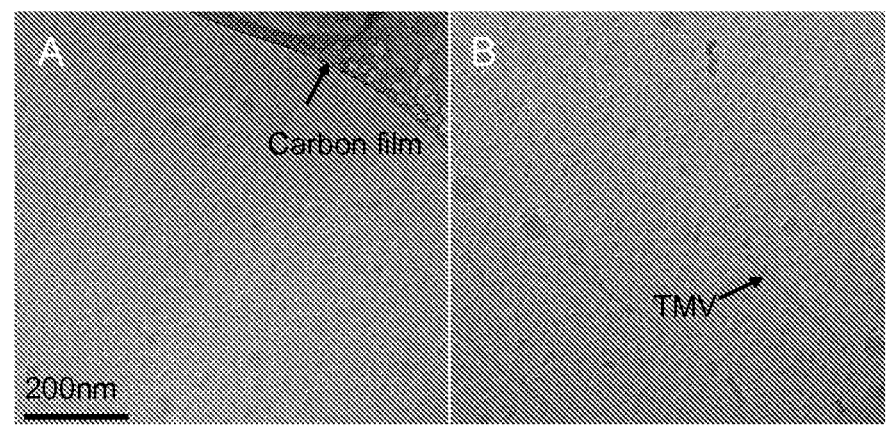
FIG. 34 shows CryoTEM images of $PEG^{5000}$-$CA_8$ (polymer 7) loaded with PTX (4.4 mg/mL) in the absence (34A) and presence of Tobacco Mosaic Virus (TMV) as calibration standard (18 nm in width) (34B), respectively.

CryoTEM allows observation of the real morphology and size of the hydrated micelles in aqueous conditions. After loading with PTX, the sizes of the micelle increase to 50 to 60 nm by DLS measurements. At the same time, the density of the micelle core increases. FIG. 34 shows a cryoEM images of PEG$^{5000}$-CA$_8$ loaded with PTX at 4.4 mg/mL. The micrograph was obtained in the absence (A) and presence (B) of Tobacco Mosaic Virus (TMV) as standard, which has a width of 18 nm. The spherical micelles were observed in size from 30 to 60 nm, which is consistent with the results obtained from DLS measurements (60 nm).

Example 15

Micelle Characterization by MALDI-ToF MS and AFM Images

MALDI ToF MS. In the study of the physical properties of telodendrimers and the in vivo passive tumor targeting effects of the nanoparticle, mono-functionalized MeO-PEG-NH$_2$ with different PEG chain length (2-10 kDa) were used for conjugating various number of CA (4, 8 and 16) in the dendritic blocks to prepare a series of telodendrimers (Table 1), MALDI-TOF mass spectrometry analysis showed a proportional increase in the molecular weight of telodendrimers with the increasing number of cholic acids (FIG. 36). The molecular weights obtained from MALDI-ToF MS method were very close to the theoretical values (Table 1), which strongly indicates the well-defined structures of telodendrimers, a feat that is very difficult to achieve with standard block-co-polymer approaches.

AFM Images.

Figure 37:
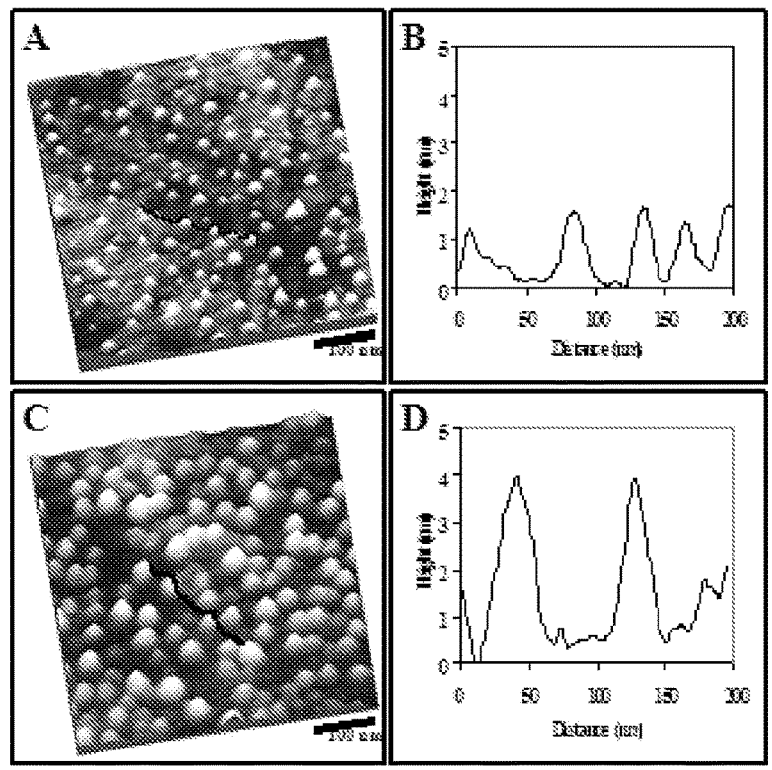
FIG. 37 shows tapping mode AFM topographs of the HS-PEG$^{5000}$-CA$_8$ micelles (37A) and PTX drug loaded HS-PEG$^{5000}$-CA$_8$ micelles (37C) on gold surfaces. Corresponding cursor profile is represented in (37B) and (37D), respectively, to review the 3D information.

Micelles (16±4 nm by DLS) and PTX-loaded micelles (6.4 mg PTX/mL, 23±8 nm by DLS) prepared from thiol-functionalized HS-PEG$^{5000}$-CA$_8$ (structure shown in FIG. 51) were immobilized on gold surfaces for AFM scanning. Tapping mode AFM topographs were obtained in aqueous solution. Both the empty and drug-loaded micelles appeared as individually immobilized nanoparticles with average sizes of 15 nm and 26 nm, respectively, which were close to the particle sizes obtained by DLS measurement (FIG. 37).

Example 16

Figure 38:
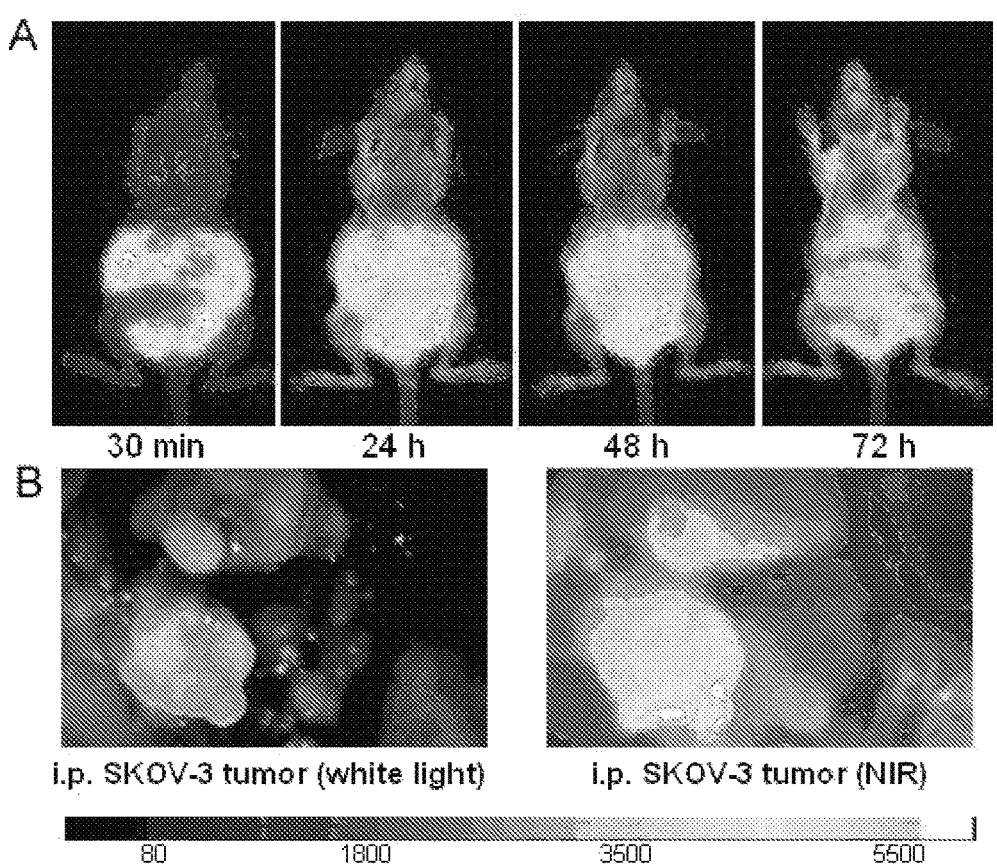
FIG. 38 shows intra-abdominal distribution of PEG$^{5000}$-CA$_8$ nanoparticles.

Size Effect on the Biodistribution of Nanocarriers in Xenograft Mice Model III PEG$^{5000}$-CA$_8$ (polymer 7) nanoparticles biodistribution after i.p. injection in intraperitoneal SKOV3-luc ovarian tumor bearing mice was investigated. Mice were injected i.p. with free DiD or DiD-loaded PEG$^{5000}$-CA$_8$ nanoparticles. In mice treated with free DiD, fluorescence rapidly diffused throughout the body post injection and declined to a level not distinguishable from background auto-fluorescence at 72 h. In contrast, mice injected with DiD-labeled PEG$^{5000}$-CA$_8$ nanoparticles resulted in strong fluorescence mainly localized in the abdominal region, with a majority still present at 72 h (FIG. 38A). At 72 h, the peritoneal cavity was exposed and scanned with the Kodak imaging station, displaying DID-labeled PEG$^{5000}$-CA$_8$ nanoparticles localization on the surface of peritoneal tumor nodules (FIG. 38). The results demonstrate that the PEG$^{5000}$-CA$_8$ drug carrier significantly extended the residence time of paclitaxel in the peritoneal cavity, reducing the rate and extent of drug absorption from the cavity into systemic circulation.

Example 17

In Vivo Efficacy Stud of PEG$^{5000}$-CA$_8$-PTX in Xenograft Mice Model II

Figure 39:
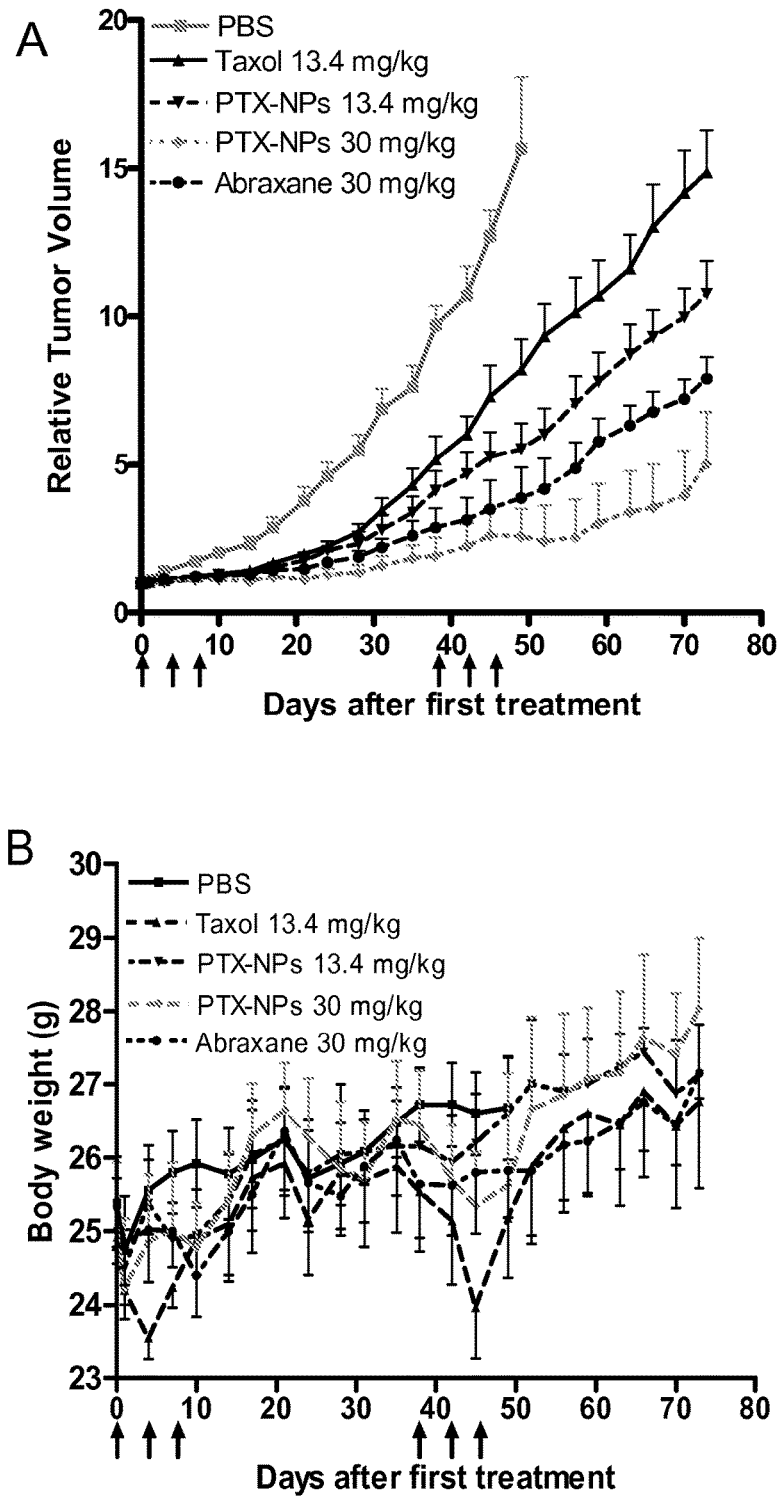
FIG. 39 shows in vivo anti-tumor efficacy by relative tumor volume (39A) and body weight changes of mice (39B) after intravenous treatment of different PTX formulations in the subcutaneous mouse model of SKOV3-luc ovarian cancer. Tumor bearing mice were administered i.v. with PBS (control), Taxol®, Abraxane® and PTX-PEG$^{5000}$-CA$_8$ NPs on days 0, 4, 8 and days 38, 42, 46 (arrows on X-axis) when tumor volume reached about 100~200 mm$^3$. Data represent mean±SEM of six mice per group.

The anti-tumor effects of PTX-PEG$^{5000}$-CA$_8$ NPs after intravenous injection were evaluated in subcutaneous SKOV3-luc tumor bearing mice. PBS, Taxol® (13.4 mg/kg), Abraxane (30 mg PTX/kg) and PTX-PEG$^{5000}$-CA$_8$ NPs (13.4 and 30 mg PTX/kg), were administered on days 0, 4, 8 (first course). Tumor growth was inhibited in mice treated with all the PTX formulations with the PTX-PEG$^{5000}$-CA$_8$ NPs at 30 mg PTX/kg being the most effective. However, tumor progression was subsequently noted in all these treatment groups. A second treatment cycle was initiated on day 38. Overall, mice showed decreased tumor growth rate after the intravenous administration of Taxol®, Abraxane® and PTX-PEG$^{5000}$-CA$_8$ NPs (FIG. 39A). However, PTX-PEG$^{5000}$-CA$_8$ exhibited superior anti-tumor activity as compared with Taxol®. By day 73, the median relative tumor volume (RTV) was 14.9 for Taxol, while the RTVs for 13.4 mg PTX/kg PTX-PEG$^{5000}$-CA$_8$ NPs, Abraxane and 30 mg PTX/kg PTX-PEG$^{5000}$-CA$_8$ NPs were 10.7, 7.9 and 5, respectively (P<0.05 for all), relative to starting tumor size. Furthermore, there was a single complete response noted in the 30 mg PTX/kg PTX-PEG$^{5"}$-CA$_8$ NPs group, but no complete responses in any other groups.

Toxicities were assessed by analyzing effects on animal behavior, body weight change, blood cell counts, and hepatic and renal functions. It was noted that mice receiving Taxol® treatment frequently demonstrated decreased overall activity over 10 min post injection, whereas no noticeable change in activity was observed after administration of either dose of PTX-PEG$^{5000}$-CA$_8$ NPs. This behavioral difference observed in the Taxol® group can be related to the use of Cremophor EL and ethanol as vehicle of paclitaxel. The Taxol® group exhibited significant body weigh loss during both treatment cycles (P<0.05), while the body weight didn't decrease in the PTX-PEG$^{5000}$-CA$_8$ NPs groups (FIG. 39B). On day 3 following the last injection, blood samples were collected for blood cell counts and serum chemistry measurement. White blood cell (WBC), red blood cell (RBC), and platelet counts in all the groups were within the normal range and excluded the potential hematologic toxicity. The serum chemistry (ALT, AST, Total bilirubin, BUN and Creatinine) in all the groups were also within the normal range, indicating an absence of hepatic and renal toxicity. Histological examination of the liver further confirmed the absence of hepatotoxicity.

Example 18

In Vivo Efficacy Stud of PEG$^{5000}$-CA$_8$-PTX in Xenograft Mice Model III

Figure 40:
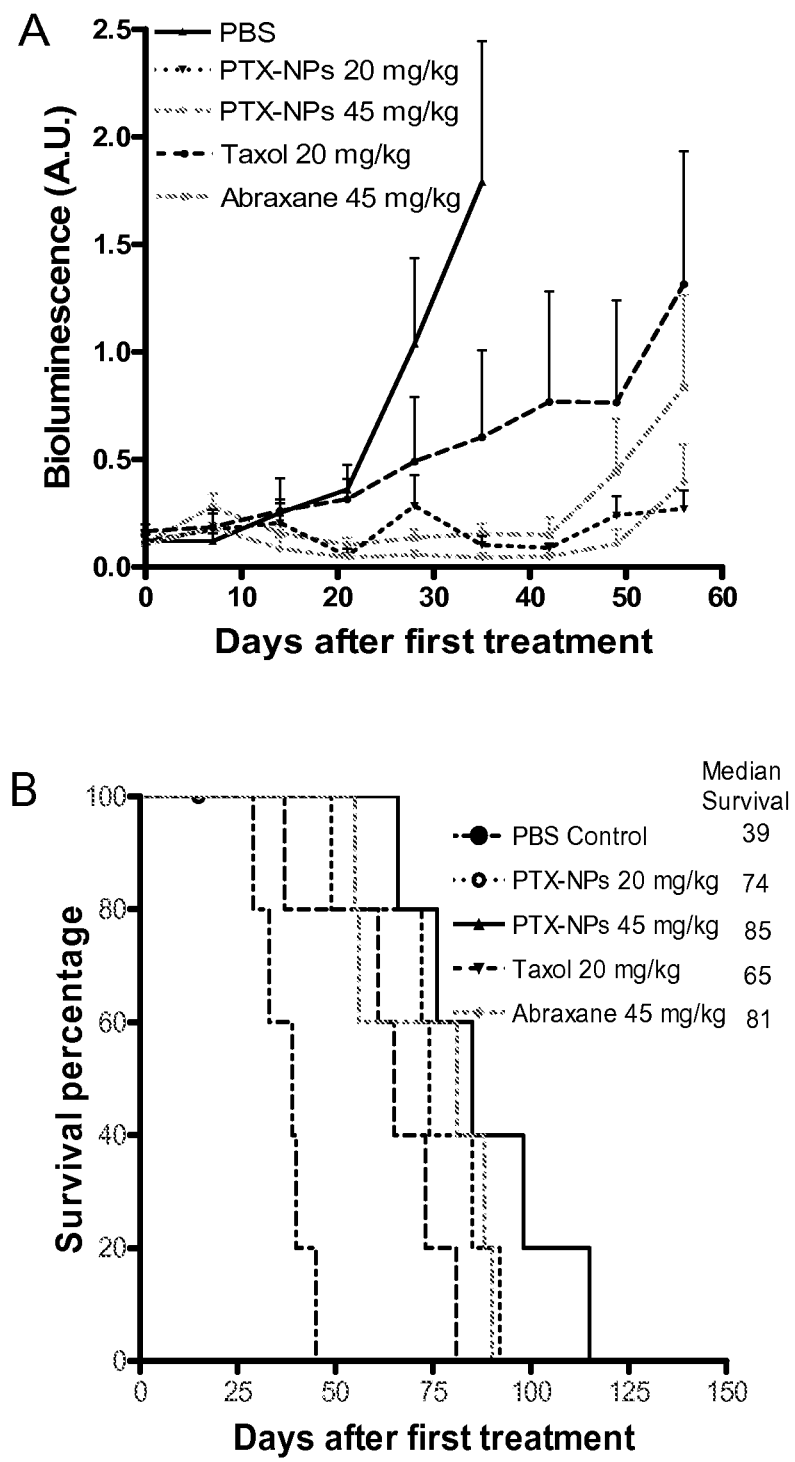
FIG. 40 shows the anti-tumor efficacy after intraperitoneal therapy of different PTX formulations and noninvasive bioluminescence imaging in a murine model of peritoneally disseminated ovarian cancer.

The therapeutic efficacy of PTX-PEG$^{5000}$-CA$_8$ NPs after i.p. therapy was evaluated and compared with Taxol® and Abraxane® in the orthotopic murine model of peritoneally metastatic ovarian cancer. Nude mice bearing i.p. metastatic SKOV3-luc ovarian tumor xenograft were injected i.p. with Taxol® (20 mg/kg), Abraxane® (45 mg PTX/kg) and PTX-PEG$^{5000}$-CA$_8$ (20 and 45 mg PTX/kg) for total 5 doses on day 0, 4, 8, 12 and 16. Bioluminescence imaging was performed weekly after treatment, and tumor bioluminesce was quantified by measuring pseudocolor intensity (FIG. 40A). Compared with the control group, mice in all the treatment groups displayed significantly slower increase rates of light intensity (P<0.05). Among treatment groups, light intensities in PTX-PEG$^{5000}$-CA$_8$ groups were lower than those of Taxol® and Abraxane® at equivalent PTX doses. Notably, one mouse in 20 mg PTX/kg PTX-PEG$^{5000}$-CA$_8$ NPs group and two mice in 45 mg PTX/kg PTX-PEG$^{5000}$-CA$_8$ NPs group experienced complete responses to therapy prior to subsequent relapses. Conversely, none of the mice treated with Taxol® demonstrated complete responses. All mice were also followed to determine the length of survival. Median survival time was 39 days (range 29-45) for untreated mice in the PBS control group, while the median survival time was significantly extended with all three PTX formulations treatment (P<0.001). However, PTX-PEG$^{5000}$-CA$_8$ NPs treatment exhibited greater survival benefit than Taxol® and Abraxane® at equivalent PTX doses. Median survival time for the Taxol® group was 65 days (range 37-81) and 74 days (range 49-92) for the 20 mg PTX/kg PTX-PEG$^{5"}$-CA$_8$ NPs group. Median survival was 81 days (range 55-90) for the Abraxane® group and 85 days (range 66-105+) for the 45 mg PTX/kg PTX-PEG$^{5000}$-CA$_8$ NPs group (FIG. 40B).

Example 19

Preparation of Branched Polymer Series P-1

The linear PEGylated two-arm oligomer of cholic acids were synthesized via stepwise peptide chemistry. For example, we started to synthesize P-1 series polymers from linear polyethylene glycol via solution phase reactions (FIG. 41). 3-azidopropylamine (3 eq.) was coupled onto the carboxylic group of the FmocNH-PEG-COOH (3000 Da) using N-Hydroxybenzotriazole (HOBt 3 eq.)/diisopropyl carbodimide (DIC 3 eq.) as coupling agents in DMF overnight. The polymer was subsequently precipitated and washed with cold ether. After removal of the Fmoc via a 20% piperidine solution in DMF, (Fmoc)Lys(Dde)-OH (3 eq.) was coupled onto the N terminus of PEG using DIC and HOBt as coupling reagents until a negative Kais test result was obtained, thereby indicating completion of the coupling reaction. The PEGylated compounds were then precipitated and washed with cold ether. Then (Fmoc)Lys(Fmoc)-OH (3 eq.), (Fmoc)Ebes-OH (6 eq.), (Fmoc)Lys(Boc)-OH (6 eq.) were coupled to the above PEGylated products step by step via the same Fmoc peptide synthesis procedure. The scaffolds of polymer 21, polymer 22, polymer 23 and polymer 24 were built by repeating the coupling of (Fmoc)Ebes-OH and (Fmoc)lys(Boc)-OH 2, 3, 4 and 5 times, respectively. After removal of Boc and Fmoc group, cholic acid NHS ester reacted with the free amino groups of the scaffolds to generate the four polymers in P-1 series. The polymers were precipitated and washed by cold ether and dissolved in water. The polymer solution was filtered and then dialyzed against 4 L water in a dialysis tube with MWCO of 3.5 KDa; reservoir water was refreshed completely four times in 24 h. Finally, the polymers were lyophilized. P-2, P-3 and P-4 series were synthesized with the similar strategy by using the different combinations of Fmoc-lys(Fmoc)-OH and Fmoc-lys(Boc)-OH as well as different rounds of coupling and Fmoc deprotection.

Example 20

TEM Images of the Polymer P-1 and P-2 Series

Figure 42:
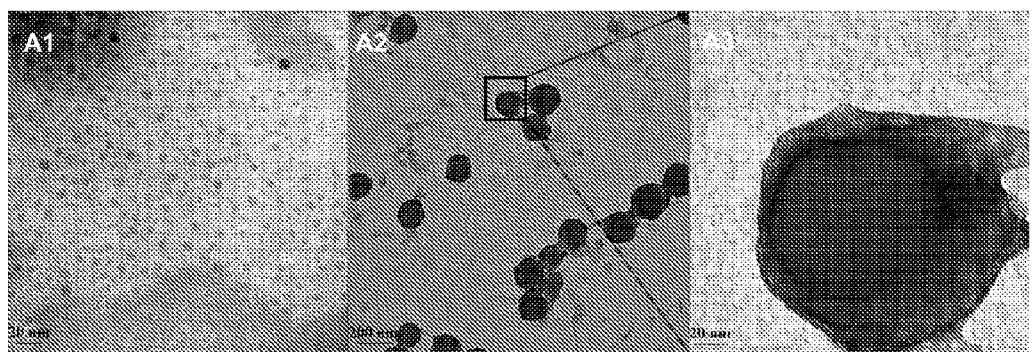
FIG. 42 shows TEM images of unloaded polymer 23 micelles (A1), unloaded Polymer 25 micelles (low magnification) (A2), and unloaded polymer 25 micelles (high magnification) (A3).

Micelle morphology was observed under a transmission electron microscopy (TEM) after staining the air-dried micelles with phosphotungstic acid (0.1 wt %). As shown in FIG. 42(A1), both the smaller polymer 23 (~10 nm) and the larger polymer 25 (~150 nm) micelles retained circular shapes and size uniformity. Under higher magnification, the clear core-shell structure of polymer 25 was evident (FIG. 42 A3). The dynamic light scattering (DLS) measurements showed that the mean diameters of polymer 23 and polymer 25 micelles were 11 and 157 nm, respectively, which were consistent with those observed under TEM.

Example 21

PTX Loading in P-1, P-2 and P-3 Series Polymers and their Sizes

A variety of poor water soluble anti-tumor drugs can be encapsulated into these micelles efficiently by solvent evaporation method. Paclitaxel (PTX) is a wide-spectrum antineoplastic used to treat various malignant tumors. Due to the very low water solubility (1 µg/mL) of PTX, the commercial preparation of PTX (Taxol®) is formulated in a mixture of dehydrated alcohol and Cremophor EL, which may cause serious side effects. Abraxane® is a 130 nm albumin-bound particle formulation of paclitaxel. Here we demonstrated that PTX can be easily loaded into our micelles in an aqueous solution (FIG. 43A). It was observed that the micelles with CMC values in a range of 4.5-7.8 µM tend to have better PTX loading capacity (≥4.5 mg/mL) than micelles having either lower or higher CMC values. polymer 23 micelles (CMC: 5.8 µM) had the highest paclitaxel loading capacity at 12.0 mg/mL (FIG. 43B), which was equivalent to 37.5% (w/w) of the total mass of the micelle. This indicated that the polymer 23 micelle formulation of PTX could provide a 12,000 fold increase in the water solubility of this drug. Thus, in terms of drug loading capacity, polymer 23 micelle was far superior to the two clinical PTX formulations, Taxol® (6.0 mg/mL) and Abraxane® (5.0 mg/mL), and other conventional micelle formulations reported to have PTX loading capacities of less than 25%. Moreover, loading efficiency was nearly 100% when PTX was added up to 10 mg/mL and the final particle sizes still remained in the range of 25-30 nm (FIG. 43B, 43C).

Example 22

PTX Release from Micelles Formed by Polymer 23

Figure 44:
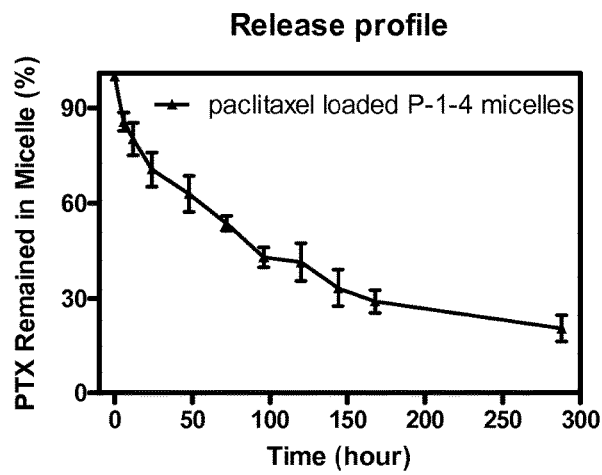
FIG. 44 shows the release profile of PTX from P-1-4 (Polymer 23) micelles in PBS at 37° C., as measured by the percentage of PTX remaining in the micelle over time. The initial paclitaxel concentration was 1.2 mg/mL. The concentration of paclitaxel remained in the dialysis cartridge at various time points was measured by HPLC. Values reported are the mean±SD for triplicate samples.

The PTX release profile of PTX loaded micelles was investigated in PBS at 37° C. PTX loaded polymer 23 micelles showed no obvious "burst release" within 24 h (<30%) in the drug release study, and PTX release continued for up to 7 days (FIG. 44). At the end of test, 80% of loaded PTX has been released from the micelles.

Example 23

Stability of the PTX-Loaded Micelles Formed by Polymer 23

Figure 45:
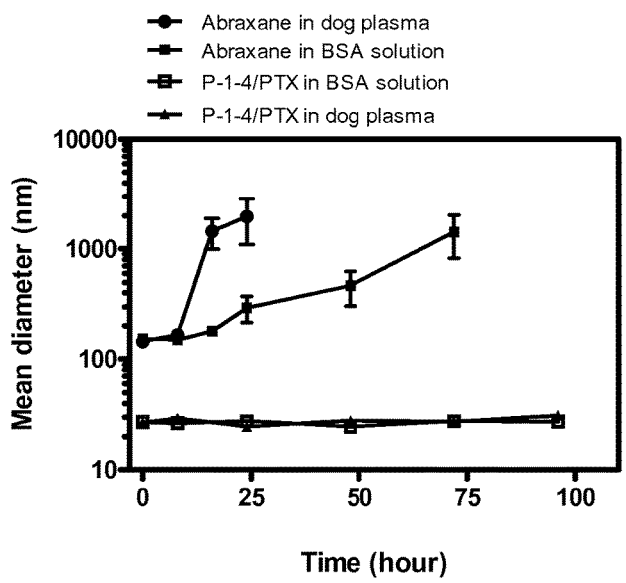
FIG. 45 shows the mean diameter over time, as measured by dynamic light scattering, of Abraxane® (paclitaxel loading: 5.0 mg/mL) and P-1-4 (Polymer 23) micelles loaded with 7.3 mg/mL of paclitaxel, in dog plasma 50% (v/v) and in 45 mg/mL of BSA solution in PBS at 37° C. All measurements were repeated three times. Values reported are the mean diameter±SD for two replicate samples.

The long-term stability of these micelle formulations was evaluated in storage at 4° C. The drug loaded micelles were stored at 4° C. for over 8 months and observed to be very stable in both size and drug content. In contrast, Abraxane® formed larger aggregates and precipitated after two days of storage. Furthermore, a basic evaluation of pharmacokinetic modeling and efficacy data for micelles or drug loaded micelles in animal models was conducted, testing the stability of micelles or drug loaded micelles in the presence of serum or serum albumins. Similarly, polymer 23 micelles with a PTX loading of 7.3 mg/mL retained a uniform size at around 30 nm over the 96 h incubation period in the presence of physiologically relevant concentrations of bovine serum albumin (BSA) (45 mg/mL) and in 50% (v/v) dog plasma at 37° C. (FIG. 45). In contrast, significant size variations were observed for Abraxane® under such conditions. These in vitro stability studies suggest that these PTX loaded micelles may have a long circulation time under physiological conditions. It has been reported that drug-loaded polymeric micelles generally become more unstable as drug loading increases. In contrast, the micelle formed by polymer 23 remains very stable in storage or under physiological conditions even at very high level drug loading.

Example 24

Cytotoxicity of the PTX-Loaded Micelles Formed by P-1 Series Polymers

Figure 46:
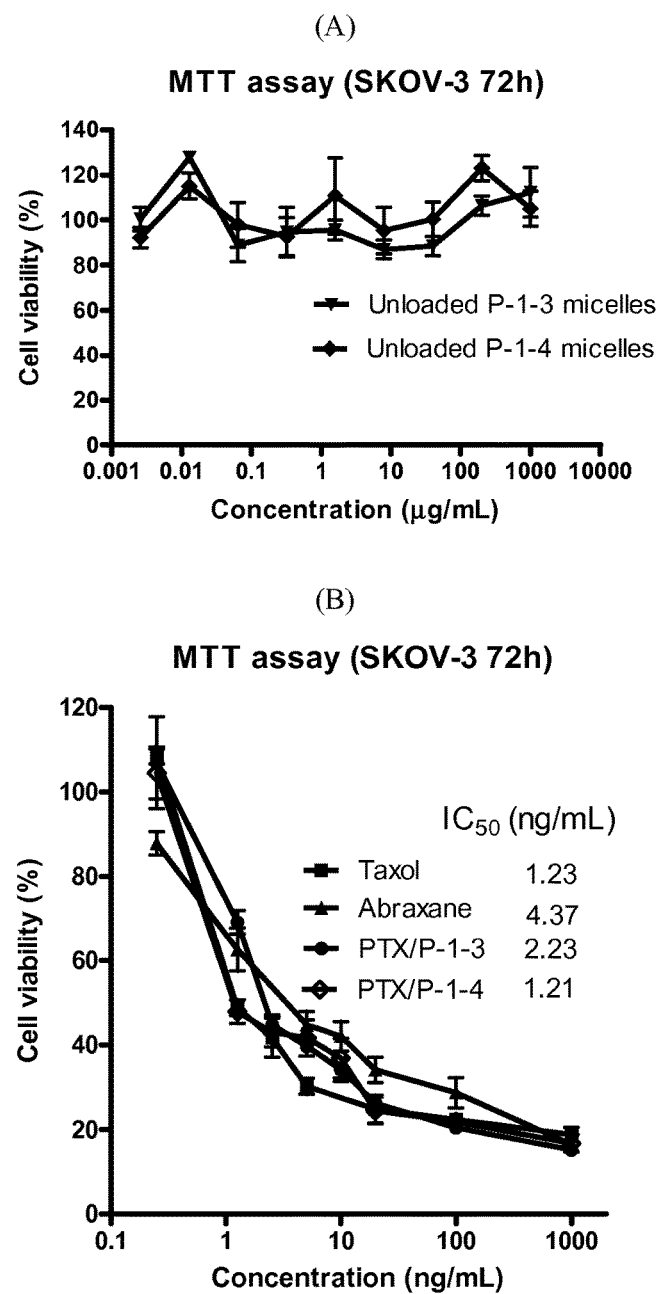
FIG. 46 shows MTT assays demonstrating the viability of SKOV-3 cells treated with different concentrations of unloaded ("blank") P-1-3 (polymer 22) micelles, unloaded P-1-4 (polymer 23) micelles (46A), and Taxol®, Abraxane®, PTX loaded P-1-3 (polymer 22) micelles and PTX loaded P-1-4 micelles (46B) after 72 h incubation. The cell viability was calculated as the ratio of cell number in the treated sample divided by that in the untreated control. Values reported are the mean±SD for triplicate samples.

To be clinically useful, the nanocarrier itself should be non-toxic. The four building blocks of the novel polymers are all biocompatible molecules. The nanocarrier itself showed no observable cytotoxicity up to 1 mg/mL against SKOV-3 ovarian cancer cells by MTT assay (FIG. 46A). PTX loaded nanocarriers have comparable in vitro antitumor effects as the two clinical formulations of paclitaxel (Taxol® and Abraxane®), with $IC_{50}$ values ranging from 1.21 to 4.37 ng/mL on SKOV-3 ovarian cancer cells (FIG. 46B).

Example 25

Biodistribution of Micelles in Ovarian Cancer Xenograft Mouse Model

Figure 47:
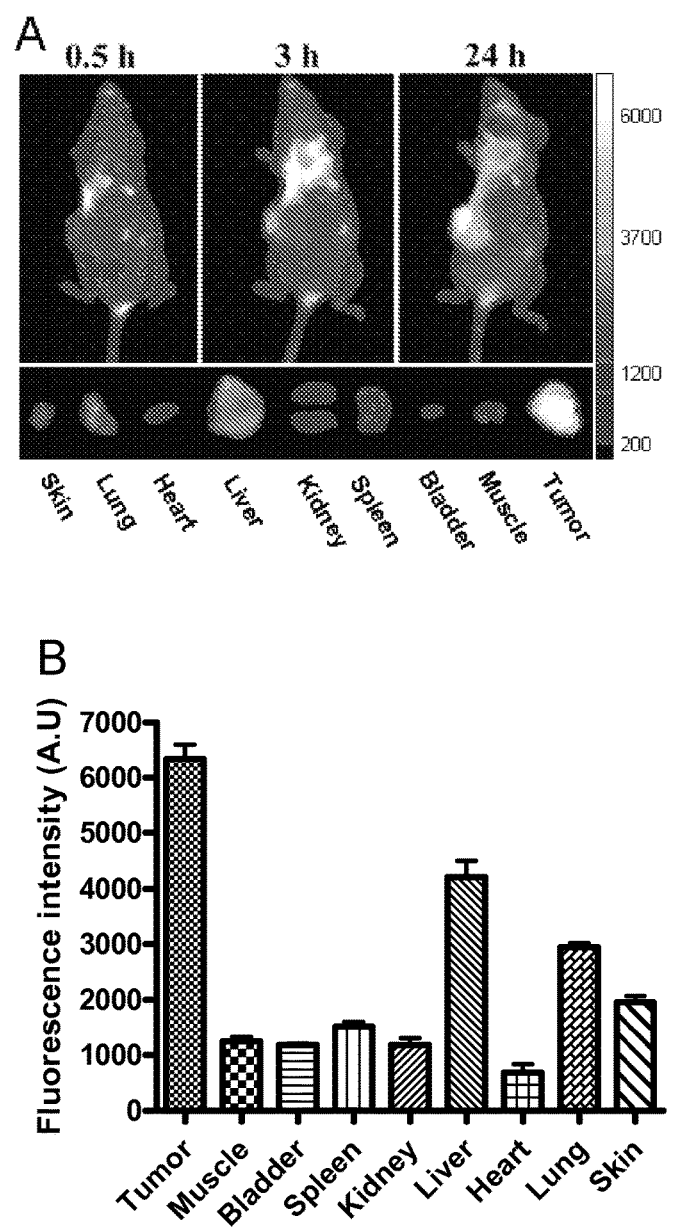
FIG. 47 shows in vivo and ex vivo NIR optical images.

Hydrophobic fluorescent probes can be physically incorporated into micelles for in vivo tracking. Hereby, 1,1'-dioctadecyl-3,3,3',3'-tetramethylindo-dicarbocyanine perchlorate (DiD), a hydrophobic near infrared (NIR) fluorescent dye, was loaded together with PTX into polymer 23 micelles. The particle size of the final micelle was 30±10 nm as determined by DLS. NIR optical imaging studies were performed to evaluate the biodistribution and tumor targeting ability of the nanocarrier in mice bearing human SKOV-3 ovarian cancer xenograft. 100 µL of DiD and PTX co-loaded micelle solution was injected into mice via tail vein, and then the mice were scanned with a Kodak imaging system (IS2000 mM) at different time points. The contrast of fluorescence signal was observed between tumor and background at 3 h post injection, and became more significant at 24 h (FIG. 47A). Ex vivo imaging further confirmed that nanocarriers preferentially accumulate in tumor other than normal organs (FIG. 47B). This is probably due to the prolongation of in vivo circulation time of the micelles and the size-mediated enhanced permeability and retention (EPR) effect.

Example 26

Preparation of Thiolated Telodendrimer HS-PEG$^{5000}$-CA$_8$

Figure 51:
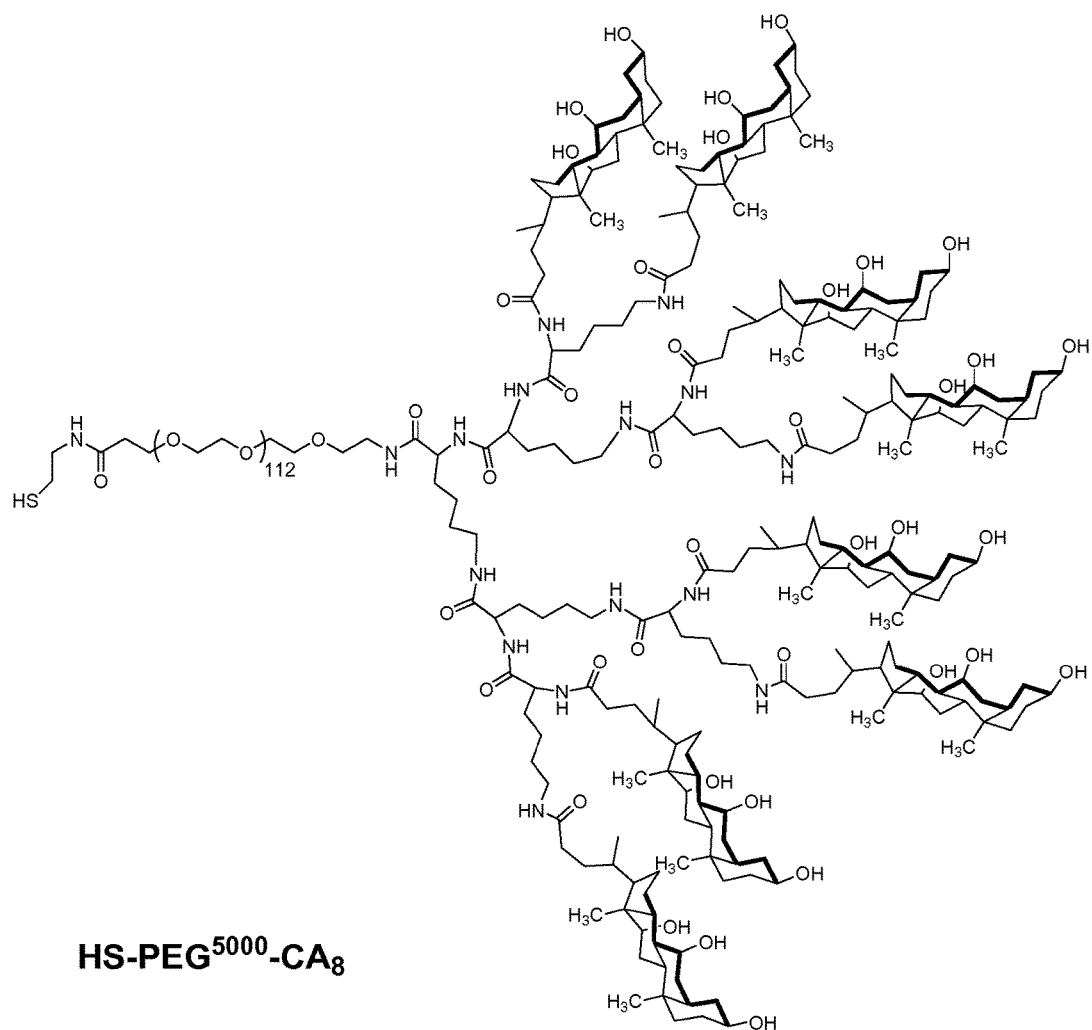
FIG. 51 shows the structure of HS-PEG$^{5000}$-CA$_8$.
Figure 52A:
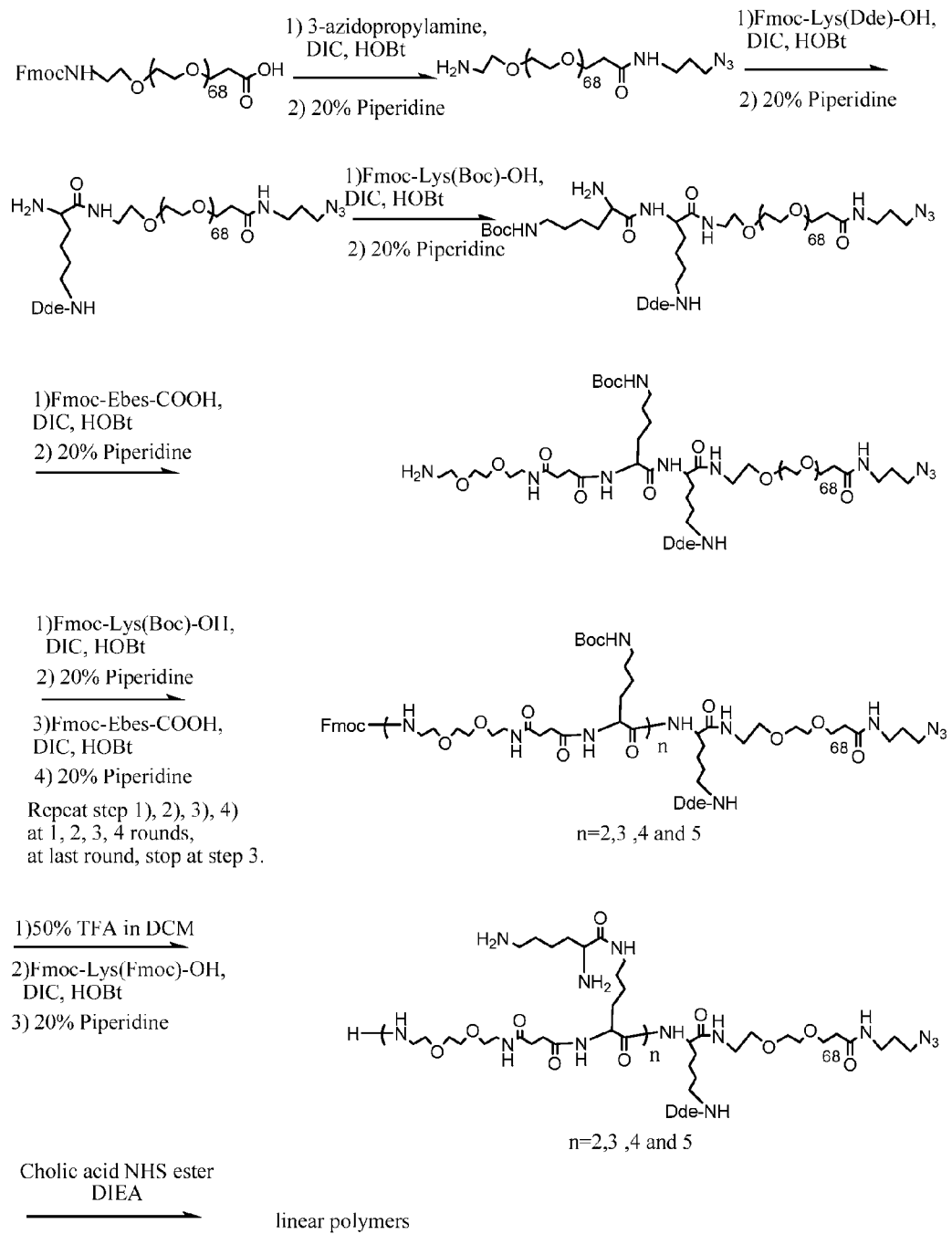
FIGS. 52A and 52B show the synthesis (52A) of members of the linear polymer series and products (52B) of the synthesis.
Figure 52B:
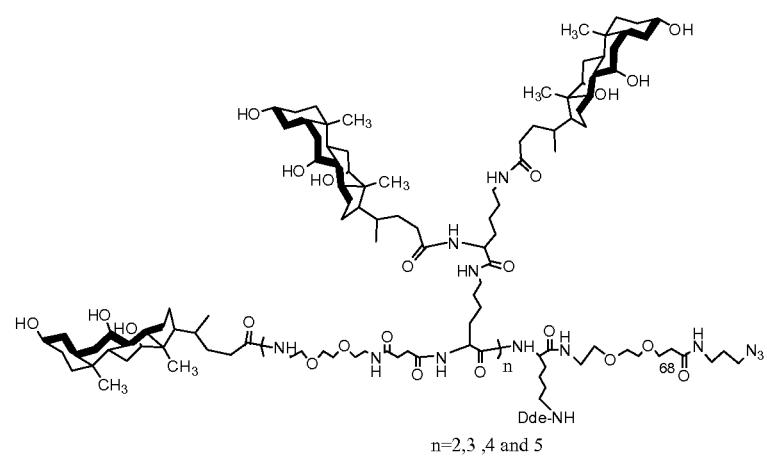

The thiolated Telodendrimer HS-PEG$^{5000}$-CA$_8$ was synthesized on a linear polyethylene glycol via solution phase condensation reactions (FIG. 51). The isolation of soluble PEGylated products was achieved by precipitation in cold ether. An S-Trtyl protected 2-thiolethylamine was coupled onto a carboxylic group of the Fmoc protected amino-PEG-COOH with a molecular weight of 5000 Da. After remove of the Fmoc with the treatment of 20% piperidine solution in DMF, (Fmoc)Lys(Fmoc)-OH was coupled onto the N terminal of PEG using DIC and HOBt as coupling reagents. A third generation of the dendritic polylysine was prepared via the repeated coupling of (Fmoc)lys(Fmoc)-OH via Fmoc peptide synthesis. Cholic acid were introduced onto the amino groups of the branched lysine via cholic acid NHS ester. The trtyl group was removed by the treatment with 50% of TFA in DCM to generate HS-PEG$^{5000}$-CA$_8$, which can be immobilized onto a gold surface for the AFM images of the micelles.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A nanocarrier having an interior and an exterior, the nanocarrier comprising at least one conjugate having formula III:

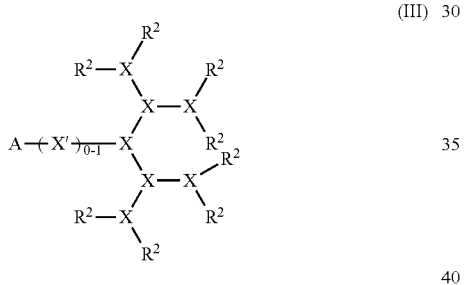

(III)

Wherein
A is a polyethylene glycol (PEG) polymer;
each X is a monomer unit comprising a diaminocarboxylic acid;
X' is a monomer unit selected from the group consisting of a diaminocarboxylic acid, an NH, and an O, optionally linked to a member selected from the group consisting of an optical probe, a radionuclide, a paramagnetic agent, a metal chelate and a drug; and
each R$^2$ is independently an amphiphilic compound having both a hydrophilic face and a hydrophobic face, wherein each amphiphilic compound is independently selected from the group consisting of cholic acid, allocholic acid, pythocholic acid, avicholic acid, deoxycholic acid, and chenodeoxycholic acid;
wherein each conjugate self-assembles in an aqueous solvent to form the nanocarrier such that a hydrophobic pocket is formed in the interior of the nanocarrier by the orientation of the hydrophobic face of each amphiphilic compound towards each other, and wherein the PEG of each conjugate self-assembles on the exterior of the nanocarrier.

2. The nanocarrier of claim 1, wherein the nanocarrier further comprises a hydrophobic drug or an imaging agent, such that the hydrophobic drug or imaging agent is sequestered in the hydrophobic pocket of the nanocarrier.

3. The nanocarrier of claim 1, wherein the diamino carboxylic acid is an amino acid.

4. The nanocarrier of claim 1, wherein each diamino carboxylic acid is independently selected from the group consisting of 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid.

5. The nanocarrier of claim 1, wherein at least one of the monomer units is optionally linked to a member selected from the group consisting of an optical probe, a radionuclide, a paramagnetic agent, a metal chelate and a drug.

6. The nanocarrier of claim 2, wherein the hydrophobic drug is selected from the group consisting of paclitaxel, SN38, camptothecin, etoposide and doxorubicin.

7. The nanocarrier of claim 1, wherein
A is the polyethyleneglycol (PEG) polymer of 1-100 kDa, wherein A is optionally linked to a binding ligand L; and
each R$^2$ is cholic acid, wherein each cholic acid group is optionally substituted with 1-3 polyethyleneglycol (PEG) polymers each independently 200-10,000 Da in size.

8. The nanocarrier of claim 7, the conjugate having formula IIIa:

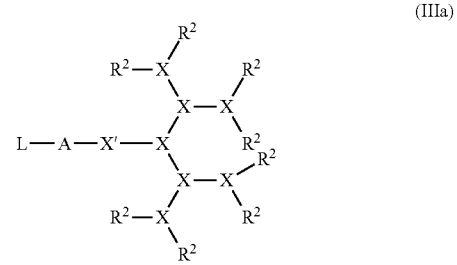

(IIIa)

wherein
A is a PEG polymer of 5 kDa;
the monomer unit of X' is lysine;
each X is lysine;
and each R$^2$ is cholic acid.

* * * * *